US012724175B2

(12) United States Patent
Acerson et al.

(10) Patent No.: US 12,724,175 B2
(45) Date of Patent: Sep. 1, 2026

(54) CONTACT LENS WITH OPTICAL PROPHYLAXIS

(71) Applicant: High Performance Optics, Inc., Roanoke, VA (US)

(72) Inventors: Mark Acerson, North Logan, UT (US); David Owen Baumann, Hyrum, UT (US); Dustin Cefalo, Logan, UT (US); Frank Chang, Cumming, GA (US); Peter Haaland, Belmont, MA (US); Troy Holland, Suwanee, GA (US); Andrew Ishak, Aberdeen, MD (US); Raja Gabadage Waruna E. Jinadasa, North Logan, UT (US); Mark L. Nelson, Midway, UT (US); Larry Rodriguez, Concord, NC (US); Adam Sniady, Lilburn, GA (US); Houliang Tang, Alpharetta, GA (US); Jiangxing Zhang, Salt Lake City, UT (US)

(73) Assignee: High Performance Optics, Inc., Roanoke, VA (US)

( * ) Notice: Subject to any disclaimer, the term of this patent is extended or adjusted under 35 U.S.C. 154(b) by 731 days.

(21) Appl. No.: 17/978,286

(22) Filed: Nov. 1, 2022

(65) Prior Publication Data

US 2023/0138968 A1 May 4, 2023

Related U.S. Application Data

(60) Provisional application No. 63/275,159, filed on Nov. 3, 2021.

(51) Int. Cl.

*C07D 487/22* (2006.01)
*G02B 1/04* (2006.01)
*G02C 7/04* (2006.01)

(52) U.S. Cl.

CPC ........... *G02B 1/043* (2013.01); *C07D 487/22* (2013.01); *G02C 7/04* (2013.01)

(58) Field of Classification Search

CPC ......... C07D 487/22; G02B 1/043; G02C 7/04
See application file for complete search history.

(56) References Cited

U.S. PATENT DOCUMENTS

| | | | |
|---|---|---|---|
| 7,022,843 | B1 | 4/2006 | MacAlpine et al. |
| 7,276,544 | B2 | 10/2007 | Lai et al. |
| 7,364,291 | B2 | 4/2008 | Haywood et al. |
| 7,520,608 | B2 | 4/2009 | Ishak et al. |
| 7,556,376 | B2 | 7/2009 | Ishak et al. |
| 8,113,651 | B2 | 2/2012 | Blum et al. |
| 8,360,574 | B2 | 1/2013 | Ishak et al. |
| 8,882,267 | B2 | 11/2014 | Ishak et al. |
| 9,063,349 | B2 | 6/2015 | Ishak et al. |
| 9,377,569 | B2 | 6/2016 | Ishak et al. |
| 9,683,102 | B2 | 6/2017 | Cefalo et al. |
| 9,798,163 | B2 | 10/2017 | Ishak et al. |
| 9,814,658 | B2 | 11/2017 | Ishak et al. |
| 10,545,264 | B1 | 1/2020 | Haaland |
| 10,551,637 | B2 | 2/2020 | Ishak et al. |
| 10,610,472 | B2 | 4/2020 | Ishak et al. |
| 10,935,709 | B2 | 3/2021 | Haaland |
| 11,701,315 | B2 | 7/2023 | Ishak et al. |
| 11,774,783 | B2 | 10/2023 | Ishak et al. |
| 2021/0132416 | A1 | 5/2021 | Newman et al. |

FOREIGN PATENT DOCUMENTS

| | | | |
|---|---|---|---|
| EP | 3424688 | A1 | 1/2019 |
| WO | WO 2014/189796 | A1 | 11/2014 |

OTHER PUBLICATIONS

Kralova (J. Med. Chem. 2003, 46, 2049-2056). (Year: 2003).*

Li (ACS Appl. Mater. Interfaces 2016, 8, 3624-3634). (Year: 2016).*

Ogawa (Journal of Chemical Research 2020, vol. 44(9-10) 613-617). (Year: 2020).*

Pechnikova (Russian Journal of General Chemistry, 2016, vol. 86, No. 6, pp. 1505-1509). (Year: 2016).*

Ozkan (Eur. J. Org. Chem. 2019, 3534â3541). (Year: 2019).*

Liu (Chem. Eur. J. 2018, 24, 4239 â 4244). (Year: 2018).*

Brainard et al., Action spectrum for melatonin regulation in humans: evidence for a novel circadian photoreceptor. J Neurosci. Aug. 15, 2001;21(16):6405-12. doi: 10.1523/JNEUROSCI.21-16-06405. 2001.

Fekete et al., Spectral discomfort glare sensitivity under low photopic conditions. Ophthalmic Physiol Opt. May 2006;26(3):313-7. doi: 10.1111/j.1475-1313.2006.00359.x.

Romney et al., Munsell reflectance spectra represented in three-dimensional Euclidean space. Col Res Appl. Jun. 2003;28(3):182-196. doi: .org/10.1002/col.10144.

Taniguchi et al., Database of Absorption and Fluorescence Spectra of >300 Common Compounds for use in PhotochemCAD. Photochem Photobiol. Mar. 2018;94(2):290-327. doi: 10.1111/php.12860. Epub Feb. 13, 2018.

Invitation to Pay Additional Fees for Application No. PCT/US2022/048515, mailed Jan. 30, 2023.

(Continued)

*Primary Examiner* — Kortney L. Klinkel
*Assistant Examiner* — Richard Grant Peckham
(74) *Attorney, Agent, or Firm* — Wolf, Greenfield & Sacks, P.C.

(57) ABSTRACT

The present disclosure provides metalloporphyrin and metallochlorin compounds (e.g., compounds of Formula (II) and (III)), which are useful in the preparation of optical devices (e.g., contact lenses, intraocular lenses, implantable contact lenses) that protect retinal pigment epithelium by the selective blocking of blue light. Also provided are precursor porphyrin and chlorin compounds (e.g., compounds of Formula (I)), and compositions and optical devices incorporating the compounds of the disclosure. Also provided are methods of selecting appropriate metalloporphyrin and metallochlorin compounds for incorporation into optical devices wherein the devices mitigate damage to retinal epithelial cells while balancing changes to luminous transmission, discomfort glare, color distortion, and disruption of circadian rhythms.

7 Claims, 23 Drawing Sheets

(56) References Cited

OTHER PUBLICATIONS

International Search Report and Written Opinion for Application No. PCT/US2022/048515, mailed Apr. 7, 2023.
International Preliminary Report on Patentability for Application No. PCT/US2022/048515, mailed May 16, 2024.
Aravindu et al., Synthesis and photophysical properties of chlorins bearing 0-4 distinct meso- substituents. Photochem Photobiol Sci. Dec. 2013;12(12):2089-109. doi: 10.1039/c3pp50240f.
Berg et al., Disulfonated tetraphenyl chlorin (TPCS2a), a novel photosensitizer developed for clinical utilization of photochemical internalization. Photochem Photobiol Sci. Oct. 2011;10(10):1637-51. doi: 10.1039/c1pp05128h. Epub Jul. 20, 2011.
Mosinger et al., Photofunctional polyurethane nanofabrics doped by zinc tetraphenylporphyrin and zinc phthalocyanine photosensitizers. J Fluoresc. Jul. 2009;19(4):705-13. doi: 10.1007/s10895-009-0464-0. Epub Jan. 29, 2009.
Zhang et al., DFT study on the influence of meso-phenyl substitution on the geometric, electronic structure and vibrational spectra of free base porphyrin. Chemical Physics. 2005;315:201-13.

* cited by examiner

Porphyrins

Chlorins

| Porphyrin # | Composition |
|---|---|
| 1 | H2TPP |
| 2 | MgTPP |
| 3 | ZnTPP |
| 4 | H2TMP |
| 5 | MgTMP |
| 6 | ZnTMP |
| 7 | H2TTP |
| 8 | (o-H2NPh)H2P |
| 9 | (ODC)H2P |
| 10 | C6F5-H2P |
| 11 | Protoporphyrin IX DME |
| 12 | Tetrabenzoporphine |
| 13 | "PdTCPH(CO2Me)Ph" |

Copper chlorin CuC-1

| Nominal Sample | %T Soret (413 nm) | Abs Soret (413 nm) | Abs $Q_1$ (538 nm) | ε ($M^{-1}cm^{-1}$) Soret (413 nm) | ε ($M^{-1}cm^{-1}$) $Q_1$ (538 nm) | $S/Q_1$ |
|---|---|---|---|---|---|---|
| **300 ppm** | 21% | 0.6722 | 0.0302 | 490k | 22k | 22.2 |
| **400 ppm** | 12% | 0.9111 | 0.0400 | 493k | 22k | 22.7 |
| **500 ppm** | 7% | 1.1582 | 0.0494 | 494k | 21k | 23.4 |
| **1000 ppm** | 0.3% | 2.5338 | 0.1099 | 544k | 24k | 23.1 |

| Nominal Sample | %T Soret (413 nm) | Abs Soret (413 nm) | Abs $Q_1$ (538 nm) | ε ($M^{-1}cm^{-1}$) Soret (413 nm) | ε ($M^{-1}cm^{-1}$) $Q_1$ (538 nm) | S/$Q_1$ |
|---|---|---|---|---|---|---|
| **300 ppm** | 19% | 0.7263 | 0.0325 | 522k | 23k | 22.4 |
| **400 ppm** | 10% | 0.9958 | 0.0439 | 524k | 23k | 22.7 |
| **500 ppm** | 6% | 1.1956 | 0.0528 | 509k | 23k | 22.6 |
| **1000 ppm** | 0.3% | 2.5049 | 0.1250 | 516k | 26k | 20.0 |

CONTACT LENS WITH OPTICAL PROPHYLAXIS

RELATED APPLICATION

This application claims priority under 35 U.S.C. § 119(e) to U.S. Provisional Application 63/275,159 filed Nov. 3, 2021, the entirety of which is incorporated herein by reference.

BACKGROUND

There exists a need for protecting the eye from damage by the most energetic photons in the blue and violet regions of the electromagnetic spectrum. Shehade et al. disclosed in U.S. Pat. No. 8,833,937 a retinal light management system that targets compromised patients by blocking light with wavelengths between 451 and 600 nanometers (nm). However, this approach does not account for substantial reduction in luminous transmission, interference with circadian rhythms, or color distortion.

Ishak disclosed, in U.S. Pat. No. 8,403,478, an ophthalmic lens with a reflective rugate filter that blocks visible blue light with wavelengths between 400 and 475 nm. This disclosure also did not account for interference with circadian rhythms, and the transmission profile of a rugate filter varies with both angle of incidence and polarization. The same inventor acknowledged color distortion and melatonin suppression by dye-loaded lenses in U.S. Pat. No. 10,610,472 obliquely but did not describe how to achieve retinal protection subject to these constraints.

Blue blocking has also been proposed for contact lenses. Newman et al. disclosed in US Application 2021/0132416 a contact lens that blocks at least some light between 400 and 500 nm. However, Newman fails to address luminous transmission, color distortion, or circadian rhythm interference. Moreover, the question of biocompatibility is not considered since, in paragraph [175] of the application " . . . any appropriate type of blocking agent may be used to block UV or blue light wavelengths."

Another approach to blue blocking contact lenses is described in U.S. Pat. No. 7,364,291, where alternate concentric circular rings of photochromic dyes are incorporated to block UV or blue light. As in Newman, broad wavelengths from 100 to 515 nm are described as being partially blocked but considerations of inevitable circadian, color distortion, or luminous transmission effects are not disclosed.

Yet another contact lens with blue blocking characteristics is disclosed by J. Y. Park in EP 3424688. This soft contact lens is manufactured with the dye 4-[(E)-phenyldiazenyl]phenyl-2-methacrylate or a like composition with substantial absorptivity above 500 nm, so it will interfere with circadian phase locking, color perception, and both scotopic and photopic luminous transmission.

A final example of blue-blocking lens disclosures is found by Y. C. Lai et al. in U.S. Pat. No. 7,276,544. They describe a process for manufacture of intraocular lenses with blue light absorption characteristics but as with Park's application there is no consideration of melatonin suppression, color distortion or luminous transmission attenuation.

Accordingly, there is a need for blue light-blocking lenses that come into intimate contact with the eye, either at the corneal surface as a contact lens or in the vitreous humor as an intraocular lens, that simultaneously minimize interference with circadian rhythms, luminous transmission during day and at night, and perceived colors.

SUMMARY

The present disclosure provides compounds, compositions, devices, and methods that protect optical device wearers from damage to retinal pigment epithelium. This protection is balanced by the unavoidable effects of reducing internal transmission of the device at toxic wavelengths on color distortion, circadian rhythm phase locking by melatonin suppression, luminous transmission, and discomfort glare.

In one aspect, provided is a compound of Formula (I):

(I)

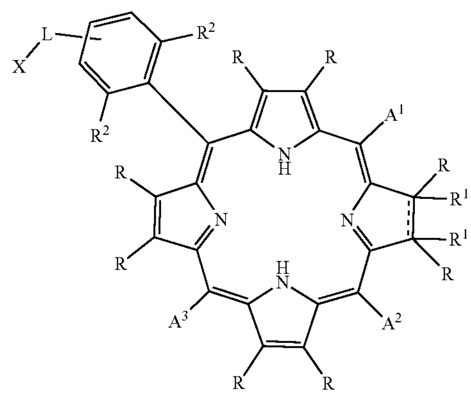

or a salt, or tautomer thereof, wherein the moieties and variables included in Formula (I) are as described herein.

In another aspect, provided is a metal chelate complex of the compound of Formula (I), such as a compound of Formula (II):

(II)

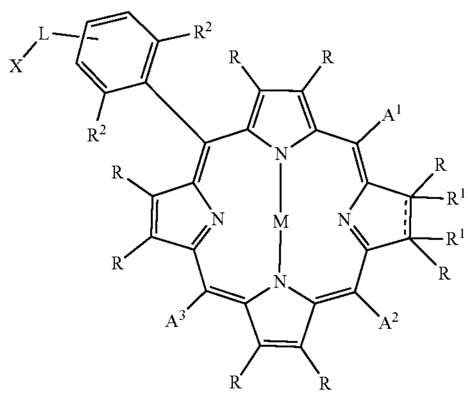

or a salt, or tautomer thereof, wherein the moieties and variables included in Formula (II) are as described herein.

In another aspect, provided is a composition comprising the compound of Formula (II) and a polymeric matrix.

In another aspect, provided is an optical device comprising a metalloporphyrin or metallochlorin compound, or a salt or tautomer thereof, covalently bound to a polymeric matrix.

In certain embodiments, the metalloporphyrin or metallochlorin compound of the device is of Formula (III):

(III)

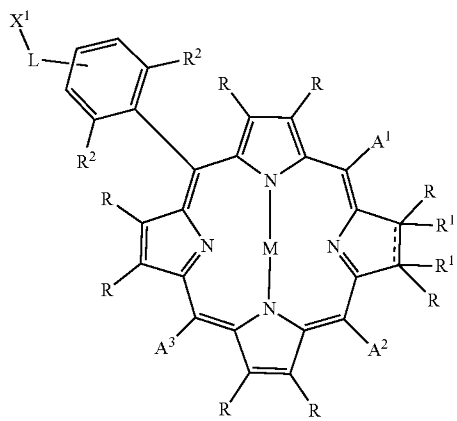

or a salt, or tautomer thereof, wherein the moieties and variables included in Formula (III) are as described herein. In certain embodiments, the optical device is a contact lens. In certain embodiments, the optical device is an intraocular lens. In certain embodiments, the optical device is an implantable contact lens.

In another aspect, provided is a method of protecting retinal pigment epithelium from blue light in a subject in need thereof, the method comprising applying an optical device of the disclosure to the eye of the subject.

In another aspect, provided is a method of preparing an optical device, the method comprising combining the compound of Formula (II) with a polymeric matrix. In certain embodiments, the method further comprises heating at a temperature above room temperature.

DETAILED DESCRIPTION

Definitions

Figure 1:
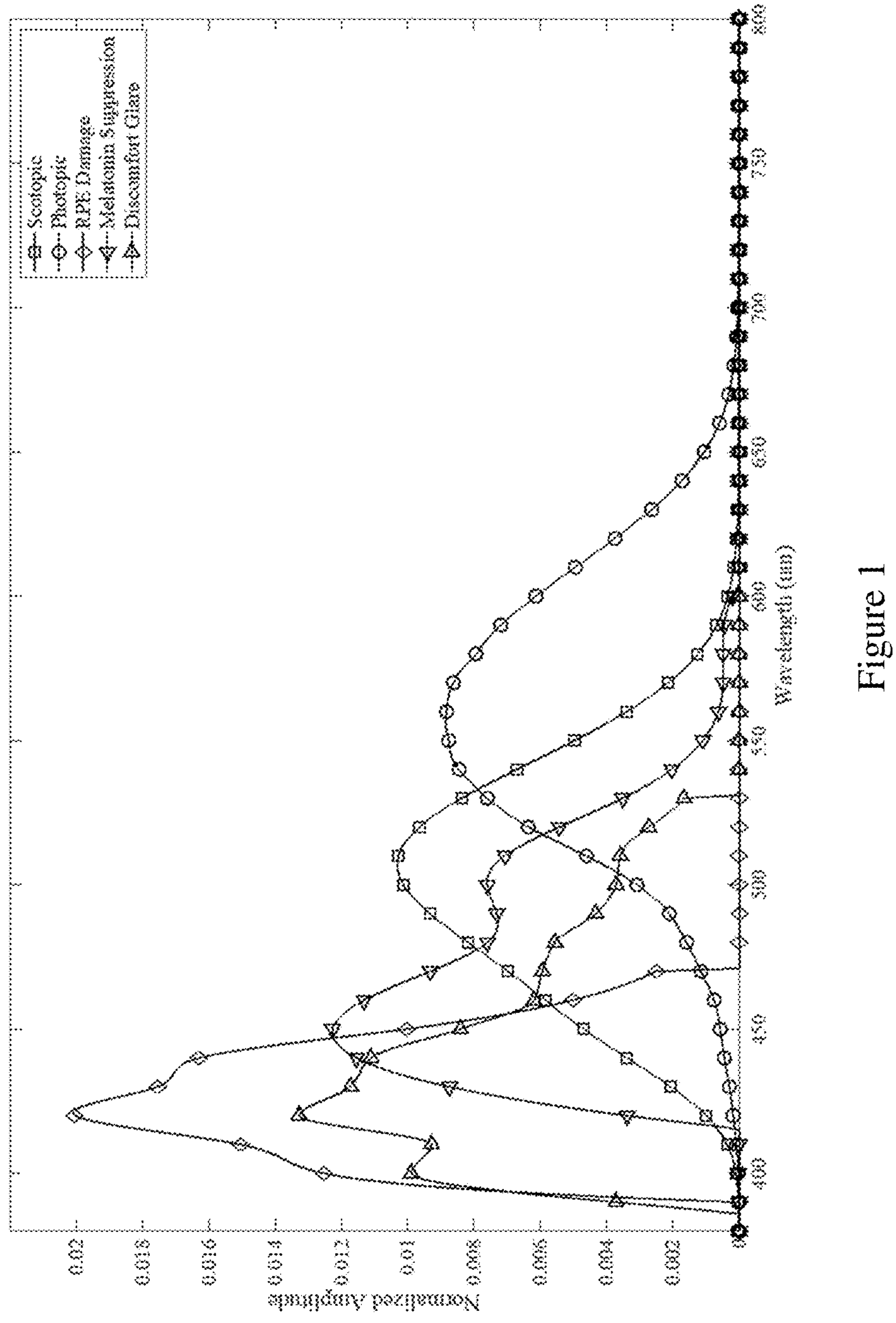
FIG. 1. Action spectra for scotopic and photopic sensitivities, damage to retinal pigment epithelia, suppression of melatonin synthesis, and discomfort glare.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, ∿∿ is a single bond where the stereochemistry of the moieties immediately attached thereto is not specified, – – – is absent or a single bond, and ═══ or ═══ is a single or double bond.

Unless otherwise provided, formulae and structures depicted herein include compounds that do not include isotopically enriched atoms, and also include compounds that include isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

When a range of values ("range") is listed, it encompasses each value and sub-range within the range. A range is inclusive of the values at the two ends of the range unless otherwise provided. For example "$C_{1-6}$ alkyl" encompasses, $C_1$, $C_2$, $C_3$, $C_4$, $C_5$, $C_6$, $C_{1-6}$, $C_{1-5}$, $C_{1-4}$, $C_{1-3}$, $C_1$-2, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tert-amyl), and hexyl ($C_6$) (e.g., n-hexyl). Additional examples of alkyl groups include n-heptyl ($C_7$), n-octyl ($C_8$), n-dodecyl ($C_{12}$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-12}$ alkyl (such as unsubstituted $C_{1-6}$ alkyl, e.g., $-CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-12}$ alkyl (such as substituted $C_{1-6}$ alkyl, e.g., $-CH_2F$, $-CHF_2$, $-CF_3$, $-CH_2CH_2F$, $-CH_2CHF_2$, $-CH_2CF_3$, or benzyl (Bn)).

The term "heteroalkyl" refers to an alkyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$ alkyl"). In certain embodiments, a heteroalkyl group refers to a saturated group having from 1 to 12 carbon atoms and 1 or more heteroatoms within the parent chain ("hetero$C_{1-12}$ alkyl"). In some embodiments, a heteroalkyl group is a saturated group having 1 to 11 carbon atoms and 1 or more heteroatoms within the parent chain ("hetero$C_{1-11}$ alkyl"). In some embodiments, a heteroalkyl group is a saturated group having 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-5}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-12}$ alkyl. In certain embodiments, the heteroalkyl group is a substituted hetero$C_{1-12}$ alkyl.

The term "alkenyl" refers to a radical of a straight-chain or branched hydrocarbon group having from 1 to 20 carbon atoms and one or more carbon-carbon double bonds (e.g., 1, 2, 3, or 4 double bonds). In some embodiments, an alkenyl group has 1 to 20 carbon atoms ("$C_{1-20}$ alkenyl"). In some embodiments, an alkenyl group has 1 to 12 carbon atoms ("$C_{1-12}$ alkenyl"). In some embodiments, an alkenyl group has 1 to 11 carbon atoms ("$C_{1-11}$ alkenyl"). In some embodiments, an alkenyl group has 1 to 10 carbon atoms ("$C_{1-10}$ alkenyl"). In some embodiments, an alkenyl group has 1 to 9 carbon atoms ("$C_{1-9}$ alkenyl"). In some embodiments, an alkenyl group has 1 to 8 carbon atoms ("$C_{1-5}$ alkenyl"). In some embodiments, an alkenyl group has 1 to 7 carbon atoms ("$C_{1-7}$ alkenyl"). In some embodiments, an alkenyl group has 1 to 6 carbon atoms ("$C_{1-6}$ alkenyl"). In some embodiments, an alkenyl group has 1 to 5 carbon atoms ("$C_{1-5}$ alkenyl"). In some embodiments, an alkenyl group has 1 to 4 carbon atoms ("$C_{1-4}$ alkenyl"). In some embodiments, an alkenyl group has 1 to 3 carbon atoms ("$C_{1-3}$ alkenyl"). In some embodiments, an alkenyl group has 1 to 2 carbon atoms ("$C_{1-2}$ alkenyl"). In some embodiments, an alkenyl group has 1 carbon atom ("$C_1$ alkenyl"). The one or more carbon-carbon double bonds can be internal (such as in 2-butenyl) or terminal (such as in 1-butenyl). Examples of $C_{1-4}$ alkenyl groups include methylidenyl ($C_1$), ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{1-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{1-20}$ alkenyl. In certain embodiments, the alkenyl group is a substituted $C_{1-20}$ alkenyl. In an alkenyl group, a C═C double bond for which the stereochemistry is not specified (e.g., —CH═CHCH$_3$ or

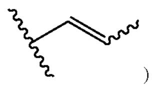

)

may be in the (E)- or (Z)-configuration.

The term "alkynyl" refers to a radical of a straight-chain or branched hydrocarbon group having from 1 to 20 carbon atoms and one or more carbon-carbon triple bonds (e.g., 1, 2, 3, or 4 triple bonds) ("$C_{1-20}$ alkynyl"). In some embodiments, an alkynyl group has 1 to 10 carbon atoms ("$C_{1-10}$ alkynyl"). In some embodiments, an alkynyl group has 1 to 9 carbon atoms ("$C_{1-9}$ alkynyl"). In some embodiments, an alkynyl group has 1 to 8 carbon atoms ("$C_{1-5}$ alkynyl"). In some embodiments, an alkynyl group has 1 to 7 carbon atoms ("$C_{1-7}$ alkynyl"). In some embodiments, an alkynyl group has 1 to 6 carbon atoms ("$C_{1-6}$ alkynyl"). In some embodiments, an alkynyl group has 1 to 5 carbon atoms ("$C_{1-5}$ alkynyl"). In some embodiments, an alkynyl group has 1 to 4 carbon atoms ("$C_{1-4}$ alkynyl"). In some embodiments, an alkynyl group has 1 to 3 carbon atoms ("$C_{1-3}$ alkynyl"). In some embodiments, an alkynyl group has 1 to 2 carbon atoms ("$C_{1-2}$ alkynyl"). In some embodiments, an alkynyl group has 1 carbon atom ("$C_1$ alkynyl"). The one or more carbon-carbon triple bonds can be internal (such as in 2-butynyl) or terminal (such as in 1-butynyl). Examples of $C_{1-4}$ alkynyl groups include, without limitation, methylidynyl ($C_1$), ethynyl ($C_2$), 1-propynyl ($C_3$), 2-propynyl ($C_3$), 1-butynyl ($C_4$), 2-butynyl ($C_4$), and the like. Examples of $C_{1-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{1-20}$ alkynyl. In certain embodiments, the alkynyl group is a substituted $C_{1-20}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 14 ring carbon atoms ("$C_{3-14}$ carbocyclyl"). In some embodiments, a carbocyclyl group has 3 to 13 ring carbon atoms ("$C_{3-13}$ carbocyclyl"). In some embodiments, a carbocyclyl group has 3 to 12 ring carbon atoms ("$C_{3-12}$ carbocyclyl"). In some embodiments, a carbocyclyl group has 3 to 11 ring carbon atoms ("$C_{3-11}$ carbocyclyl"). In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. Exemplary $C_{3-8}$ carbocyclyl groups include the aforementioned $C_{3-10}$ carbocyclyl groups as well as cycloundecyl ($C_{11}$), spiro[5.5]undecanyl ($C_{11}$), cyclododecyl ($C_{12}$), cyclododecenyl ($C_{12}$), cyclotridecane ($C_{13}$), cyclotetradecane ($C_{14}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl. In certain embodiments, the carbocyclyl includes 0, 1, or 2 C═C double bonds in the carbocyclic ring system, as valency permits.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include azirdinyl, oxiranyl, and thiiranyl. Exemplary 4-membered heterocyclyl groups containing 1 heteroatom include azetidinyl, oxetanyl, and thietanyl. Exemplary 5-membered heterocyclyl groups containing 1 heteroatom include tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include dioxolanyl, oxathiolanyl and dithiolanyl. Exemplary 5-membered heterocyclyl groups containing 3 heteroatoms include triazolinyl, oxadiazolinyl, and thiadiazolinyl. Exemplary 6-membered heterocyclyl groups containing 1 heteroatom include piperidinyl, tetrahydropyranyl, dihydropyridinyl, and thianyl. Exemplary 6-membered heterocyclyl groups containing 2 heteroatoms include piperazinyl, morpholinyl, dithianyl, and dioxanyl. Exemplary 6-membered heterocyclyl groups containing 3 heteroatoms include triazinyl. Exemplary 7-membered heterocyclyl groups containing 1 heteroatom include azepanyl, oxepanyl and thiepanyl. Exemplary 8-membered heterocyclyl groups containing 1 heteroatom include azocanyl, oxecanyl and thiocanyl. Exemplary bicyclic heterocyclyl groups include indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 $\pi$ electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 $\pi$ electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include pyrrolyl, furanyl, and thiophenyl. Exemplary 5-membered heteroaryl groups containing 2 heteroatoms include imidazolyl, pyrazolyl, oxazolyl, isoxazolyl, thiazolyl, and isothiazolyl. Exemplary 5-membered heteroaryl groups containing 3 heteroatoms include triazolyl, oxadiazolyl, and thiadiazolyl. Exemplary 5-membered heteroaryl groups containing 4 heteroatoms include tetrazolyl. Exemplary 6-membered heteroaryl groups containing 1 heteroatom include pyridinyl.

Exemplary 6-membered heteroaryl groups containing 2 heteroatoms include pyridazinyl, pyrimidinyl, and pyrazinyl. Exemplary 6-membered heteroaryl groups containing 3 or 4 heteroatoms include triazinyl and tetrazinyl, respectively. Exemplary 7-membered heteroaryl groups containing 1 heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl. Exemplary tricyclic heteroaryl groups include phenanthridinyl, dibenzofuranyl, carbazolyl, acridinyl, phenothiazinyl, phenoxazinyl, and phenazinyl.

The term "unsaturated bond" refers to a double or triple bond.

The term "unsaturated" or "partially unsaturated" refers to a moiety that includes at least one double or triple bond.

The term "saturated" or "fully saturated" refers to a moiety that does not contain a double or triple bond, e.g., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not limited in any manner by the exemplary substituents described herein.

Exemplary carbon atom substituents include halogen, —CN, —$NO_2$, —$N_3$, —$SO_2H$, —$SO_3H$, —OH, —OR—, —$ON(R^{bb})_2$, —$N(R^{bb})_2$, —$N(R^{bb})_3{}^+X^-$, —$N(OR^{cc})R^{bb}$, —SH, —SR—, —$SSR^{cc}$, —C(═O)$R^{aa}$, —$CO_2H$, —CHO, —$C(OR^{cc})_2$, —$CO_2R^{aa}$, —OC(═O)$R^{aa}$, —$OCO_2R^{aa}$, —C(═O)$N(R^{bb})_2$, —OC(═O)$N(R^{bb})_2$, —$NR^{bb}$C(═O)$R^{aa}$, —$NR^{bb}CO_2R^{aa}$, —$NR^{bb}$C(═O)$N(R^{bb})_2$, —C(═$NR^{bb}$)$R^{aa}$, —C(═$NR^{bb}$)$OR^{aa}$, —OC(═$NR^{bb}$)$R^{aa}$, —OC(═$NR^{bb}$)$OR^{aa}$, —C(═$NR^{bb}$)$N(R^{bb})_2$, —OC(═$NR^{bb}$)$N(R^{bb})_2$, —$NR^{bb}$C(═$NR^{bb}$)$N(R^{bb})_2$, —C(═O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(═O)$R^{aa}$, —OS(═O)$R^{aa}$, —$Si(R^{aa})_3$, —$OSi(R^{aa})_3$—C(═S)$N(R^{bb})_2$, —C(═O)$SR^{aa}$, —C(═S)$SR^{aa}$, —SC(═S)$SR^{aa}$, —SC(═O)$SR^{aa}$, —OC(═O)$SR^{aa}$, —SC(═O)$OR^{aa}$, —SC(═O)$R^{aa}$, —P(═O)$(R^{aa})_2$, —P(═O)$(OR^{cc})_2$, —OP(═O)$(R^{aa})_2$, —OP(═O)$(OR^{cc})_2$, —P(═O)$(N(R^bb)_2)_2$, —OP(═O)$(N(R^{bb})_2)_2$, —$NR^{bb}$P(═O)$(R^{aa})_2$, —$NR^{bb}$P(═O)$(OR^{cc})_2$, —$NR^{bb}$P(═O)$(N(R^{bb})_2)_2$, —$P(R^{cc})_2$, —$P(OR^{cc})_2$, —$P(R^{cc})_3{}^+X^-$, —$P(OR^{cc})_3{}^+X^-$, —$P(R^{cc})_4$, —$P(OR^{cc})_4$, —$OP(R^{cc})_2$, —$OP(R^{cc})_3{}^+X^-$, —$OP(OR^{cc})_2$, —$OP(OR^{cc})_3{}^+X^-$, —$OP(R^{cc})_4$, —$OP(OR^{cc})_4$, —$B(R^{aa})_2$, —$B(OR^{cc})_2$, —$BR^{aa}(OR^{cc})$, $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion; or two geminal hydrogens on a carbon atom are replaced with the group ═O, ═S, ═$NN(R^{bb})_2$, ═$NNR^{bb}$C(═O)$R^{aa}$, ═$NNR^{bb}$C(═O)$OR^{aa}$, ═$NNR^{bb}$S(═O)$_2R^{aa}$, ═$NR^{bb}$, or ═$NOR^{cc}$; wherein:

each instance of $R^{aa}$ is, independently, selected from $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —C(═O)$R^{aa}$, —C(═O)$N(R^{cc})_2$, —$CO_2R^{aa}$, —$SO_2R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, —P(═O)$(R^{aa})_2$, —P(═O)$(OR^{cc})_2$, —P(═O)$(N(R^{cc})_2)_2$, $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{cc}$, —$ON(R^{ff})_2$, —$N(R^{ff})_2$, —$N(R^{ff})_3{}^+X^-$, —$N(OR^{ee})R^{ff}$, —SH, —$SR^{ee}$, —$SSR^{ee}$, —C(═O)$R^{ee}$, —$CO_2H$, —$CO_2R^{ee}$, —OC(═O)$R^{ee}$, —$OCO_2R^{ee}$, —C(═O)$N(R^{ff})_2$, —OC(═O)$N(R^{ff})_2$, —$NR^{ff}$C(═O)$R^{ee}$, —$NR^{ff}CO_2R^{ee}$, —$NR^{ff}$C(═O)$N(R^{ff})_2$, —C(═$NR^{ff}$)$OR^{ee}$, —OC(═$NR^{ff}$)$R^{ee}$, —OC(═$NR^{ff}$)$OR^{ee}$, —C(═$NR^{ff}$)$N(R^{ff})_2$, —OC(═$NR^{ff}$)$N(R^{ff})_2$, —$NR^{ff}$C(═$NR^{ff}$)$N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(═O)$R^{ee}$, —$Si(R^{ee})_3$, —$OSi(R^{ee})_3$, —C(═S)$N(R^{ff})_2$, —C(═O)$SR^{ee}$, —C(═S)$SR^{ee}$, —SC(═S)$SR^{ee}$, —P(═O)$(OR^{ee})_2$, —P(═O)$(R^{ee})_2$, —OP(═O)$(R^{ee})_2$, —OP(═O)$(OR^{ee})_2$, $C_{1-10}$ alkyl, $C_{1-10}$ perhaloalkyl, $C_{1-10}$ alkenyl, $C_{1-10}$ alkynyl, hetero$C_{1-10}$alkyl, hetero$C_{1-10}$alkenyl, hetero$C_{1-10}$alkynyl, $C_{3-10}$ carbocyclyl, 3-10 membered heterocyclyl, $C_{6-10}$ aryl, and 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{99}$ groups, or two geminal $R^{dd}$ substituents are joined to form ═O or ═S; wherein $X^-$ is a counterion;

each instance of $R^{ee}$ is, independently, selected from $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, 3-10 membered heterocyclyl, $C_{6-10}$ aryl, and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3{}^+X^-$, —$NH(C_{1-6}$ alkyl$)_2{}^+X^-$, —$NH_2(C_{1-6}$ alkyl$)^+X^-$, —$NH_3{}^+X^-$, —$N(OC_{1-6}$ alkyl$)(C_{1-6}$ alkyl), —N(OH)($C_{1-6}$ alkyl), —NH(OH), —SH, —$SC_{1-6}$ alkyl, —SS($C_{1-6}$ alkyl), —C(═O)($C_{1-6}$ alkyl), —$CO_2H$, —$CO_2(C_{1-6}$ alkyl), —OC(═O)($C_{1-6}$ alkyl), —$OCO_2(C_{1-6}$ alkyl), —C(═O)$NH_2$, —C(═O)$N(C_{1-6}$ alkyl$)_2$, —OC(═O)NH($C_{1-6}$ alkyl), —NHC(═O)($C_{1-6}$ alkyl), —N($C_{1-6}$ alkyl)C(═O)($C_{1-6}$ alkyl), —$NHCO_2$($C_{1-6}$ alkyl), —NHC(═O)$N(C_{1-6}$ alkyl$)_2$, —NHC (=O)NH($C_{1-6}$ alkyl), —NHC(=O)$NH_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(=NH)$NH_2$, —$NHSO_2$($C_{1-6}$ alkyl), —$SO_2$N($C_{1-6}$ alkyl)$_2$, —$SO_2$NH($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$, —C(=S)N($C_{1-6}$ alkyl)$_2$, C(=S)NH($C_{1-6}$ alkyl), C(=S)$NH_2$, —C(=O)S($C_{1-6}$ alkyl), —C(=S)$SC_{1-6}$ alkyl, —SC(=S)$SC_{1-6}$ alkyl, —P(=O)($OC_{1-6}$ alkyl)$_2$, —P(=O)($C_{1-6}$ alkyl)$_2$, —OP(=O)($C_{1-6}$ alkyl)$_2$, —OP(=O)($OC_{1-6}$ alkyl)$_2$, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, $C_{6-10}$ aryl, 3-10 membered heterocyclyl, or 5-10 membered heteroaryl; or two geminal $R^{gg}$ substituents can be joined to form =O or =S; and each $X^-$ is a counterion.

The term "halo" or "halogen" refers to fluorine (fluoro, —F), chlorine (chloro, —Cl), bromine (bromo, —Br), or iodine (iodo, —I).

The term "acyl" refers to a group having the general formula —C(=O)$R^{X1}$, —C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, and —C(=S)S($R^{X1}$), —C(=N$R^{X1}$)$R^{X1}$, —C(=N$R^{X1}$)O$R^{X1}$, —C(=N$R^{X1}$)S$R^{X1}$, and —C(=N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas.

Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —$CO_2R^{aa}$, —$SO_2R^{aa}$, —C(=N$R^{bb}$)$R^{aa}$, —C(=N$R^{cc}$)O$R^{aa}$, —C(=N$R^{cc}$)N($R^{cc}$)$_2$, —$SO_2$N($R^{cc}$)$_2$, —$SO_2R^{cc}$, —$SO_2OR^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein.

In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —$CO_2R^{aa}$, —$SO_2R^{aa}$, —C(=N$R^{cc}$)$R^{aa}$, —C(=N$R^{cc}$)O$R^{aa}$, —C(=N$R^{cc}$)N($R^{cc}$)$_2$, —$SO_2$N($R^{cc}$)$_2$, —$SO_2R^{aa}$, —$SO_2OR^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $—S(=O)_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 0-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

A "counterion" or "anionic counterion" is a negatively charged group associated with a positively charged group in order to maintain electronic neutrality. An anionic counterion may be monovalent (e.g., including one formal negative charge). An anionic counterion may also be multivalent (e.g., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF^6$, $B[3,5-(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, the term "polymerizable group" refers to a functional group that can undergo chain growth polymerization involving free radicals. Non-limiting examples of polymerizable groups include a (meth)acryloyl

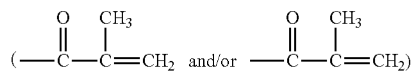

group, an allyl group, a vinyl group, a styrenyl group, a vinylaminocarbonyl group

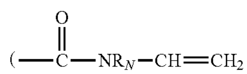

in which $R_N$ is H or $C_1$-$C_6$ alkyl), a vinyloxycarbonylamino group

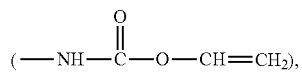

a vinyloxycarbonyloxy group

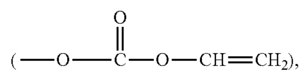

a vinyl sulfonyl group, a norbornyl group, an alkynyl group, an alkenyl group, or a cycloalkenyl group. Preferably, a polymerizable group is or comprises a (meth)acryloyl

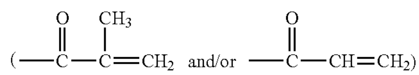

group, an allyl group, a vinyl group, a styrenyl group, a vinylaminocarbonyl group

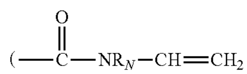

in which $R_N$ is H or $C_1$-$C_6$ alkyl), a vinyloxycarbonylamino group

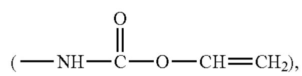

a vinyloxycarbonyloxy group

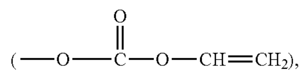

a vinyl sulfonyl group, or a norbornyl group.

Various conditions for effecting polymerization (e.g., free radical polymerization) are known in the art. Polymerization can be effected, for example, actinically (i.e., by use of an irradiation with UV or a visible light), or thermally (i.e., by heating) in the presence of a free-radical initiator.

The term "transition metal" refers to elements that are in the d-block and f-block of the Periodic Chart of the Elements, which may exhibit a variety of oxidation states, and which may form numerous complex ions. The term "d-block" refers to those elements that have electrons filling the 3d, 4d, 5d, and 6d orbitals, and the term "f-block" refers to those elements (including lanthanides and the actinides) that have electrons filling the 4f and 5f orbitals. Exemplary transition metals include palladium, nickel, cobalt, copper, platinum, silver, manganese, zinc, iridium, rhodium, iron, and ruthenium. The term "transition metal" also includes alloys, metal/metal composites, metal ceramic composites, and metal polymer composites, as well as other metal composites.

As used herein, the term "salt" refers to any and all salts. Salts include ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids, such as hydrochloric acid, hydrobromic acid, phosphoric acid, sulfuric acid, and perchloric acid, or with organic acids, such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, hippurate, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn, Ingold, Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of embodiments of the present disclosure. The materials, methods, and examples disclosed herein are illustrative only and not intended to be limiting.

The term "about X," where X is a number or percentage, refers to a number or percentage that is between 99.5% and 100.5%, between 99% and 101%, between 98% and 102%, between 97% and 103%, between 96% and 104%, between 95% and 105%, between 92% and 108%, or between 90% and 110%, inclusive, of X.

The terms "first," "second," "third," and the like, as used herein, do not denote any order, quantity, or importance, but rather are used to distinguish one element from another.

Use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

Compound and Device Design

The present disclosure describes methods, compounds, and lens devices that mitigate damage to retinal epithelial cells while balancing changes to luminous transmission, discomfort glare, color distortion, and disruption of circadian rhythms and that simultaneously comply with constraints based on chemical stability during manufacture, photobleaching or oxidation, and contact with living tissues.

Optical Transmission

The energy of photons absorbed by retinal pigments is inversely proportional to their wavelength. The primary mechanism of retinal damage by blue and violet light is known to involve absorption by pigments such as lipofuscin that trigger production of reactive oxygen species. Careful measurements of these processes have resulted in action spectra for the impact of different wavelengths of light on damage to retinal pigment epithelial (RPE) cells, as described for example in Marie et al. Cell Death and Disease (2018) 9:287 or Hammond et al. in Clinical Ophthalmology 2019:13 2427-2438, and shown in FIG. 1. The contribution to retinal damage for incident light with a given spectrum is quantified by integrating the product of the action spectrum times the incident spectrum over visible wavelengths from 380 to 800 nm.

The sensitivity of the human visual system is also characterized by wavelength dependencies that vary with the overall scene luminance. The sensitivity functions for night (scotopic) visual acuity are shifted to the blue compared with those for daylight (photopic) vision as shown in FIG. 1. Intermediate (mesopic) luminance visual acuity is intermediate between these sensitivity spectra and is not shown because of its complex dependence on other contextual factors.

Discomfort glare is also disproportionately perceived by light of shorter visible wavelengths, as shown in FIG. 1 and described in detail in U.S. Pat. Nos. 10,545,264 and 10,935,709 and Fekete et al. *Ophthal. Physiol. Opt.* 2006 26: 313-317. The spectral variation of discomfort glare is also reproduced in FIG. 1.

Another factor that requires consideration when filtering visible light is the mechanism by which blue light suppresses melatonin synthesis. The fading of blue light provides a phase locking signal for circadian rhythms with explicit wavelength variation defined in the action spectrum reported by Brainard et al. in The Journal of Neuroscience, 21(16), 6405-12, 15 Aug. 2001.

Internal absorption is also known to influence the perceived color of objects, so consideration of this effect, though slightly more complex, is also important. Color distortion is most conveniently calculated using the L*a*b* uniform color space in which framework one unit of length corresponds to a 'just noticeable difference' in color based on psychophysical measurements with human observers and controlled illumination. The full range of colors visible to humans is spanned by the 1269 Munsell color tiles as described, for example, by Romney and Indow, Color research and application, 28(3), 182-96, 2003. The color shift in uniform color space can be calculated based on the displacement in L*a*b* for each of the color tiles when internal absorption by dye is incorporated. This approach is amply described in the prior art, for example in U.S. Pat. No. 9,063,349. Incorporating the shift in color space can be accomplished by using a statistical moment of the distribution of L*a*b* shifts such as the mean, median, or variance, or a simple sum of all of the displacements, as illustrated in the embodiments below.

Chemical Stability Factors

Manufacturing processes for contact and intraocular lenses require varied chemical conditions. First, internal transmission is limited by the range of products of lens thickness, dye concentration, and extinction coefficient that can be achieved with the required solvents and resins.

Second, the dye must be chemically stable under the reaction conditions required for their manufacture. These include interaction with reactive species present during thermal or photochemical polymerization, elevated pressures and temperatures encountered in injection molding, and exposure to oxygen.

Third, the final product must be biocompatible; the dye material is preferably neither toxic nor irritating and is incorporated into the product by covalent bonds.

Finally, the dye incorporated into the lens matrix must be photostable. Contact lenses, which are exposed to ambient light, air, and fluid on the corneal surface, must resist photooxidative degradation for the duration of its use. Intraocular lenses similarly must withstand light that penetrates the iris and remain compatible with the vitreous humor, in this case for a much longer time than for a contact lens.

Chemical Families: Porphyrins and Chlorins

Figure 2:
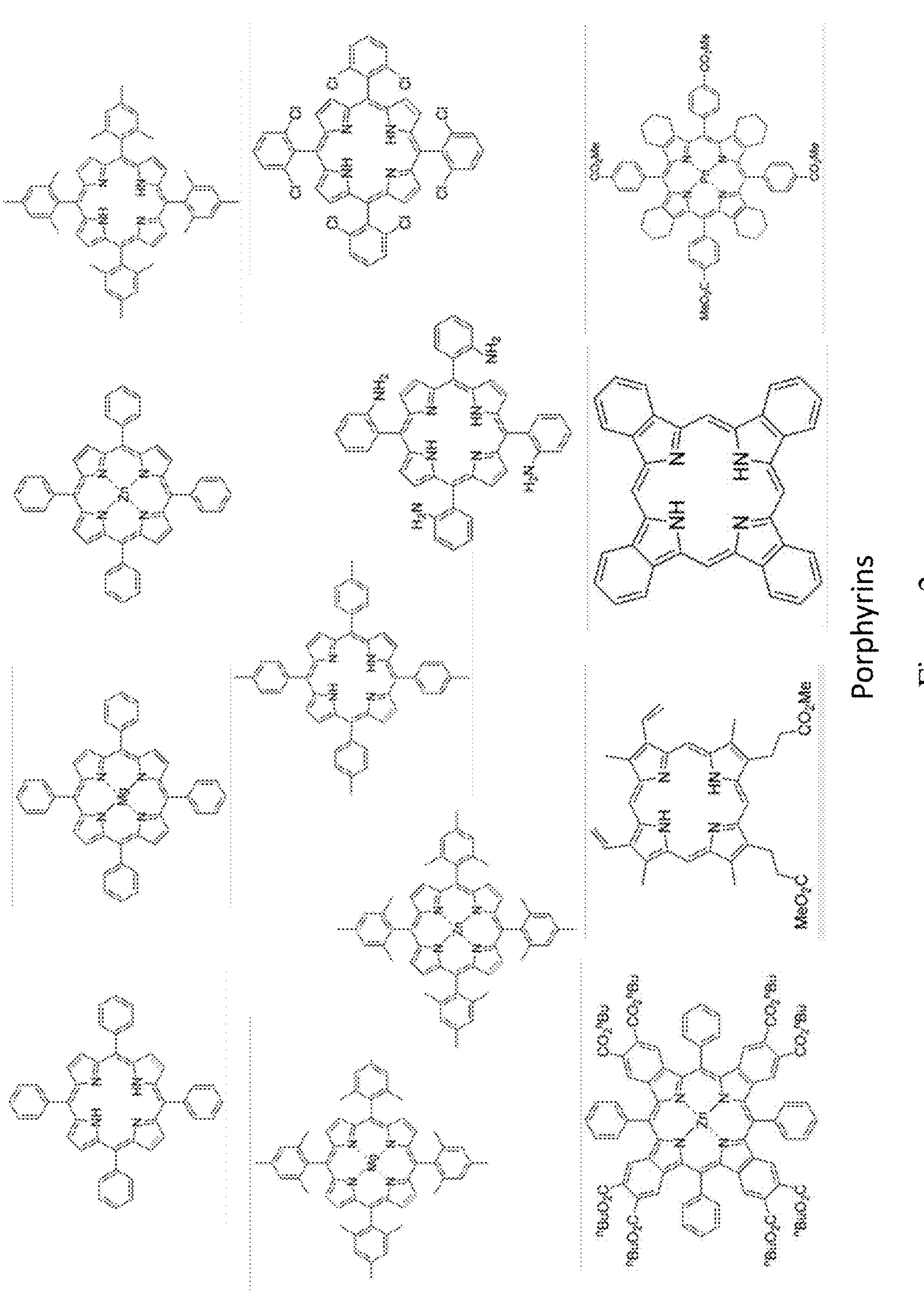
FIG. 2. Chemical structures of porphyrin chromophores. Top row, left to right: dihydro tetraphenylporphyrin ($H_2TPP$), magnesium tetraphenylporphyrin (MgTPP), zinc tetraphenylporphyrin (MgTPP), dihydro tetramesitylporphyrin ($H_2TMP$): Middle row, left to right: magnesium tetramesitylporphyrin (MgTMP), zinc tetramesitylporphyrin (ZnTMP), dihydro tetratolylporphyrin ($H_2TTP$), o-aminophenyldihydroporphyrin ((o-$H_2NPh$)$H_2P$), o-dichlorodihydroporphyrin ((ODC)$H_2P$); Third row, left to right: TBP-meso-tetraphenyl-beta-octa(COOMe)-Z, protoporphyrin IX dimethyl ester, tetrabenzoporphine, palladium tetracyclohexyltetra(p-benzoate)porphyrin (PdTCPH($CO_2Me$)Ph)
Figure 3:
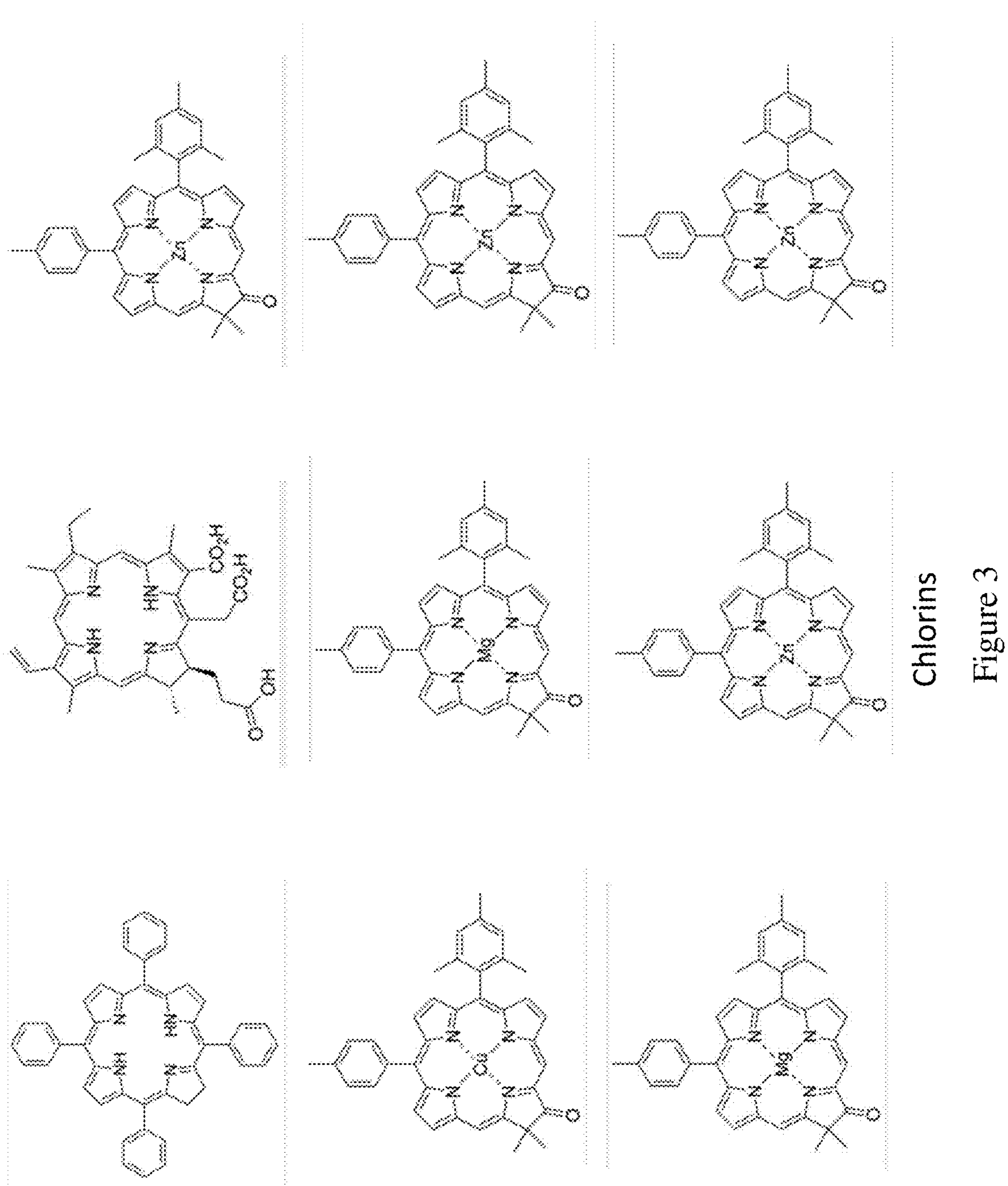
FIG. 3. Chemical structures of chlorin chromophores. Top row, left to right: meso-tetraphenylchlorin ($H_2TPC$), chlorin e6, 17,18-dihydro-10-mesityl-18,18-dimethyl-5-(4-methylphenyl)porphyrin ($H_2C$-1); Middle row, left to right: Copper(II)-17,18-dihydro-10-mesityl-18,18-dimethyl-5-(4-methylphenyl)porphyrin (CuC-1), Zinc(II)-17,18-dihydro-10-mesityl-18,18-dimethyl-5-(4-methylphenyl)porphyrin (ZnC-1), 17,18-dihydro-18,18-dimethyl-5-(4-methylphenyl)-10-mesityl-17-oxoporphyrin ($H_2$COxo-1); Third row, left to right: Magnesium(II)-17,18-dihydro-18,18-dimethyl-5-(4-methylphenyl)-10-mesityl-17-oxoporphyrin (MgCOxo-1), Copper(II)-17,18-dihydro-18,18-dimethyl-5-(4-methylphenyl)-10-mesityl-17-oxoporphyrin (CuCOxo-1), Zinc(II)-17,18-dihydro-18,18-dimethyl-5-(4-methylphenyl)-10-mesityl-17-oxoporphyrin (ZnCOxo-1).

The following embodiments describe the method of the disclosure for compositions with porphyrin or chlorin ring configurations, representative examples of which are shown in FIGS. 2 and 3.

The term "porphyrin" refers to a group of heterocyclic macrocycle organic compounds, composed of four modified pyrrole subunits interconnected at their a carbon atoms via methine bridges (=CH—). With a total of 26 π-electrons, of which 18 π-electrons form a planar, continuous cycle, the porphyrin ring structure is often described as aromatic.

The term "chlorin" refers to a group of compounds related to the porphyrins. Chlorins are reduced derivatives of porphyrins (i.e., dihydroporphyrin) wherein one pyrrole has been converted to a pyrroline.

These materials have planar, conjugated p-orbitals on a rigid ring that may also include a metal with d-orbitals that interact with the pi cloud of the heteroatomic ring system. These features provide the basis for strong optical absorption in the blue and violet spectral regions. However, other dye materials with the requisite extinction coefficient, solubility, and chemical stability may also be employed according to this method.

Design Embodiments

Figure 4A:
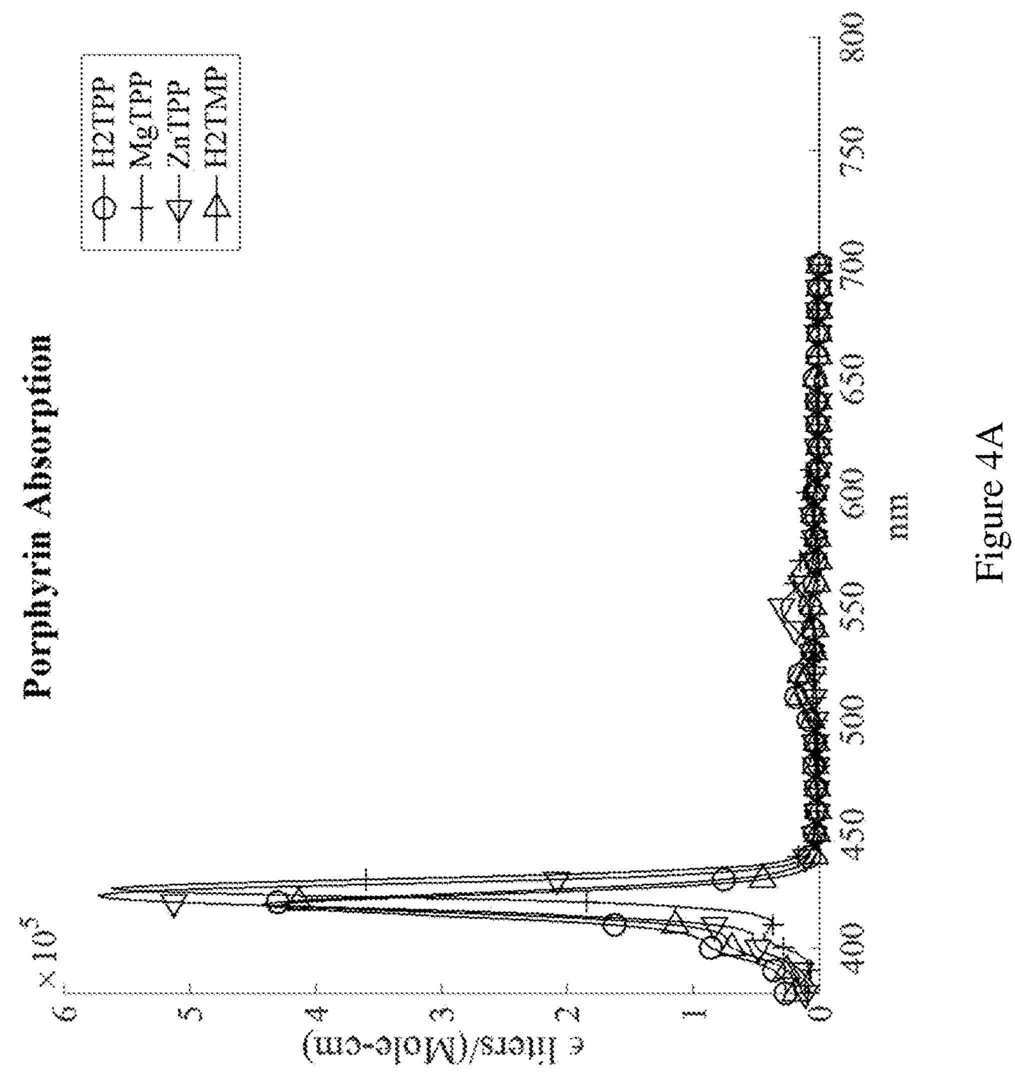
FIG. 4A-C. Absorption spectra of the porphyrin chromophores from FIG. 2.
Figure 4B:
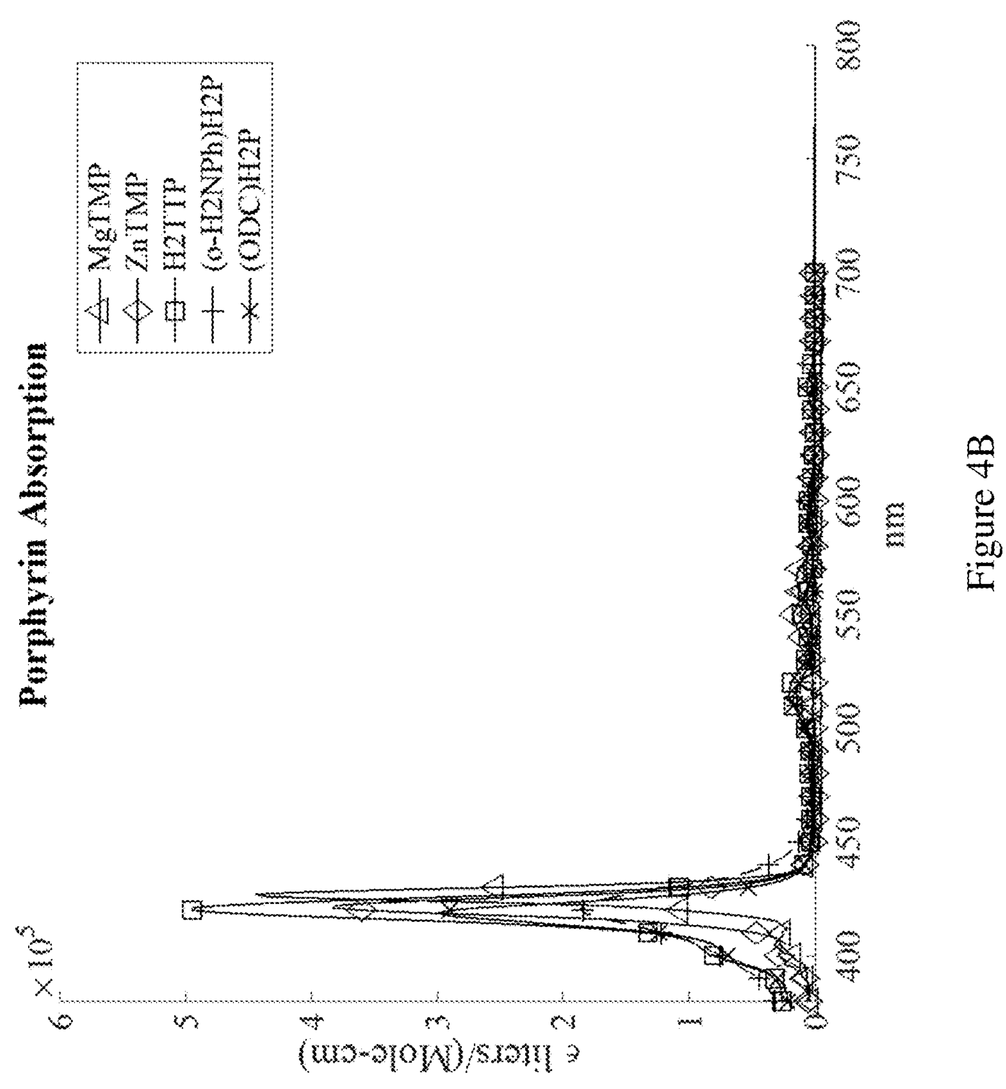
Figure 4C:
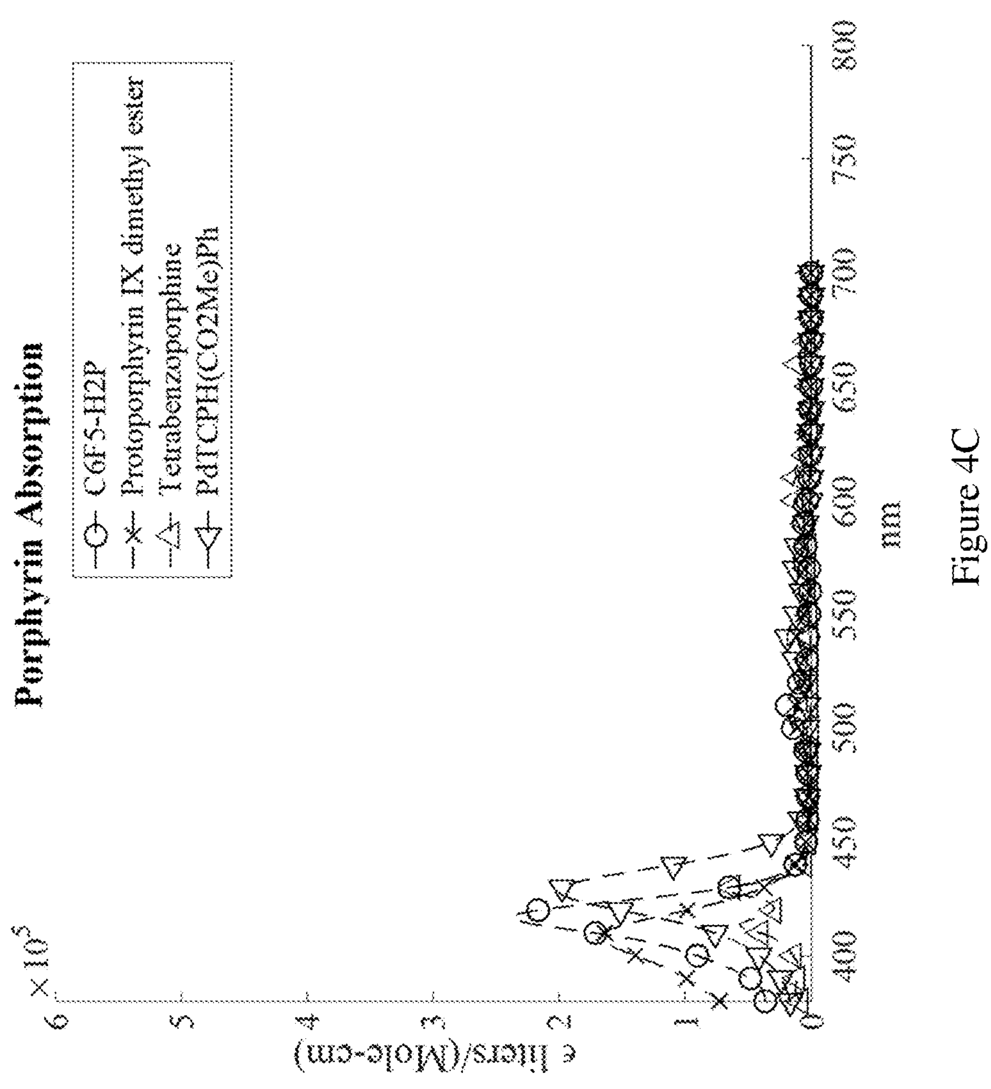
Figure 5:
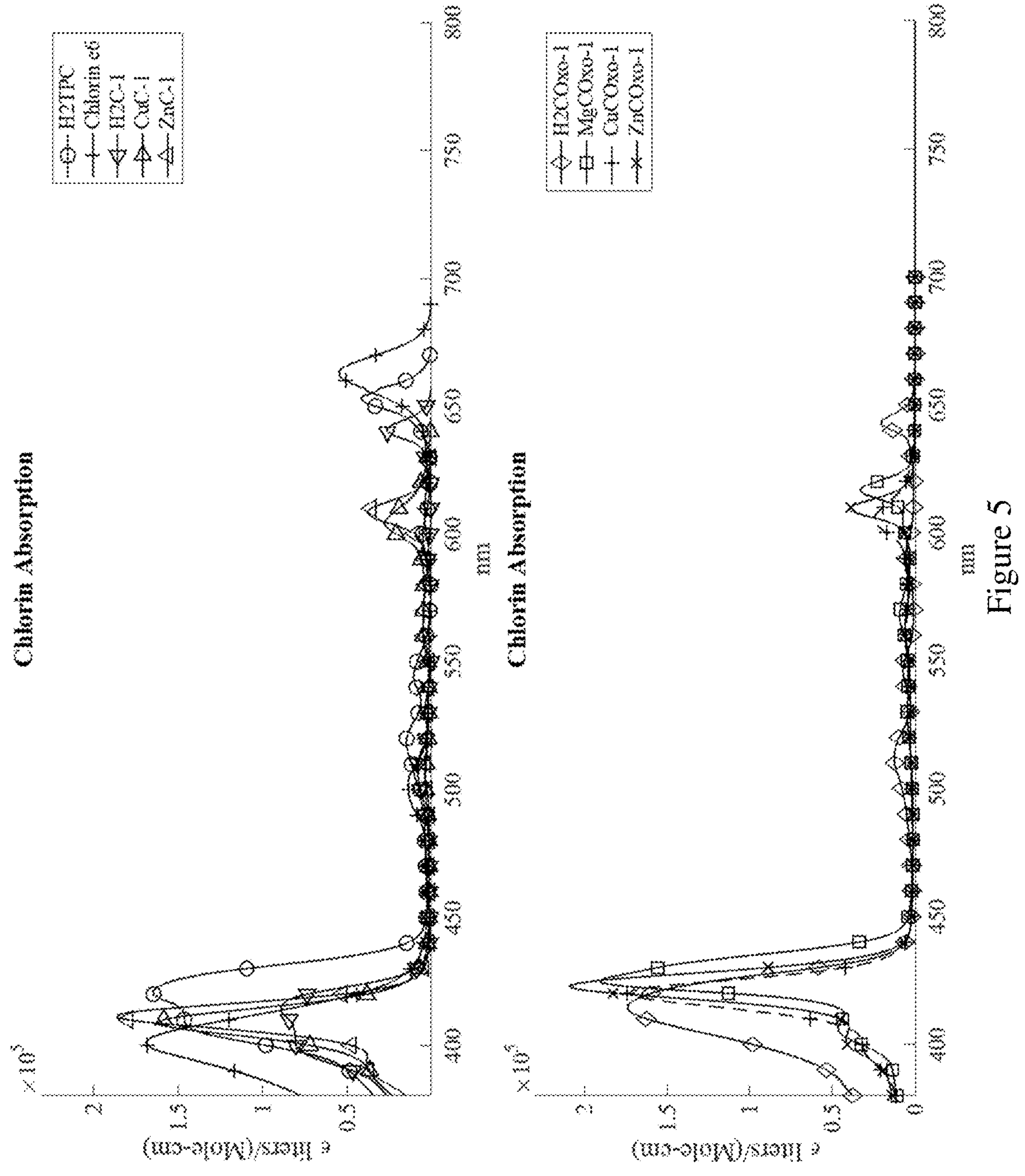
FIG. 5. Absorption spectra of the chlorin chromophores from FIG. 3.
Figure 6A:
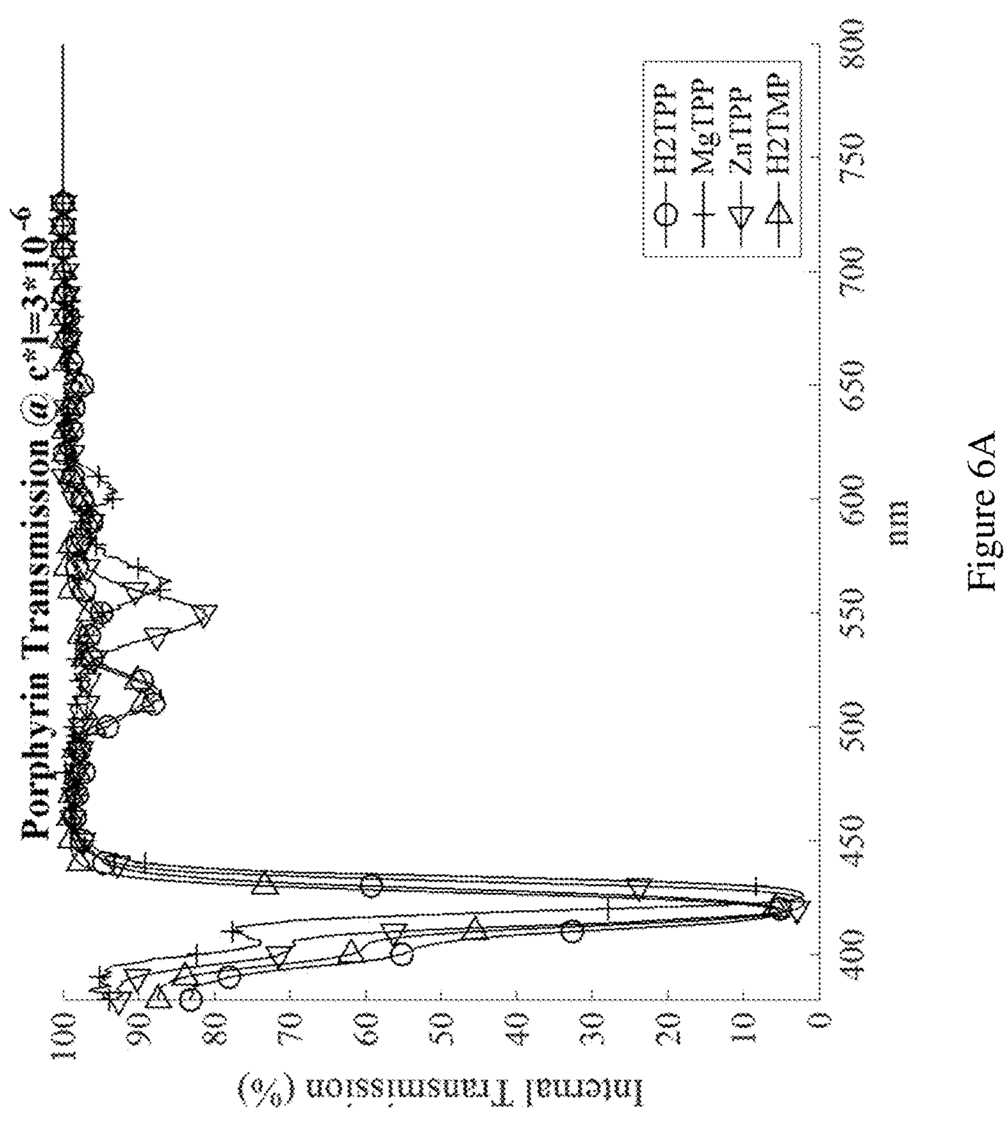
FIG. 6A-C. Internal transmission of porphyrins at a fixed value of concentration*path-length, (c*l), =$3\times10^{-6}$ mol-cm/l.
Figure 6B:
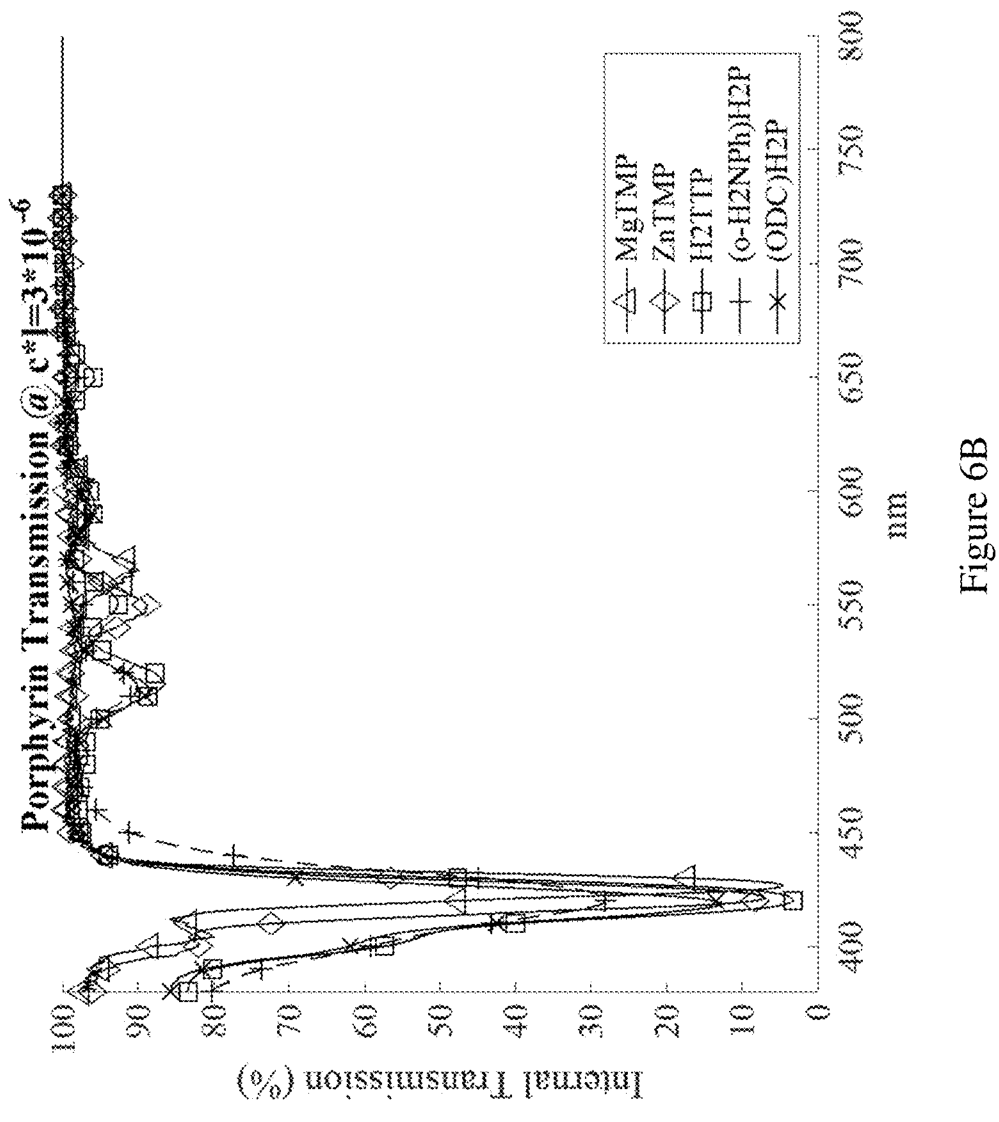
Figure 6C:
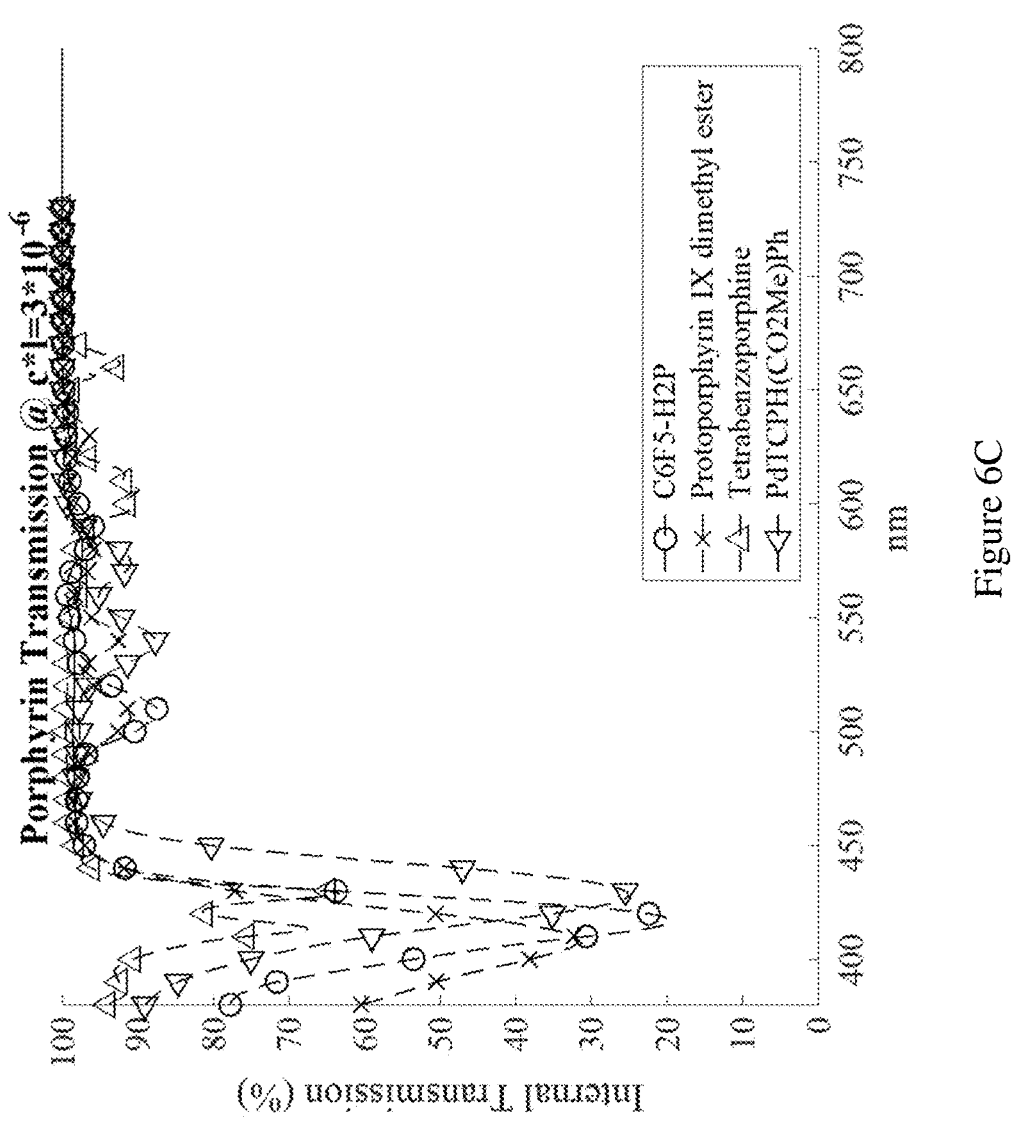

The absorption spectra for the porphyrin and chlorin dyes are shown in FIGS. 4 and 5. According to the present disclosure these spectra must be translated to transmission spectra based on the product of available concentration and path length for the lens. An example of this transformation for a (concentration*path-length) product $3\times10^{-6}$ liters/mole is shown for each of the porphyrin dyes in FIG. 6A-C. Each porphyrin transmission spectrum has different detailed shapes in the 400-450 nm region and has different internal transmission values in the 500-700 nm region where color distortion and luminous transmission are affected.

The relative impact of internal absorption by these dyes is computed by integrating the product of the action spectra with a dyed lens and dividing by the integral of the action spectra with no dye. The resulting percentages are show for the 13 porphyrin dyes and each of the optical qualities, photopic and scotopic luminous transmission, retinal pigment epithelial toxicity, melatonin suppression, and discomfort glare in FIG. 7.

Figure 7:
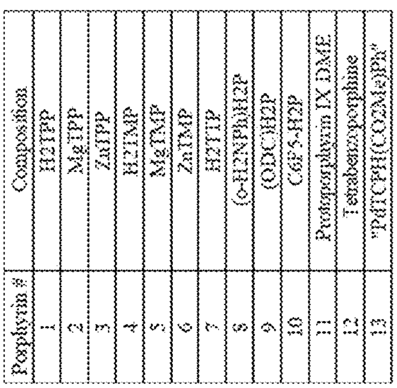
FIG. 7. Retention of various optical properties for the porphyrins of FIG. 2 when c*l=$3\times10^{-6}$ mol-cm/l.
Figure 7:
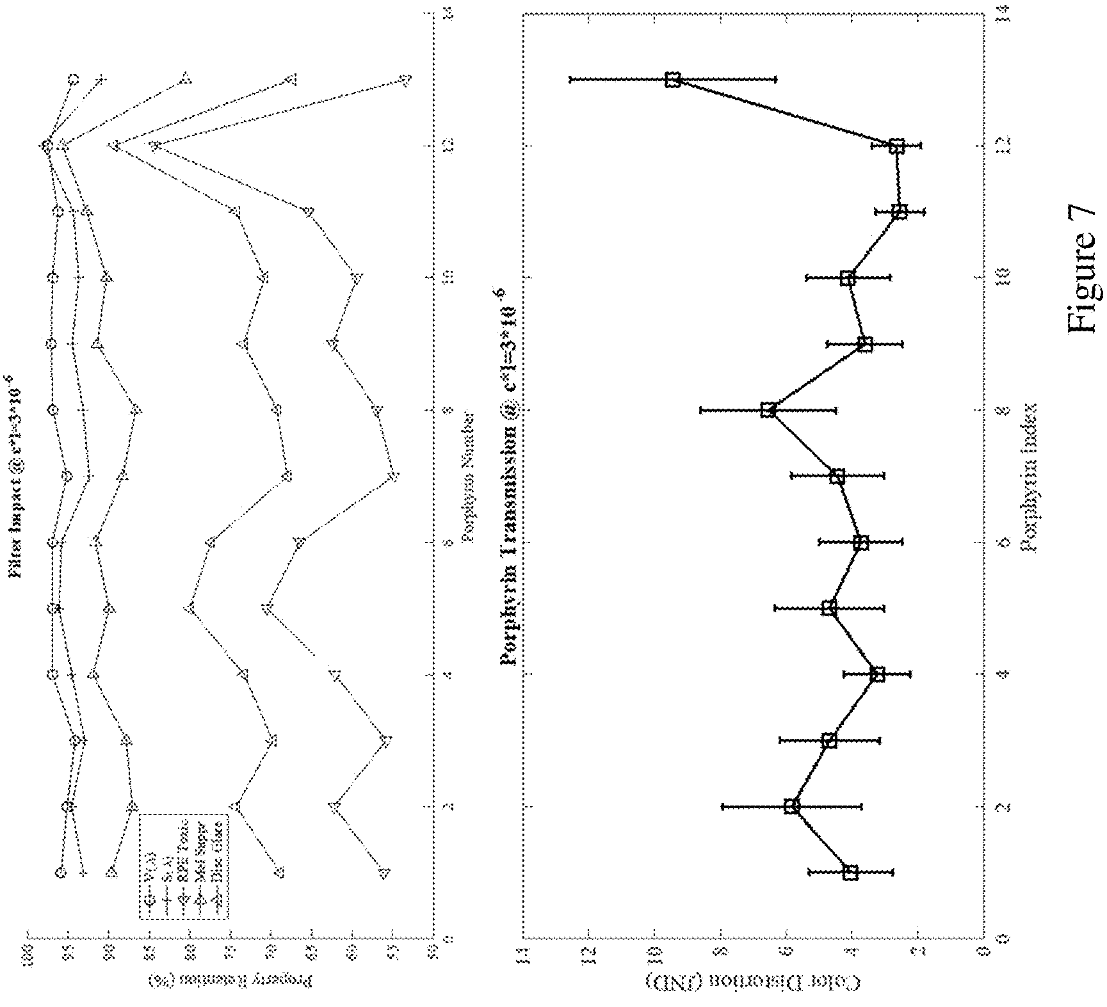

The average color distortion and its standard deviation using the above calculations for these 13 dyes at a concentration*path-length product of $3\times10^{-6}$ l/mol are shown in FIG. 7.

Figure 8:
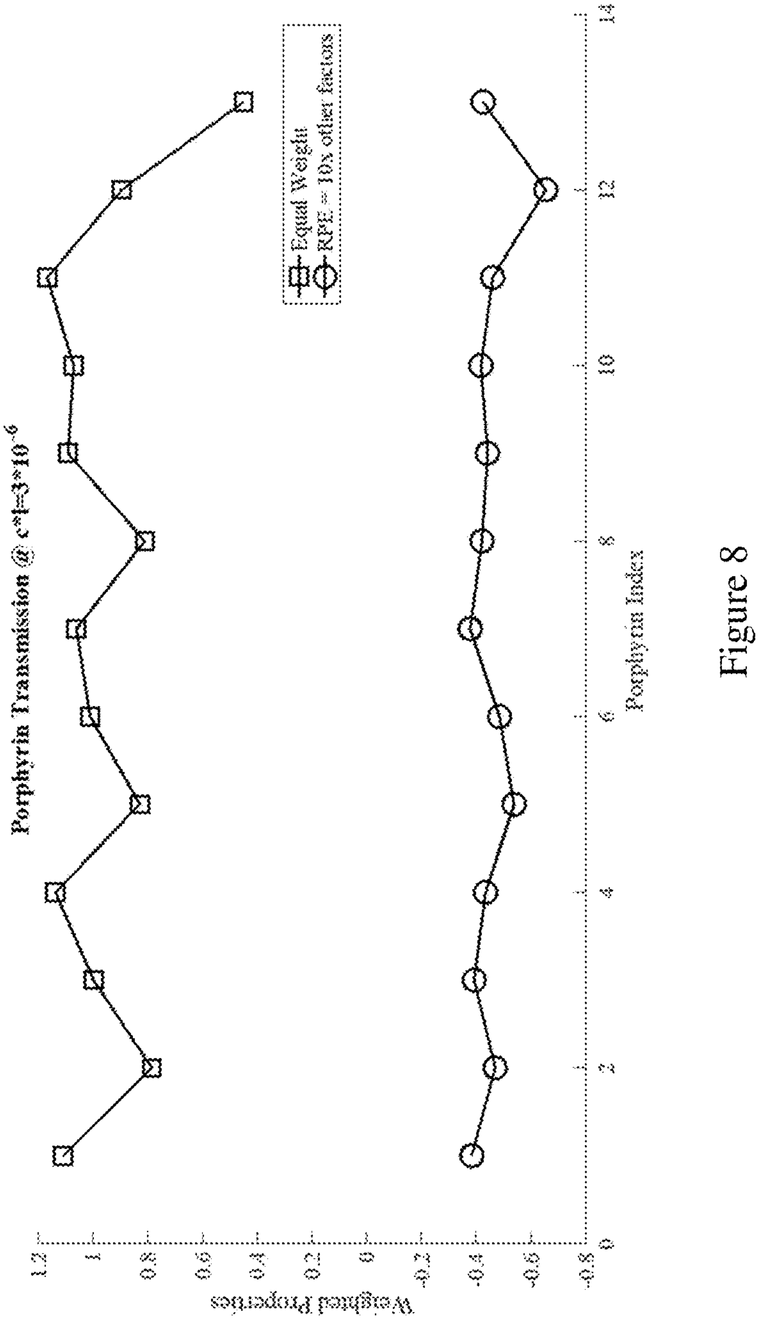
FIG. 8. Weighted properties of the porphyrins from FIG. 2 using equal and RPE damage enhanced weight vectors.

The next and final step in ranking the optical performance of each dye combines the transmissive property changes with the color distortion using a weighting function that quantifies the relative importance of each property displayed in FIG. 8. Table 1 displays the impact to these properties based on changes to the integrals of the various action spectra for each of the 13 porphyrin dyes displayed in Figure at $c*l=3\times10^{-6}$ l/mol and the average color distortion.

TABLE 1

| Porphyrin | H2TPP | MgTPP | ZnTPP | H2TMP | MgTMP | ZnTMP | H2TTP |
|---|---|---|---|---|---|---|---|
| Photopic | 0.9588 | 0.9513 | 0.9416 | 0.9693 | 0.9692 | 0.9693 | 0.9519 |
| Scotopic | 0.9312 | 0.9458 | 0.9298 | 0.9454 | 0.9613 | 0.958 | 0.9238 |
| RPE | 0.5611 | 0.6221 | 0.5584 | 0.6209 | 0.7051 | 0.6648 | 0.5486 |
| Melatonin | 0.8967 | 0.8709 | 0.8783 | 0.9192 | 0.8997 | 0.9161 | 0.8828 |
| Glare | 0.6887 | 0.7431 | 0.6979 | 0.7332 | 0.8 | 0.774 | 0.68 |
| Color Shift | 0.4271 | 0.6167 | 0.4952 | 0.3422 | 0.496 | 0.3944 | 0.4692 |

| Porphyrin | (o-H2NPh)H2P | (ODC)H2P | C6F5-H2P | Protoporphyrin IX dimethyl ester | Tetrabenzo-porphine | PdTCPH(CO2Me)Ph |
|---|---|---|---|---|---|---|
| Photopic | 0.9688 | 0.9712 | 0.9691 | 0.9626 | 0.975 | 0.9437 |
| Scotopic | 0.9316 | 0.945 | 0.9372 | 0.9437 | 0.9812 | 0.9094 |
| RPE | 0.5698 | 0.6238 | 0.5945 | 0.6539 | 0.8443 | 0.5343 |
| Melatonin | 0.8666 | 0.9142 | 0.9027 | 0.927 | 0.9571 | 0.8056 |
| Glare | 0.6927 | 0.7336 | 0.7082 | 0.7429 | 0.8934 | 0.6741 |
| Color Shift | 0.693 | 0.3816 | 0.4357 | 0.2697 | 0.28 | 1 |

The simplest weighting function for ranking these dyes is a vector whose elements are +1 for desirable properties and −1 for undesirable properties: [1 1 −1 1 −1 −1]. The inner product of each column corresponding to a different dye is shown in FIG. 8. Under this weighting scheme at concentration*path-length products of $3\times10^{-6}$ dyes 1, 4, and 11 have the highest merit while dye 13 is least attractive. If market or other factors drive the relative prominence of each component this is easily incorporated in the weighting function. Referring to FIG. 8 the performance of the same 13 dyes is displayed (-o-) when the weighting function is [0.0976 0.0976-9.76-0.0976 0.0976], implying that the protection of RPE is ten times as important as each of the other factors. As displayed, this change has a large impact on the suitability of dye 13, which goes from least to most suitable when RPE protection is most heavily weighted.

Figure 9:
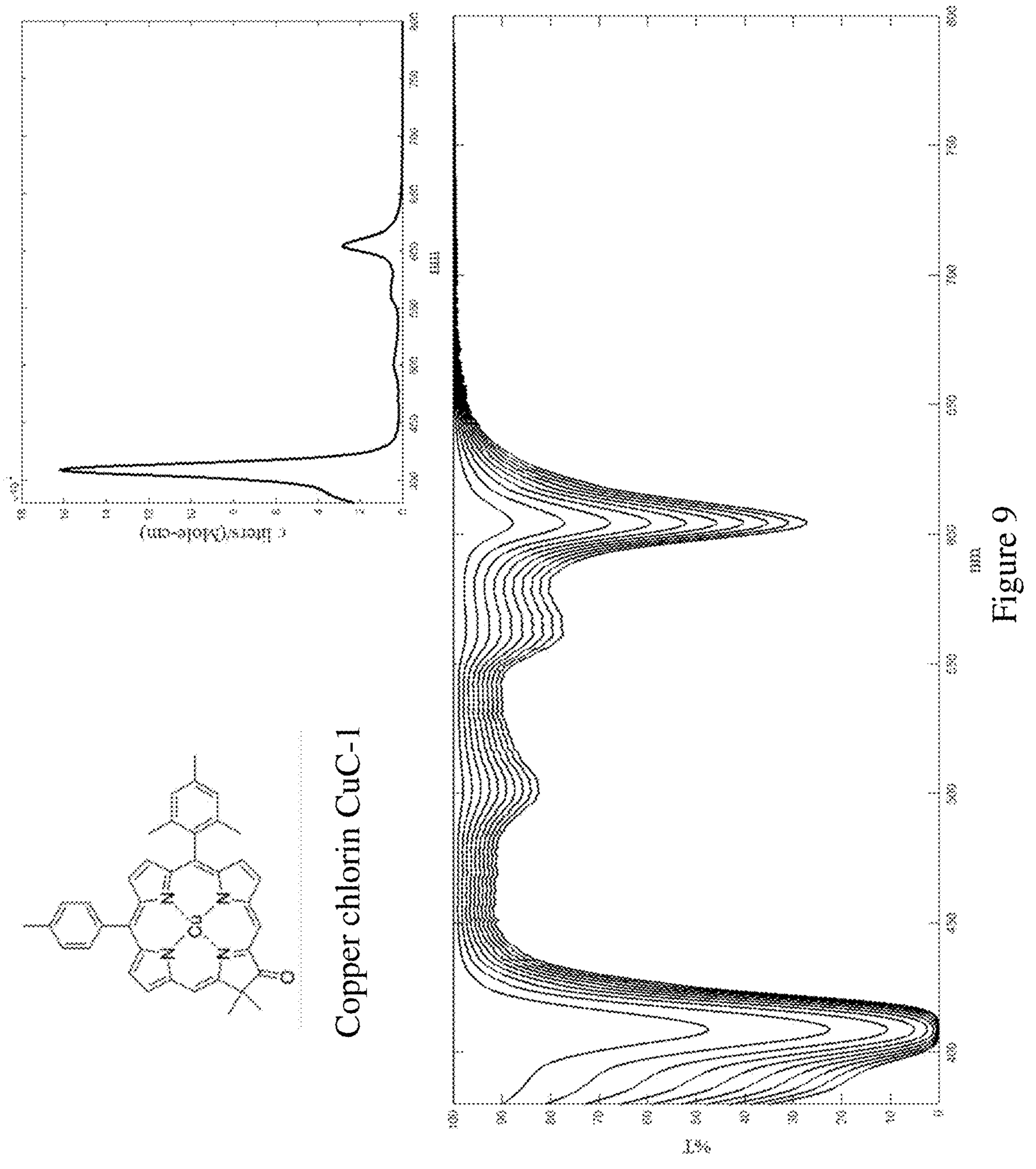
FIG. 9. Absorption spectrum and transmission spectra at c*l values from 0 to $2\times10^{-5}$ in steps of $2\times10^{-6}$ mol-cm/l.
Figure 10A:
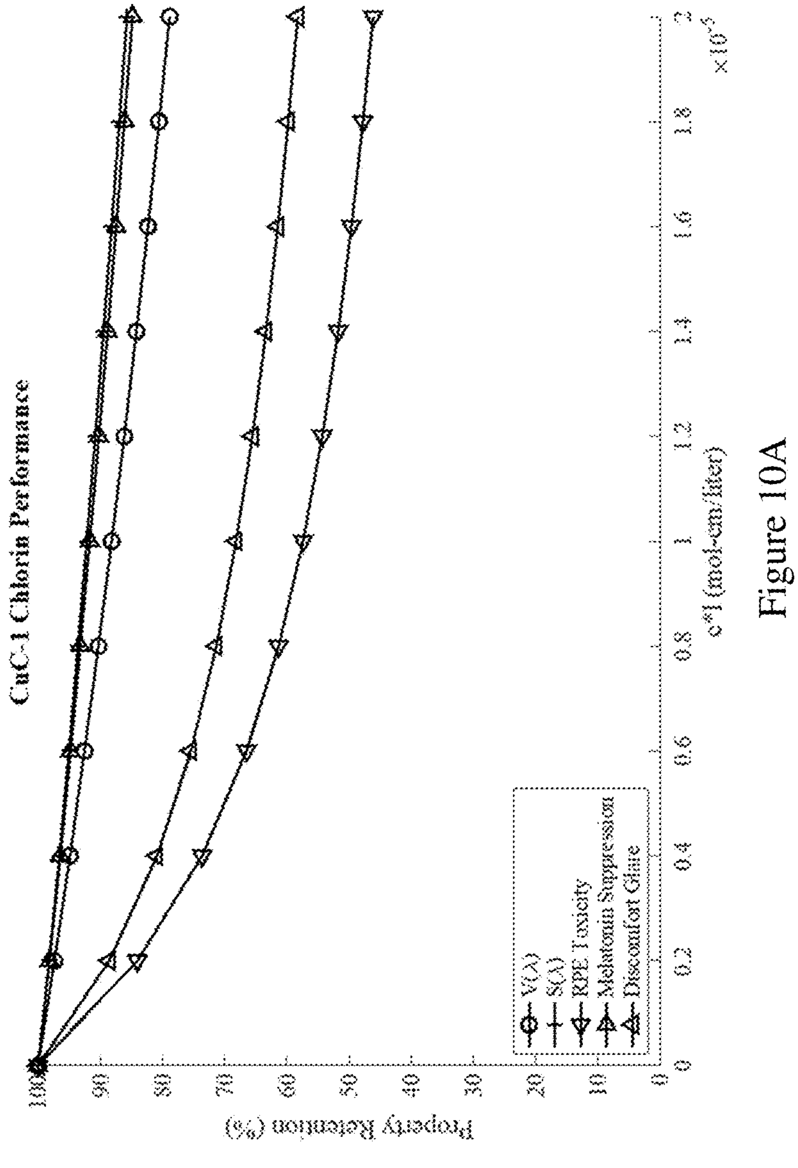
FIG. 10A-B. Property retention (A) and color distortion (B) for the chlorin CuC-1 as a function of c*l.
Figure 10B:
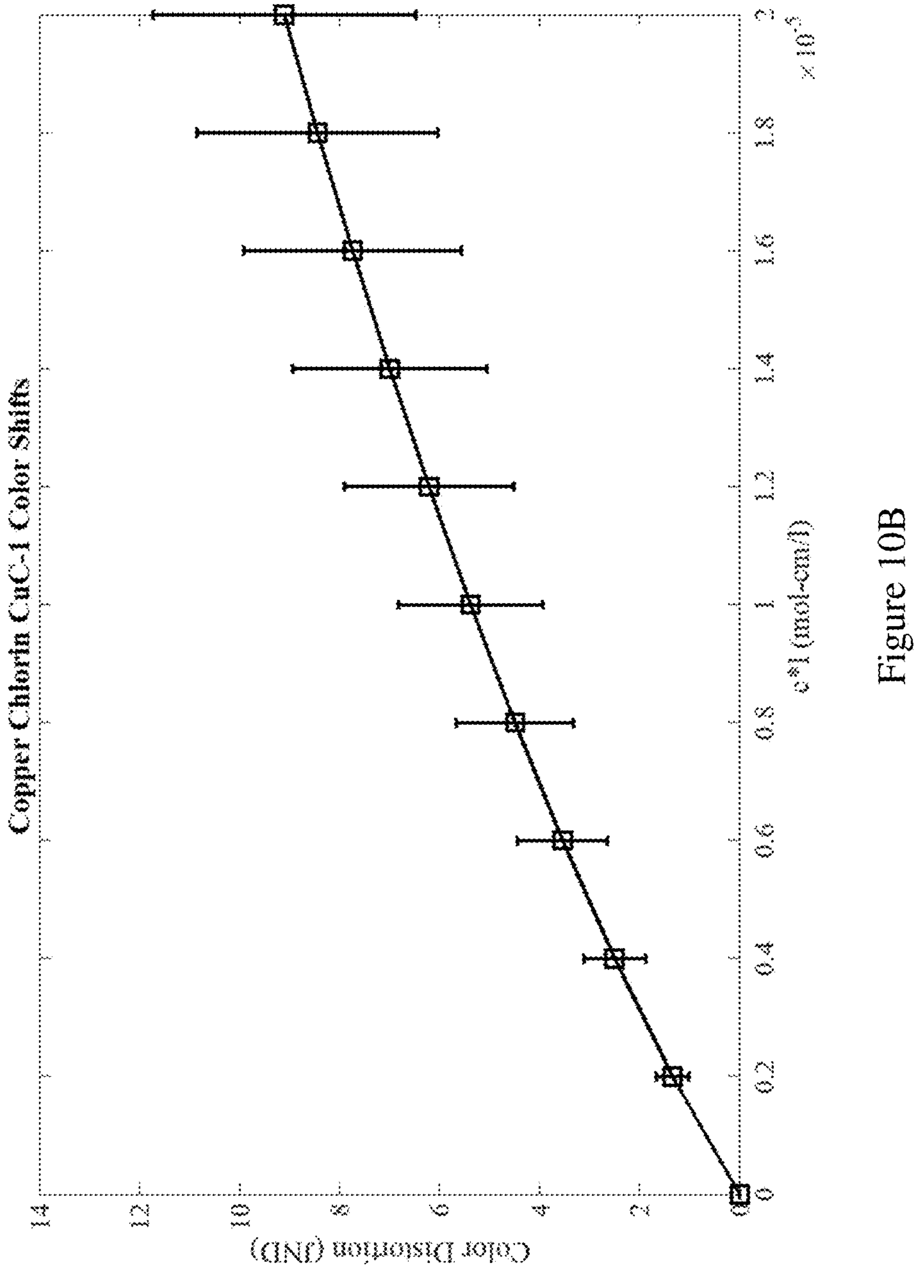
Figure 11:
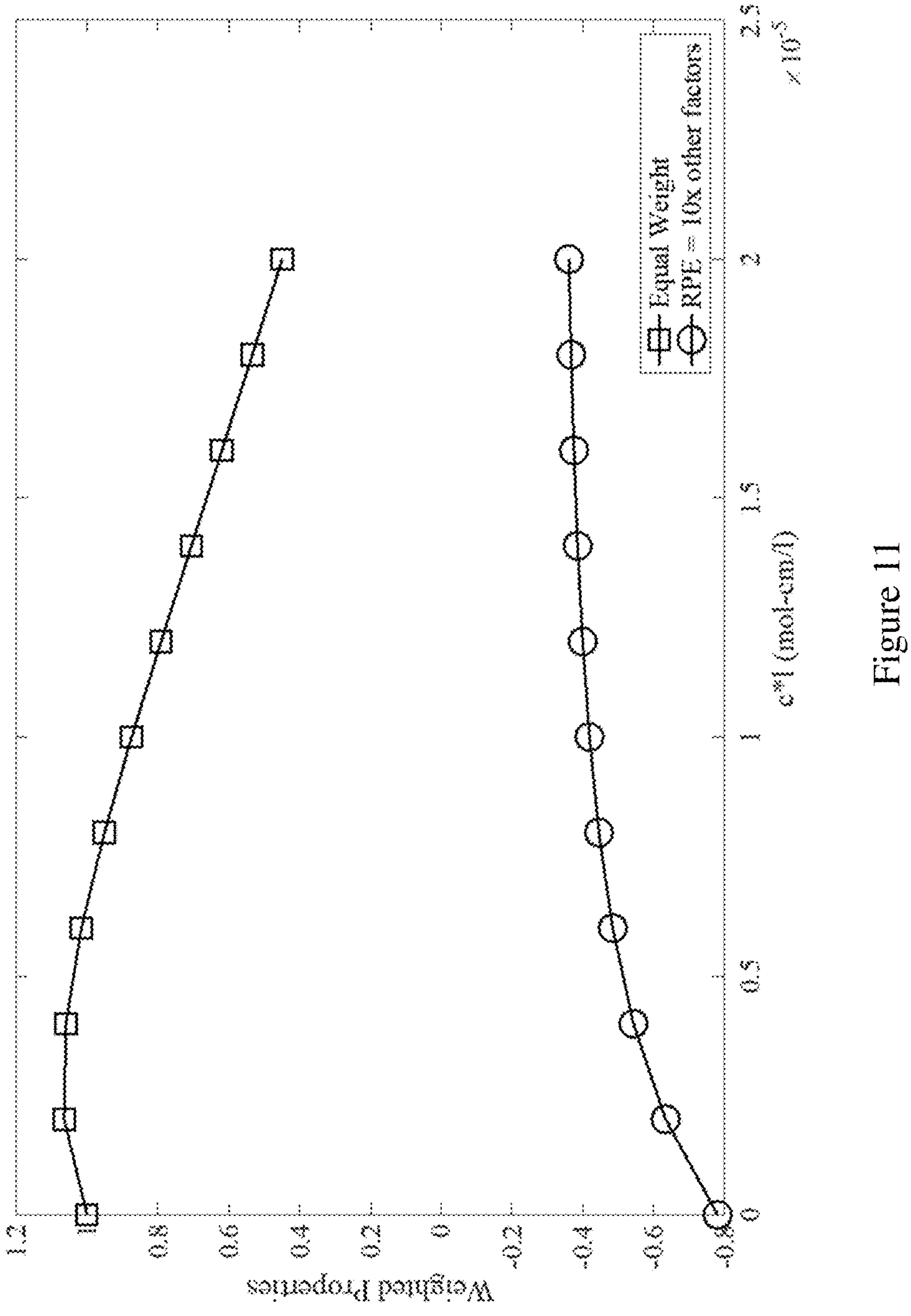
FIG. 11. Weighted properties for CuC-1 as a function of c*l with equal weight and 10× enhancement of RPE protection.

In another embodiment, the concentration of a dye can be adjusted to useful concentrations by evaluating the weighted properties for transmission spectra calculated at different concentrations, subject to solubility and chemical stability constraints, at a prescribed lens thickness. The absorption and transmission spectra at increasing c*l products for the copper chlorin CuC-1 are displayed in FIG. 9. Referring to FIG. 10, the influence of increasing concentration for each of the optical properties is displayed for c*l ranging from 0 to $2\times10^{-5}$ mol-cm/l. Incorporating the color shift and uniform weighting as described for comparison among porphyrins results in a local maximum for the weighted properties of between 2 and $4\times10^{-6}$ as shown in FIG. 11. Enhancing the weight of RPE protection by a factor of ten over the remaining properties changes this picture, with slowly increasing weighted properties c*l above $10^{-5}$.

A further embodiment of the disclosure entails simultaneous maximization of the weighted properties with respect to both dye composition and concentration.

Yet another embodiment of the disclosure uses transmission spectra computed from mixed compositions involving two or more chemically compatible dyes where the ratio of individual dyes is also adjusted to maximize the weighted properties.

Thus, in one embodiment, disclosed is a method of designing an optical device that protects retinal pigment epithelium from blue light, the method comprising:

providing a first optical device comprising a porphyrin or chlorin compound;

providing a second optical device that is identical to the first device without the porphyrin or chlorin compound;

measuring at least two of the following transmissive properties for each of the first and second optical devices: photopic luminous transmission, scotopic luminous transmission, retinal pigment epithelial toxicity, melatonin suppression, and discomfort glare;

integrating an action spectra for each measured transmissive property of the first device;

integrating an action spectra for each measured transmissive property of the second device;

dividing the integral obtained for the first device by the integral obtained for the second device for that measured property to provide a change in the transmissive property;

measuring a color shift in uniform color space for the first optical device as compared to the second optical device;

combining the transmissive property changes and the color shift using a weighting function that quantifies the relative importance of each property; and ranking optical performance of the porphyrin or chlorin compound.

In certain embodiments, the method includes measuring at least three of photopic luminous transmission, scotopic luminous transmission, retinal pigment epithelial toxicity, melatonin suppression, and discomfort glare for each of the first and second optical devices.

In certain embodiments, the method includes measuring at least four of photopic luminous transmission, scotopic luminous transmission, retinal pigment epithelial toxicity, melatonin suppression, and discomfort glare for each of the first and second optical devices.

In certain embodiments, the method includes measuring photopic luminous transmission, scotopic luminous transmission, retinal pigment epithelial toxicity, melatonin suppression, and discomfort glare for each of the first and second optical devices.

Compounds

Preferred embodiments of the disclosure incorporate the optical properties of porphyrin and chlorin derivatives with modifications that ensure covalent bonding with the lens resins. Accordingly, compounds (e.g., compounds of Formula (I) and (II)) were designed and developed to incorporate the desired optical properties into appropriate devices (e.g., as compounds of Formula (III)).

In one aspect, disclosed are porphyrin and chlorin compounds such as compounds of Formula (I):

(I)

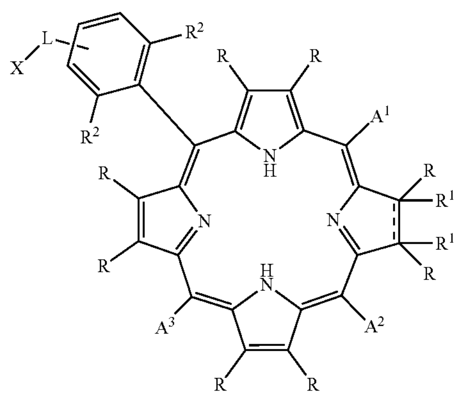

or a salt, or tautomer thereof, wherein:

each R is independently hydrogen, halogen, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, or two adjacent R groups, together with the atoms to which they are attached, form a substituted or unsubstituted $C_6$-$C_{14}$ aryl, substituted or unsubstituted $C_3$-$C_{14}$ carbocyclyl, substituted or unsubstituted $C_5$-$C_{14}$ heteroaryl, or substituted or unsubstituted $C_3$-$C_{14}$ heterocyclyl;

each $R^1$ is independently hydrogen, halogen, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, or two adjacent R groups, together with the atoms to which they are attached, form a substituted or unsubstituted $C_6$-$C_{14}$ aryl, substituted or unsubstituted $C_3$-$C_{14}$ carbocyclyl, substituted or unsubstituted $C_5$-$C_{14}$ heteroaryl, or substituted or unsubstituted $C_3$-$C_{14}$ heterocyclyl; or one instance of $R^1$ and R on the same carbon form with that carbon a carbonyl;

$A^1$, $A^2$, and $A^3$ are independently hydrogen or a substituted aryl of formula:

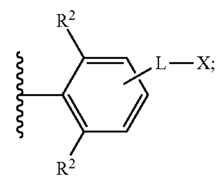

each $R^2$ is independently hydrogen, halogen, —$NO_2$, substituted or unsubstituted alkyl, —$NHR^A$, —$N(R^A)_2$, or —$OR^B$;

------ is a single or double bond, provided that when ------ is double bond, then each $R^1$ is absent;

each L is independently a bond or —$R^3$—$X^L$—$R^4$—;

each $R^3$ and $R^4$ are independently a bond, substituted or unsubstituted $C_1$-$C_{20}$ alkylene, substituted or unsubstituted $C_1$-$C_{20}$ heteroalkylene, substituted or unsubstituted $C_3$-$C_{14}$ carbocyclylene, or substituted or unsubstituted $C_3$-$C_{14}$ heterocyclylene;

each $X^L$ is independently a bond, —O—, —$N(R^A)$—, —$N+(R^A)_2$—, —S—, —C(═O)—, —C(═O)O—, —C(═O)$NR^A$—, —$NR^A$C(═O)—, —$NR^A$C(═O)$R^A$—, —C(═O)$R^A$—, —$NR^A$C(═O)O—, —$NR^A$C(═O)$N(R^A)$—, —OC(═O)—, —OC(═O)O—, —OC(═O)$N(R^A)$—, —$S(O)_2NR^A$—, —$NR^AS(O)_2$—, or a combination thereof;

each X is independently hydrogen, halogen, substituted or unsubstituted $C_1$-$C_{20}$ alkyl, or a polymerizable group, provided that at least one X is a polymerizable group;

each occurrence of $R^A$ is independently hydrogen, substituted or unsubstituted acyl, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, substituted or unsubstituted $C_3$-$C_{14}$ carbocyclyl, substituted or unsubstituted $C_3$-$C_{14}$ heterocyclyl, substituted or unsubstituted $C_6$-$C_{14}$ aryl, substituted or unsubstituted $C_5$-$C_{14}$ heteroaryl, a nitrogen protecting group, or two $R^A$ groups are joined to form a substituted or unsubstituted $C_3$-$C_{14}$ heterocyclyl, or a substituted or unsubstituted $C_5$-$C_{14}$ heteroaryl; and each occurrence of $R^B$ is independently hydrogen, substituted or unsubstituted acyl, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, substituted or unsubstituted $C_3$-$C_{14}$ carbocyclyl, substituted or unsubstituted $C_3$-$C_{14}$ heterocyclyl, substituted or unsubstituted $C_{6-14}$ aryl, or substituted or unsubstituted $C_{5-14}$ heteroaryl.

In another aspect, disclosed are metalloporphyrin and metallochlorin compounds such as compounds of Formula (II):

(II)

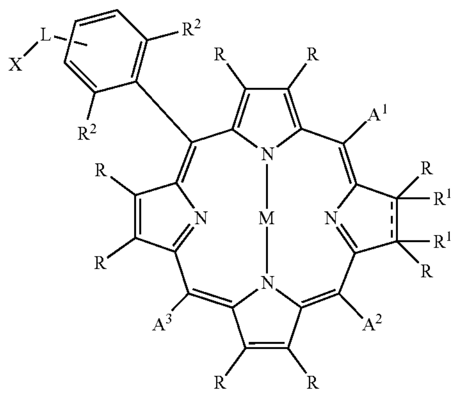

or a salt, or tautomer thereof, wherein:

M is a metal;

each R is independently hydrogen, halogen, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, or two adjacent R groups, together with the atoms to which they are attached, form a substituted or unsubstituted $C_6$-$C_{14}$ aryl, substituted or unsubstituted $C_3$-$C_{14}$ carbocyclyl, substituted or unsubstituted $C_5$-$C_{14}$ heteroaryl, or substituted or unsubstituted $C_3$-$C_{14}$ heterocyclyl;

each $R^1$ is independently hydrogen, halogen, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, or two adjacent R groups, together with the atoms to which they are attached, form a substituted or unsubstituted $C_6$-$C_{14}$ aryl, substituted or unsubstituted $C_3$-$C_{14}$ carbocyclyl, substituted or unsubstituted $C_5$-$C_{14}$ heteroaryl, or substituted or unsubstituted $C_3$-$C_{14}$ heterocyclyl; or one instance of $R^1$ and R on the same carbon form with that carbon a carbonyl;

$A^1$, $A^2$, and $A^3$ are independently hydrogen or a substituted aryl of formula:

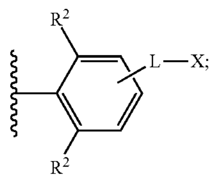

each $R^2$ is independently hydrogen, halogen, —$NO_2$, substituted or unsubstituted alkyl, —$NHR^A$, —$N(R^A)_2$, or —$OR^B$;

------ is a single or double bond, provided that when ------ is double bond, then each $R^1$ is absent;

each L is independently a bond or —$R^3$—$X^L$—$R^4$—;

each $R^3$ and $R^4$ are independently a bond, substituted or unsubstituted $C_1$-$C_{20}$ alkylene, substituted or unsubstituted $C_1$-$C_{20}$ heteroalkylene, substituted or unsubstituted $C_3$-$C_{14}$ carbocyclylene, or substituted or unsubstituted $C_3$-$C_{14}$ heterocyclylene;

each $X^L$ is independently a bond, —O—, —$N(R^A)$—, —$N+(R^A)_2$—, —S—, —C(═O)—, —C(═O)O—, —C(═O)$NR^A$—, —$NR^A$C(═O)—, —$NR^A$C(═O)$R^A$—, —C(═O)$R^A$—, —$NR^A$C(═O)O—, —$NR^A$C(═O)N($R^A$)—, —OC(═O)—, —OC(═O)O—, —OC(═O)N($R^A$)—, —$S(O)_2NR^A$—, —$NR^AS(O)_2$—, or a combination thereof;

each X is independently hydrogen, halogen, substituted or unsubstituted $C_1$-$C_{20}$ alkyl, or a polymerizable group, provided that at least one X is a polymerizable group;

each occurrence of $R^A$ is independently hydrogen, substituted or unsubstituted acyl, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, substituted or unsubstituted $C_3$-$C_{14}$ carbocyclyl, substituted or unsubstituted $C_3$-$C_{14}$ heterocyclyl, substituted or unsubstituted $C_6$-$C_{14}$ aryl, substituted or unsubstituted $C_5$-$C_{14}$ heteroaryl, a nitrogen protecting group, or two $R^A$ groups are joined to form a substituted or unsubstituted $C_3$-$C_{14}$ heterocyclyl, or a substituted or unsubstituted $C_5$-$C_{14}$ heteroaryl; and each occurrence of $R^B$ is independently hydrogen, substituted or unsubstituted acyl, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, substituted or unsubstituted $C_3$-$C_{14}$ carbocyclyl, substituted or unsubstituted $C_3$-$C_{14}$ heterocyclyl, substituted or unsubstituted $C_{6-14}$ aryl, or substituted or unsubstituted $C_{5-14}$ heteroaryl.

M

As defined herein, M is a metal. In certain embodiments, M is a transition metal. In certain embodiments, M is copper, vanadium, or cobalt. In certain embodiments, M is copper. In certain embodiments, M is vanadium. In certain embodiments, M is cobalt.

R

As defined herein, each R is independently hydrogen, halogen, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, or two adjacent R groups, together with the atoms to which they are attached, form a substituted or unsubstituted $C_6$-$C_{14}$ aryl, substituted or unsubstituted $C_3$-$C_{14}$ carbocyclyl, substituted or unsubstituted $C_5$-$C_{14}$ heteroaryl, or substituted or unsubstituted $C_3$-$C_{14}$ heterocyclyl.

In certain embodiments, each R is independently hydrogen, halogen, substituted or unsubstituted $C_1$-$C_{20}$ alkyl, or two adjacent R groups, together with the atoms to which they are attached, form a substituted or unsubstituted $C_3$-$C_{14}$ carbocyclyl.

In certain embodiments, each R is independently hydrogen, halogen, or two adjacent R groups, together with the atoms to which they are attached, form a substituted or unsubstituted $C_3$-$C_{14}$ carbocyclyl.

In certain embodiments, each R is independently hydrogen, bromo, chloro, or two adjacent R groups, together with the atoms to which they are attached, form a substituted or unsubstituted $C_3$-$C_{14}$ carbocyclyl.

In certain embodiments, each R is independently hydrogen or halogen. In certain embodiments, each R is independently hydrogen or bromo. In certain embodiments, each R is hydrogen.

In certain embodiments, each R forms a substituted or unsubstituted $C_3$-$C_{14}$ carbocyclyl with the R on the adjacent carbon. In certain embodiments, each R forms an unsubstituted $C_3$-$C_{14}$ carbocyclyl with the R on the adjacent carbon. In certain embodiments, each R forms an unsubstituted 6-membered carbocyclyl with the R on the adjacent carbon.

$R^1$

In certain embodiments, ------ is a single bond, thus providing a chlorin compound.

When ------ is a single bond, each $R^1$ is independently hydrogen, halogen, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, or two adjacent R groups, together with the atoms to which they are attached, form a substituted or unsubstituted $C_6$-$C_{14}$ aryl, substituted or unsubstituted $C_3$-$C_{14}$ carbocyclyl, substituted or unsubstituted $C_5$-$C_{14}$ heteroaryl, or substituted or unsubstituted $C_3$-$C_{14}$ heterocyclyl; or one instance of $R^1$ and R on the same carbon form with that carbon a carbonyl. In certain embodiments, each $R^1$ is independently hydrogen, or substituted or unsubstituted $C_1$-$C_{20}$ alkyl. In certain embodiments, each $R^1$ is independently hydrogen, or unsubstituted $C_1$-$C_{20}$ alkyl. In certain embodiments, each $R^1$ is hydrogen.

$R^2$

As defined herein, each $R^2$ is independently hydrogen, halogen, —$NO_2$, substituted or unsubstituted alkyl, —$NHR^A$, —$N(R^A)_2$, or —$OR^B$. In certain embodiments, each $R^2$ is independently hydrogen, —$OR^B$, or halogen. In certain embodiments, each $R^2$ is independently hydrogen, halogen, substituted or unsubstituted $C_{1-4}$ alkyl, or —$OC_{1-4}$ alkyl. In certain embodiments, each $R^2$ is independently hydrogen, halogen, unsubstituted $C_{1-4}$ alkyl, or —$OC_{1-4}$ alkyl. In certain embodiments, each $R^2$ is independently hydrogen, halogen, or —$OC_{1-4}$ alkyl. In certain embodiments, each $R^2$ is independently hydrogen, —Cl, or —$OCH_3$. In certain embodiments, each $R^2$ is independently hydrogen or —$OC_{1-4}$ alkyl. In certain embodiments, each $R^2$ is independently hydrogen or —$OCH_3$. In certain embodiments, each $R^2$ is independently halogen or —$OC_{1-4}$ alkyl. In certain embodiments, each $R^2$ is independently —Cl or —$OCH_3$. In certain embodiments, each $R^2$ is independently hydrogen or halogen. In certain embodiments, each $R^2$ is hydrogen or —Cl. In certain embodiments, each $R^2$ is independently —Cl. In certain embodiments, each $R^2$ is independently hydrogen. In certain embodiments, each $R^2$ is —$OCH_3$.

$A^1$, $A^2$, and $A^3$

As defined herein, $A^1$, $A^2$, and $A^3$ are independently hydrogen or a substituted aryl of formula:

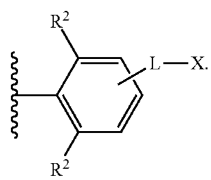

In certain embodiments, $A^1$ is of formula:

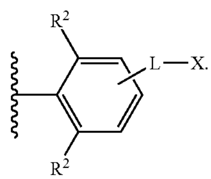

In certain embodiments, $A^1$ is of formula:

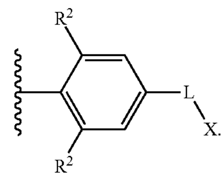

In certain embodiments, $A^1$ is hydrogen.

In certain embodiments, $A^2$ is of formula:

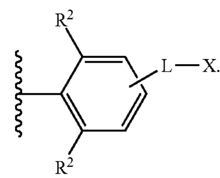

In certain embodiments, $A^2$ is of formula:

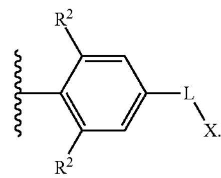

In certain embodiments, $A^2$ is hydrogen.

In certain embodiments, $A^3$ is of formula:

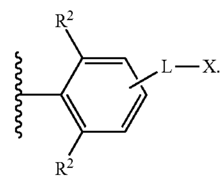

In certain embodiments, $A^3$ is of formula:

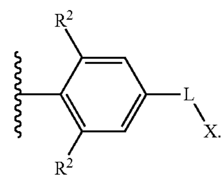

In certain embodiments, $A^3$ is hydrogen.

In certain embodiments, $A^1$, $A^2$, and $A^3$ are each hydrogen. In certain embodiments, $A^1$, $A^2$, and $A^3$ are independently of formula:

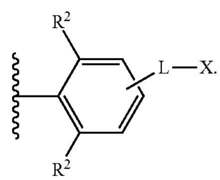

In certain embodiments, $A^1$, $A^2$, and $A^3$ are independently of formula:

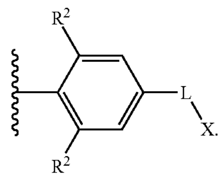

L

As defined herein, each L is independently a bond or $—R^3—X^L—R^4—$; wherein each $R^3$ and $R^4$ are independently a bond, substituted or unsubstituted $C_1$-$C_{20}$ alkylene, substituted or unsubstituted $C_1$-$C_{20}$ heteroalkylene, substituted or unsubstituted $C_3$-$C_{14}$ carbocyclylene, or substituted or unsubstituted $C_3$-$C_{14}$ heterocyclylene; and each $X^L$ is independently a bond, —O—, $—N(R^A)—$, $—N+(R^A)_2—$, —S—, —C(═O)—, —C(═O)O—, $—C(═O)NR^A—$, $—NR^AC(═O)—$, $—NR^AC(═O)R^A—$, $—C(═O)R^A—$, $—NR^AC(═O)O—$, $—NR^AC(═O)N(R^A)—$, —OC(═O)—, —OC(═O)O—, $—OC(═O)N(R^A)—$, $—S(O)_2NR^A—$, $—NR^AS(O)_2—$, or a combination thereof.

In certain embodiments, each L is independently $—R^3—X^L—R^4—$; wherein each $R^3$ and $R^4$ are independently substituted or unsubstituted $C_1$-$C_{20}$ alkylene, or substituted or unsubstituted $C_1$-$C_{20}$ heteroalkylene; and each $X^L$ is independently a bond, —O—, $—N(R^A)—$, $—N+(R^A)_2—$, —C(═O)—, $—NR^AC(═O)—$, —OC(═O)—, or a combination thereof.

In certain embodiments, each L is independently $—R^3—X^L—R^4—$; wherein each $R^3$ and $R^4$ are independently substituted or unsubstituted $C_1$-$C_{20}$ alkylene, or substituted or unsubstituted $C_1$-$C_{20}$ heteroalkylene; and each $X^L$ is independently —O—, $—N(R^A)—$, $—N+(R^A)_2—$, —C(═O)—, $—NR^AC(═O)—$, or —OC(═O)—, or a combination thereof.

In certain embodiments, each L is independently $—R^3—X^L—R^4—$; wherein each $R^3$ and $R^4$ are independently a substituted or unsubstituted $C_1$-$C_{20}$ alkylene, or substituted or unsubstituted $C_1$-$C_{20}$ heteroalkylene; and each $X^L$ is independently a bond, $—N(R^A)—$, or $—N+(R^A)_2—$.

In certain embodiments, each L is independently $—R^3—X^L—R^4—$; wherein each $R^3$ and $R^4$ are independently a substituted or unsubstituted $C_1$-$C_{20}$ alkylene, or substituted or unsubstituted $C_1$-$C_{20}$ heteroalkylene; and each $X^L$ is independently $—N(R^A)—$ or $—N^+(R^A)_2—$.

In certain embodiments, each L is independently $—R^3—X^L—R^4—$; wherein each $R^3$ and $R^4$ are independently a substituted or unsubstituted $C_1$-$C_{20}$ alkylene; and each $X^L$ is independently a bond, $—N(R^A)—$, or $—N+(R^A)_2—$. In certain embodiments, each L is independently $—R^3—X^L—R^4—$; wherein each $R^3$ and $R^4$ are independently a substituted or unsubstituted $C_1$-$C_{20}$ alkylene; and each $X^L$ is independently $—N(R^A)—$ or $—N+(R^A)_2—$. In certain embodiments, each L is independently $—R^3—X^L—R^4—$;

wherein each $R^3$ and $R^4$ are independently substituted or unsubstituted $C_{1-3}$ alkylene; and each $X^L$ is independently $—N(R^A)—$ or $—N^+(R^A)_2$.

In certain embodiments, each L is independently unsubstituted $C_{1-3}$ alkylene,

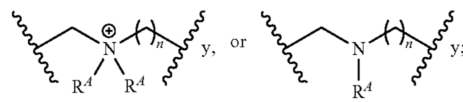

n is 1-6; each occurrence of $R^A$ is independently substituted or unsubstituted $C_1$-$C_{20}$ alkyl; and y labels the site with attachment to group X. In certain embodiments, each L is independently

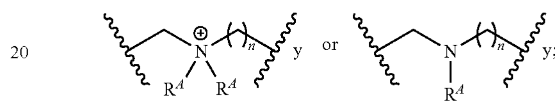

n is 1-6; each occurrence of $R^A$ is independently substituted or unsubstituted $C_1$-$C_{20}$ alkyl; and y labels the site with attachment to group X.

In certain embodiments, each L is independently unsubstituted $C_{1-3}$ alkylene, or

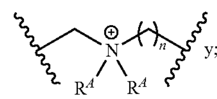

n is 1-6; each occurrence of $R^A$ is independently substituted or unsubstituted $C_1$-$C_{20}$alkyl; and y labels the site with attachment to group X. In certain embodiments, each L is independently

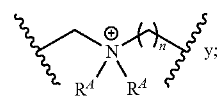

n is 1-6; each occurrence of $R^A$ is independently substituted or unsubstituted $C_1$-$C_{20}$ alkyl; and y labels the site with attachment to group X.

In certain embodiments, each L is independently unsubstituted $C_{1-3}$ alkylene, or

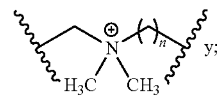

n is 1-3; and y labels the site with attachment to group X. In certain embodiments, each L is independently

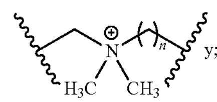

n is 1-3; and y labels the site with attachment to group X.

In certain embodiments, each L is independently unsubstituted methylene,

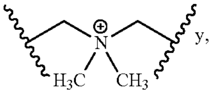 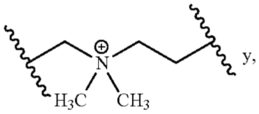 or

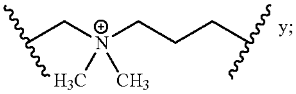

wherein y labels the site with attachment to group X. In certain embodiments, each L is independently

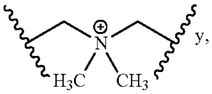 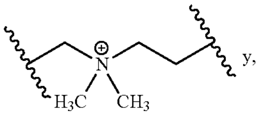 or

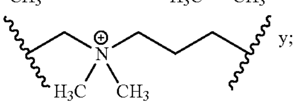

wherein y labels the site with attachment to group X.

In certain embodiments, each L is independently unsubstituted methylene, or

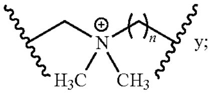

wherein y labels the site with attachment to group X. In certain embodiments, each L is

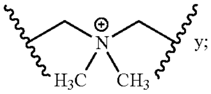

wherein y labels the site with attachment to group X.

In certain embodiments, each L is independently unsubstituted methylene, or

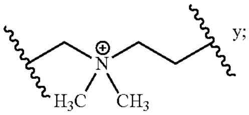 [SMILES: *CC[N+](C)(C)C*]

wherein y labels the site with attachment to group X. In certain embodiments, each L is

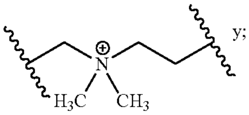

wherein y labels the site with attachment to group X.

In certain embodiments, each L is independently unsubstituted methylene, or

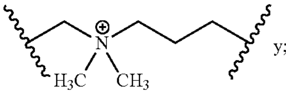

wherein y labels the site with attachment to group X. In certain embodiments, each L is

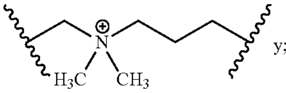

wherein y labels the site with attachment to group X.

X

As defined herein, each X is independently hydrogen, halogen, substituted or unsubstituted $C_1$-$C_{20}$ alkyl, or a polymerizable group.

In certain embodiments, at least one X is a $C_1$-$C_{20}$ haloalkyl. In certain embodiments, at least one X is a $C_1$-$C_4$ haloalkyl. In certain embodiments, at least one X is a $C_1$-$C_4$ bromoalkyl.

In certain embodiments, at least one X is a bromomethyl. In certain embodiments, at least one X is a halogen.

In certain embodiments, X is a halogen only when the L that it is attached to is unsubstituted methylene; and the remaining X groups are polymerizable groups as defined herein. In certain embodiments, each X is independently a polymerizable group. In certain embodiments, each X is independently a halogen, an acrylate, a methacrylate, an acrylamide, a methacrylamide, a styrene, a vinyl sulfone, or alkenyl; wherein each X is substituted or unsubstituted. In certain embodiments, each X is independently an acrylate, a methacrylate, an acrylamide, a methacrylamide, a styrene, a vinyl sulfone, or alkenyl; wherein each X is substituted or unsubstituted. In certain embodiments, each X is independently a halogen, an acrylate, a methacrylate, an acrylamide, a methacrylamide, or a styrene; wherein each X is substituted or unsubstituted. In certain embodiments, each X is independently an acrylate, a methacrylate, an acrylamide, a methacrylamide, or a styrene; wherein each X is substituted or unsubstituted.

In certain embodiments, each X is a halogen, or a substituted or unsubstituted acrylate. In certain embodiments, each X is a substituted or unsubstituted acrylate. In certain embodiments, each X is halogen, or a substituted or unsubstituted methacrylate. In certain embodiments, each X is a substituted or unsubstituted methacrylate. In certain embodiments, each X is halogen, or a substituted or unsubstituted acrylamide. In certain embodiments, each X is a substituted or unsubstituted acrylamide. In certain embodiments, each X is halogen, or a substituted or unsubstituted methacrylamide. In certain embodiments, each X is a substituted or unsubstituted methacrylamide. In certain embodiments, each X is halogen, or a substituted or unsubstituted styrene. In certain embodiments, each X is a substituted or unsubstituted styrene.

In certain embodiments, each X is halogen, or a substituted or unsubstituted vinyl sulfone. In certain embodiments, each X is a substituted or unsubstituted vinyl sulfone. In certain embodiments, each X is halogen, or a substituted or unsubstituted alkenyl. In certain embodiments, each X is substituted or unsubstituted alkenyl.

In certain embodiments, each X is independently —Br, —Cl,

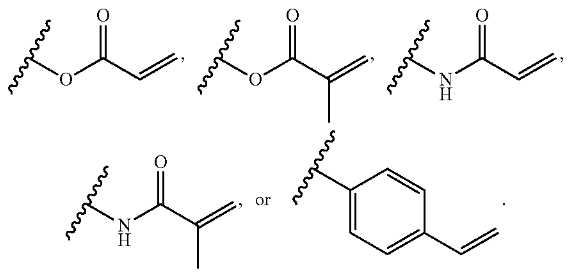

In certain embodiments, each X is independently

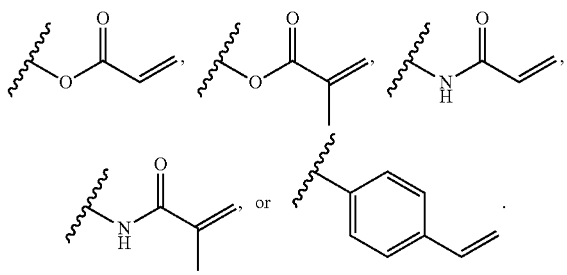

In certain embodiments, each X is —Br or

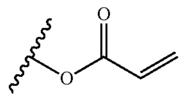

In certain embodiments, each X is

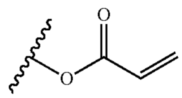

In certain embodiments, each X is —Br

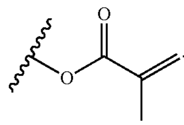 [SMILES: *OC(=O)C(=C)C]

In certain embodiments, each X is

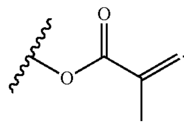 [SMILES: *OC(=O)C(=C)C]

In certain embodiments, each X is —Br or

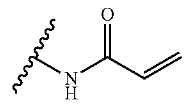

In certain embodiments, each X is

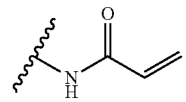

In certain embodiments, each X is —Br or

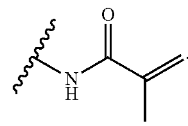 [SMILES: *NC(=O)C(=C)C]

In certain embodiments, each X is

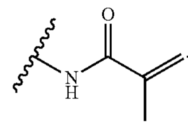 [SMILES: *NC(=O)C(=C)C]

In certain embodiments, each X is independently —Br or

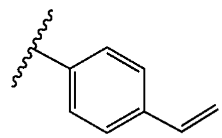

In certain embodiments, each X is

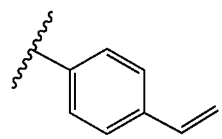

EMBODIMENTS

In certain embodiments, the compound of Formula (I) is of Formula (I-1):

(I-1)

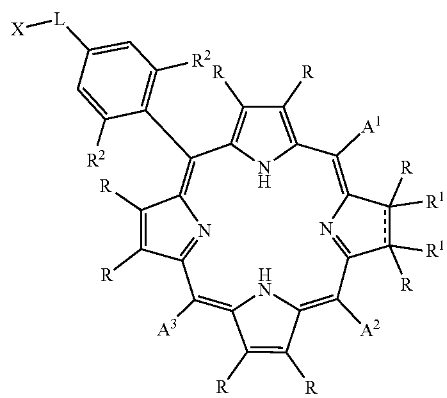

or a salt, or tautomer thereof; wherein R, $R^1$, $R^2$, $A^1$, $A^2$, $A^3$, L, and X are as defined herein.

In certain embodiments, the compound of Formula (I) is of Formula (I-a):

(I-a)

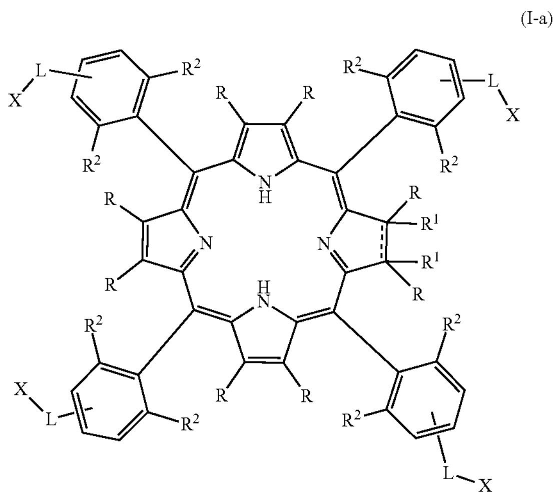

or a salt, or tautomer thereof; wherein R, $R^1$, $R^2$, L, and X are as defined herein.

In certain embodiments, the compound of Formula (I) is of Formula (I-b):

(I-b)

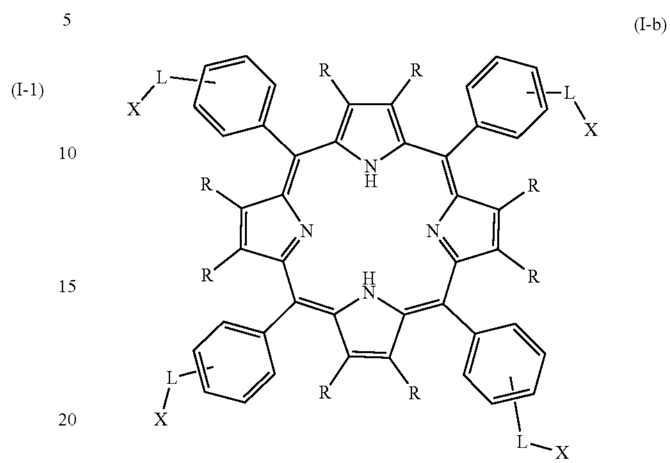

or a salt, or tautomer thereof; wherein R, L, and X are as defined herein.

In certain embodiments, the compound of Formula (I) is of Formula (I-b-1):

(I-b-1)

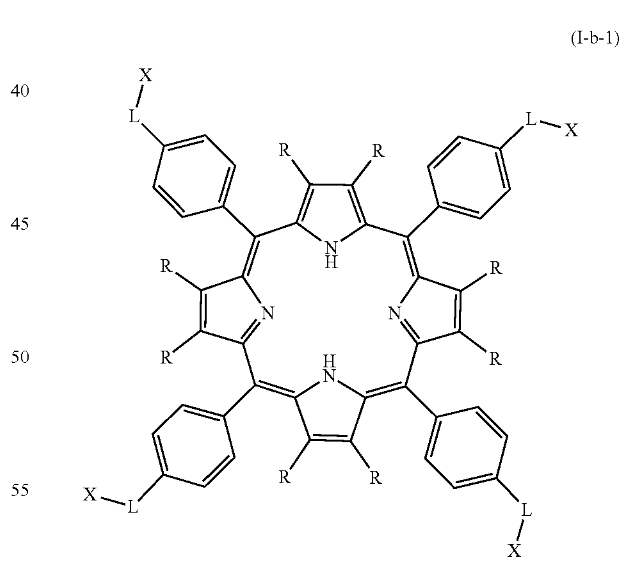

or a salt, or tautomer thereof; wherein R, L, and X are as defined herein.

In certain embodiments, the compound of Formula (I) is of Formula (I-b-2):

(I-b-2)

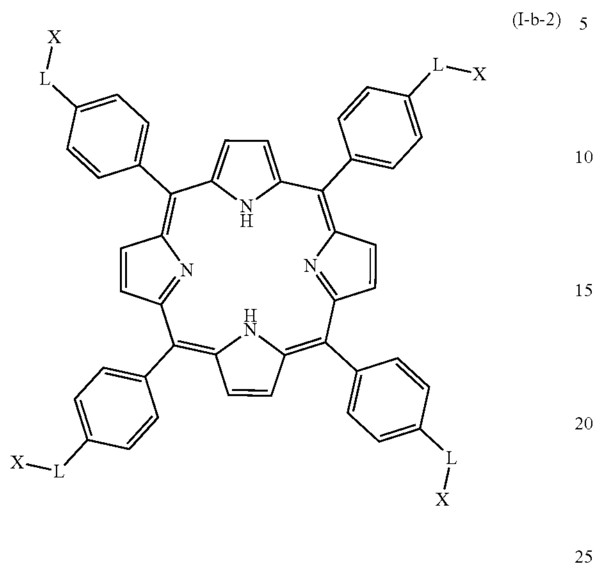

or a salt, or tautomer thereof; wherein L and X are as defined herein.

In certain embodiments, the compound of Formula (I) is of Formula (I-b-3):

(I-b-3)

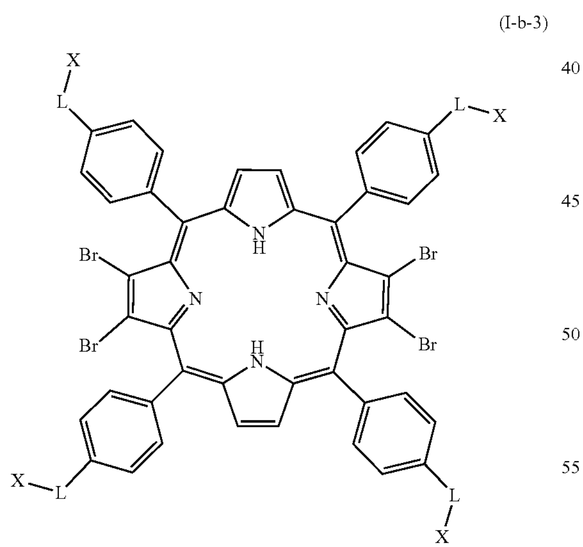

or a salt, or tautomer thereof; wherein L and X are as defined herein.

In certain embodiments, the compound of Formula (I) is of Formula (I-b-4):

(I-b-4)

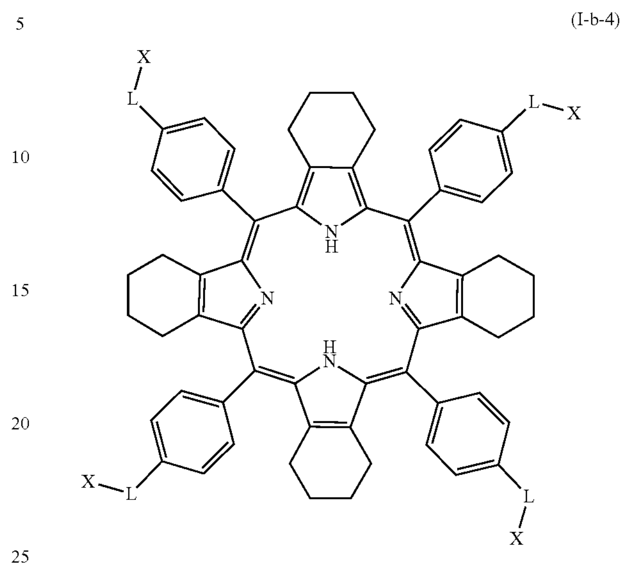

or a salt, or tautomer thereof; wherein L and X are as defined herein.

In certain embodiments, the compound of Formula (I) is of Formula (I-b-5):

(I-b-5)

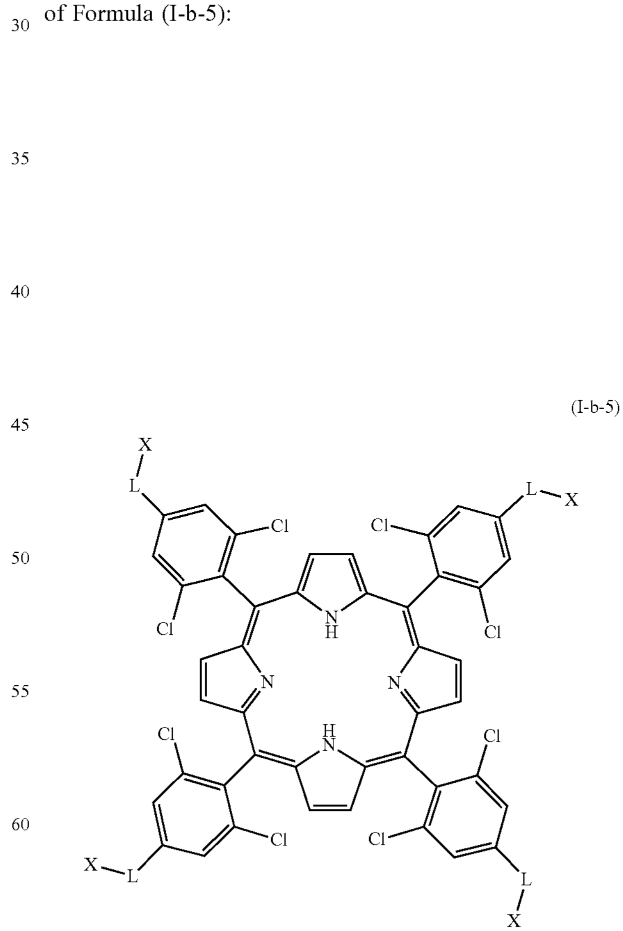

or a salt, or tautomer thereof; wherein L and X are as defined herein.

In certain embodiments, the compound of Formula (I) is of Formula (I-b-6):

(I-b-6)

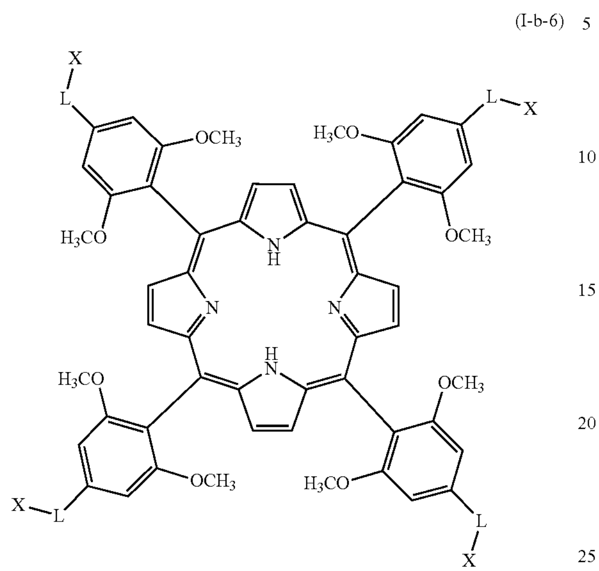

or a salt, or tautomer thereof; wherein L and X are as defined herein.

In certain embodiments, the compound of Formula (I) is of Formula (I-c):

(I-c)

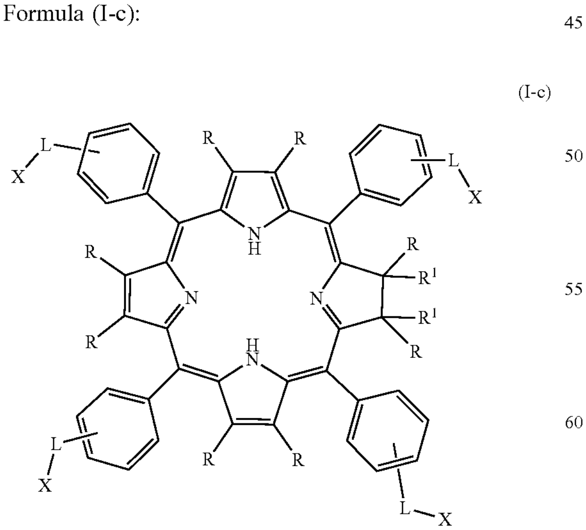

or a salt, or tautomer thereof; wherein R, L, and X are as defined herein.

In certain embodiments, the compound of Formula (I) is of Formula (I-c-1):

(I-c-1)

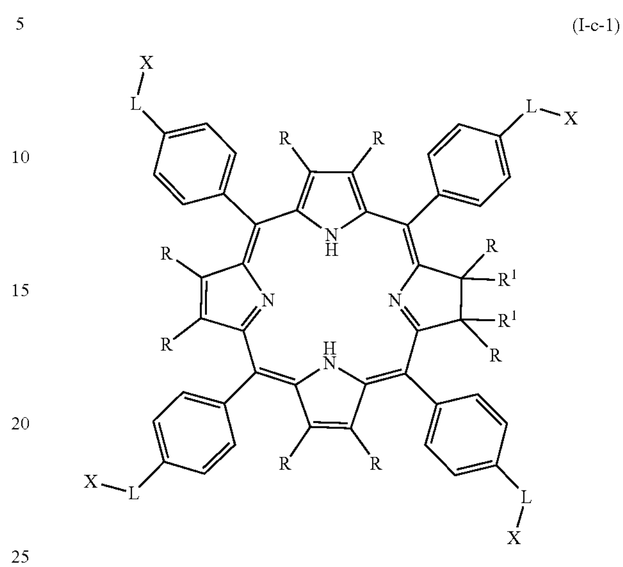

or a salt, or tautomer thereof; wherein R, L, and X are as defined herein.

In certain embodiments, the compound of Formula (I) is of Formula (I-c-2):

(I-c-2)

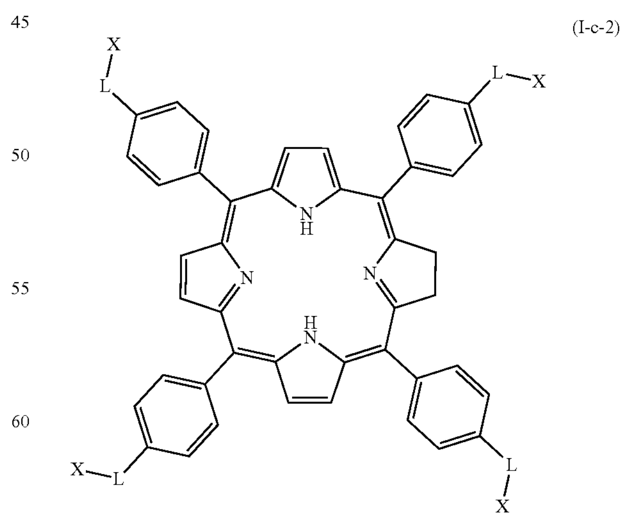

or a salt, or tautomer thereof; wherein L and X are as defined herein.

In certain embodiments, the compound of Formula (I) is of Formula (I-c-3):

(I-c-3)

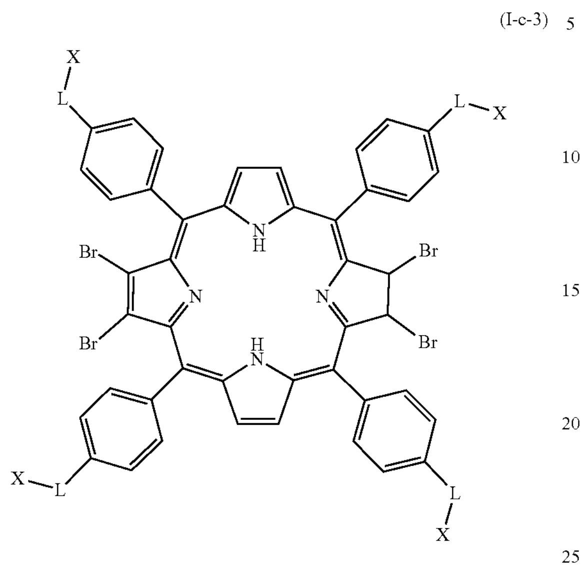

or a salt, or tautomer thereof; wherein L and X are as defined herein.

In certain embodiments, the compound of Formula (I) is of Formula (I-c-4):

(I-c-4)

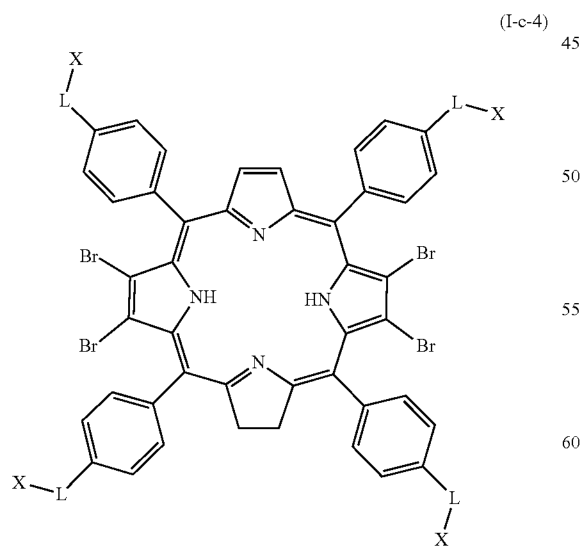

or a salt, or tautomer thereof; wherein L and X are as defined herein.

In certain embodiments, the compound of Formula (I) is of Formula (I-c-5):

(I-c-5)

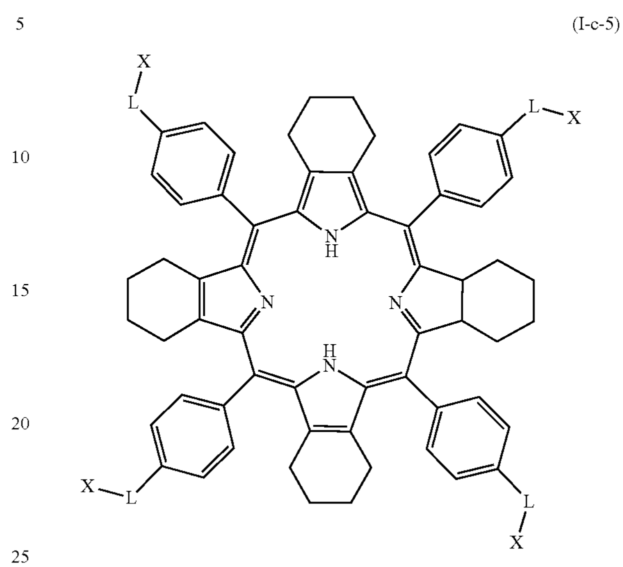

or a salt, or tautomer thereof; wherein L and X are as defined herein.

In certain embodiments, the compound of Formula (I) is of Formula (I-c-6):

(I-c-6)

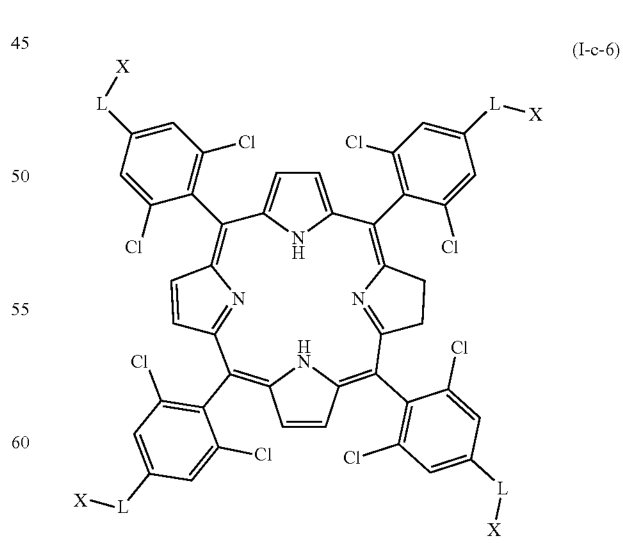

or a salt, or tautomer thereof; wherein L and X are as defined herein.

In certain embodiments, the compound of Formula (I) is of Formula (I-c-7):
(I-c-7)
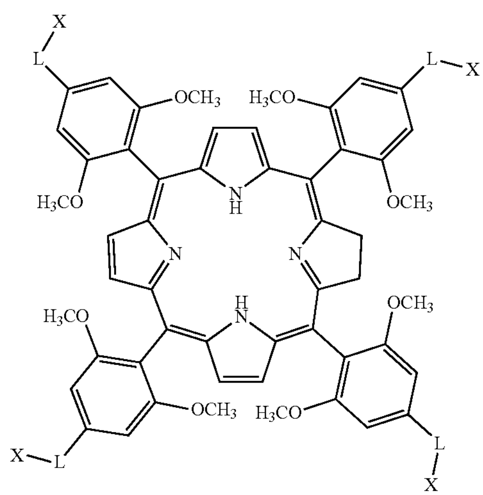
or a salt, or tautomer thereof; wherein L and X are as defined herein.
In certain embodiments, the compound of Formula (I) is of formula:
(1)
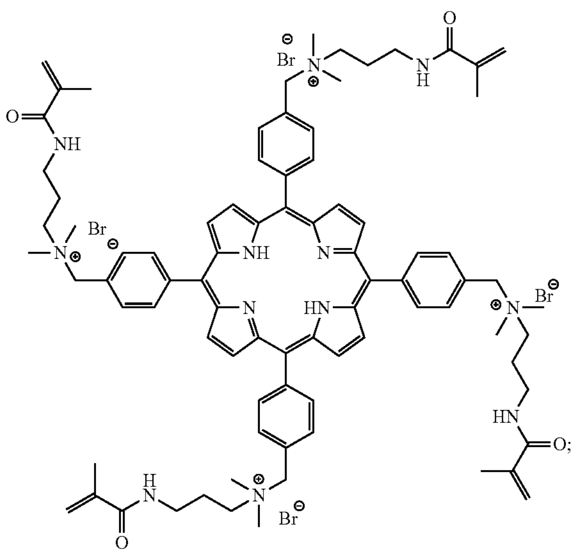
-continued
(2)
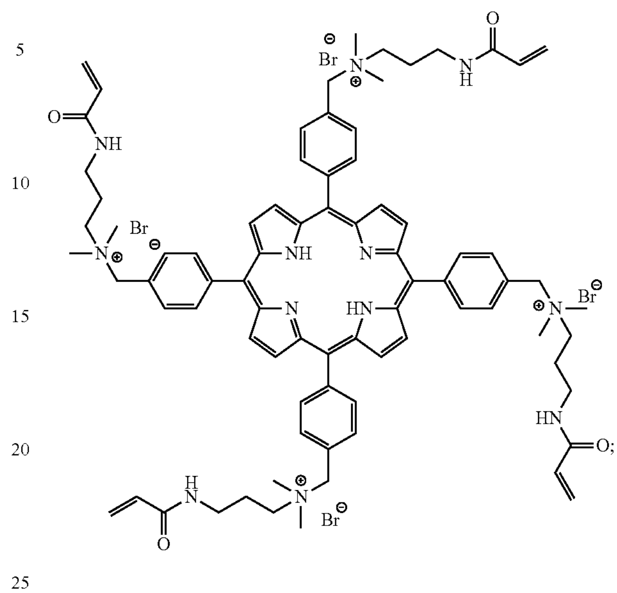
(3)
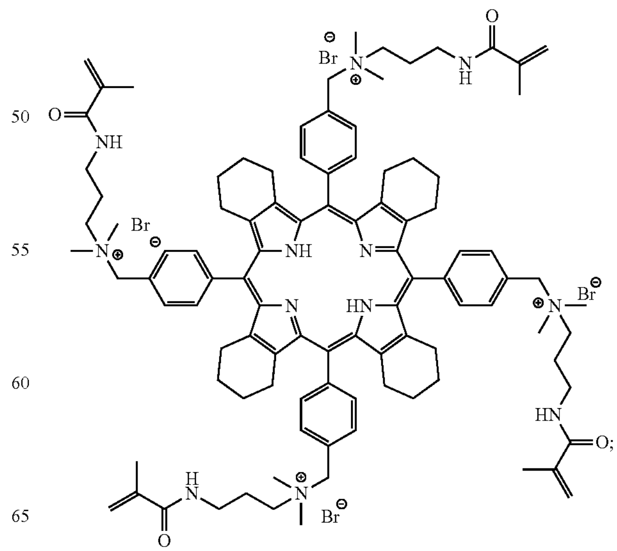

-continued
(4)
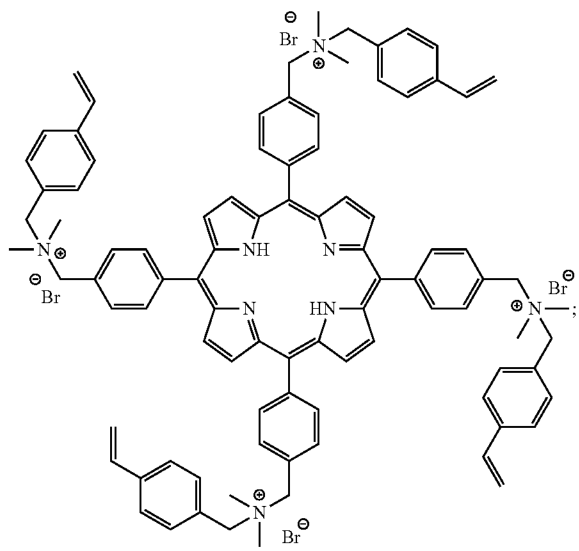
(5)
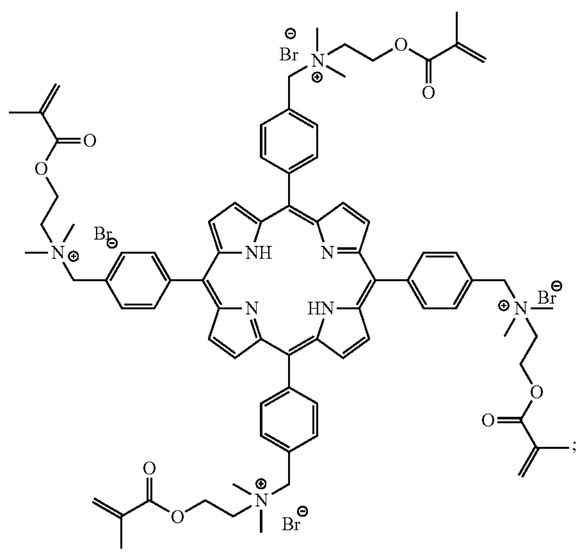
-continued
(6)
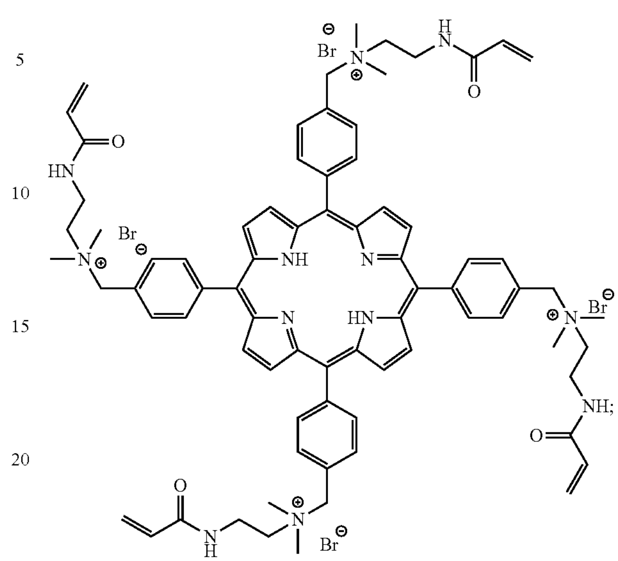
(7)
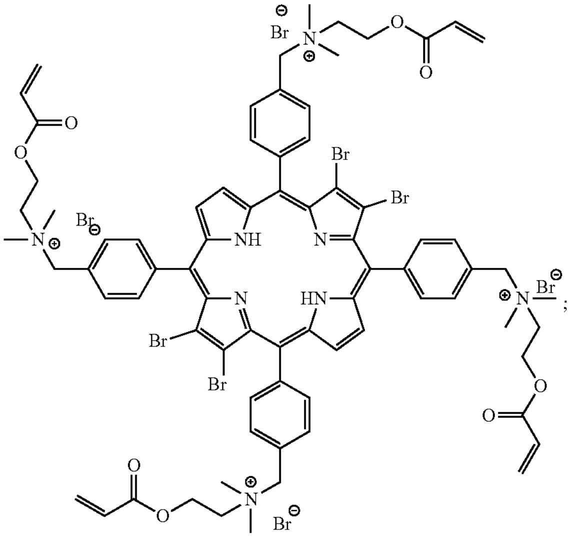

-continued
(15)
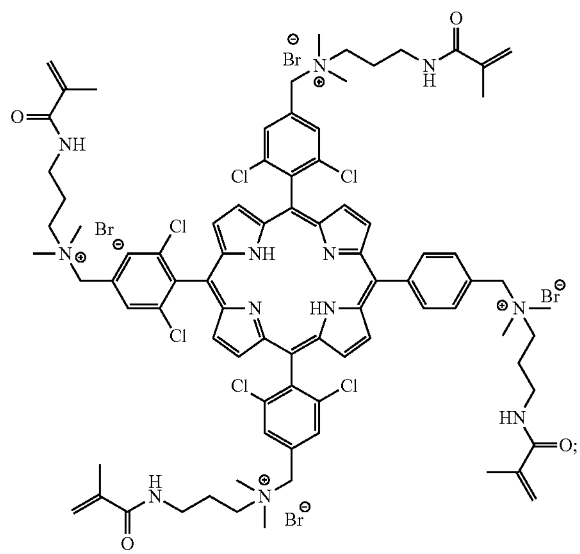
(17)
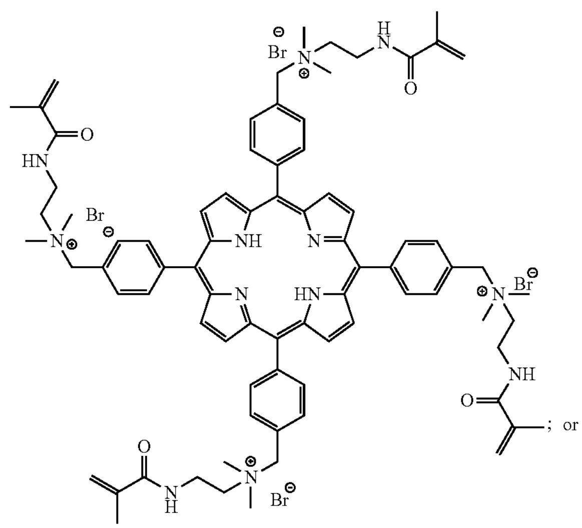
; or
-continued
(19)
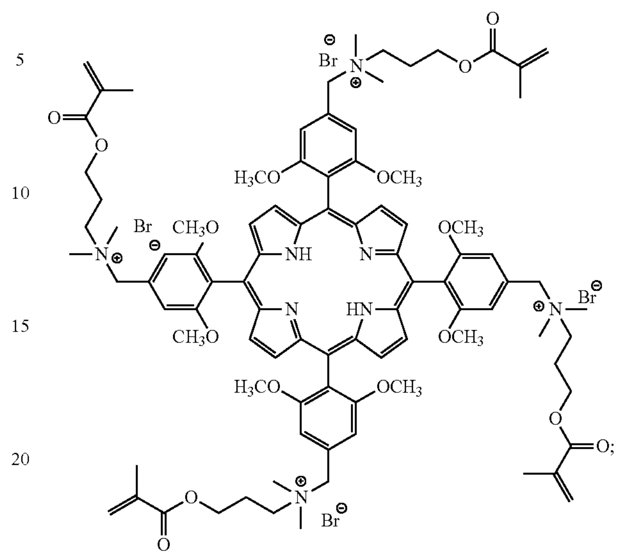
or a salt or tautomer thereof.
In certain embodiments, the compound of Formula (II) is of Formula (II-1):
(II-1)
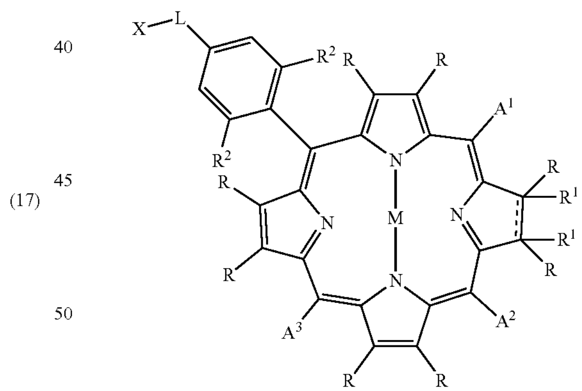
or a salt, or tautomer thereof; wherein M, R, $R^1$, $R^2$, $A^1$, $A^2$, $A^3$, L, and X are as defined herein.

In certain embodiments, the compound of Formula (II) is of Formula (II-a):

(II-a)

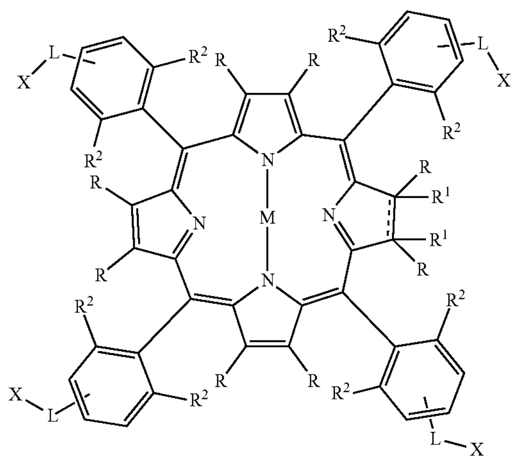

or a salt, or tautomer thereof; wherein M, R, $R^1$, $R^2$, L, and X are as defined herein.

In certain embodiments, the compound of Formula (II) is of Formula (II-bb):

(II-b)

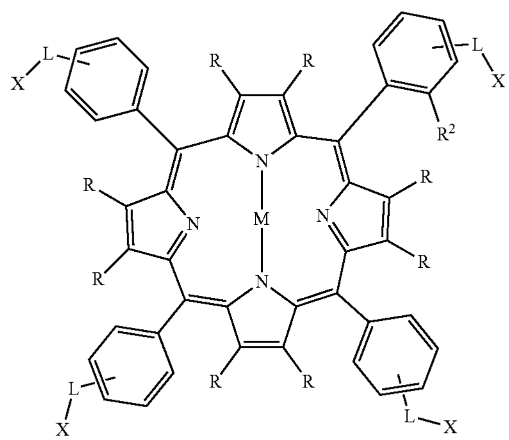

or a salt, or tautomer thereof; wherein M, R, L, and X are as defined herein.

In certain embodiments, the compound of Formula (II) is of Formula (II-b-1):

(II-b-1)

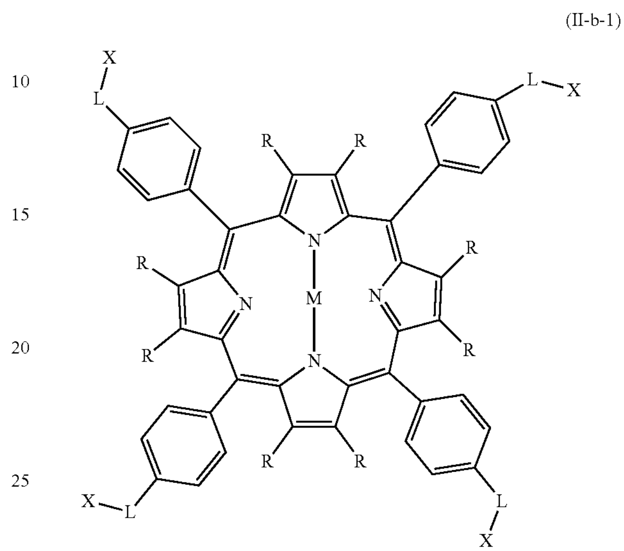

or a salt, or tautomer thereof; wherein M, R, L, and X are as defined herein.

In certain embodiments, the compound of Formula (II) is of Formula (II-b-2):

(II-b-2)

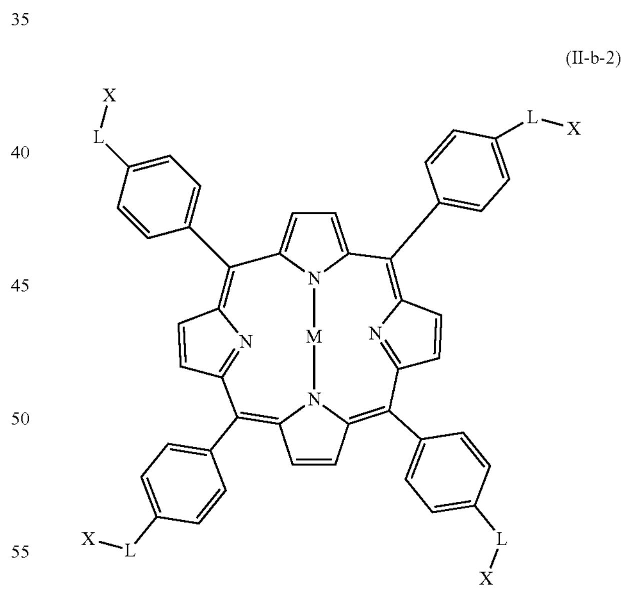

or a salt, or tautomer thereof; wherein M, L and X are as defined herein.

In certain embodiments, the compound of Formula (II) is of Formula (II-b-3):

(II-b-3)

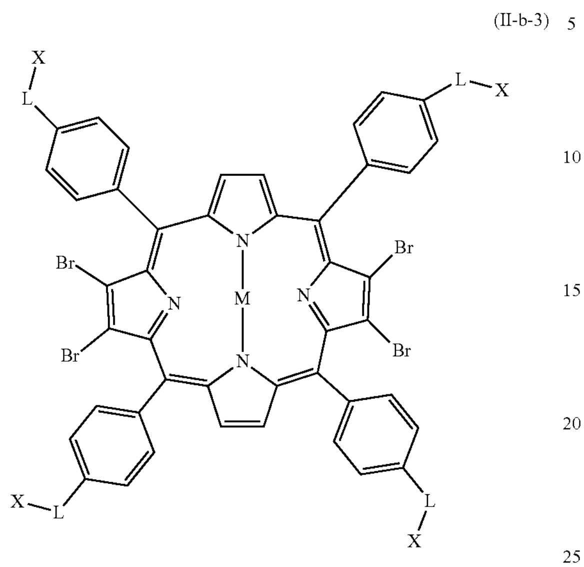

or a salt, or tautomer thereof; wherein M, L and X are as defined herein.

In certain embodiments, the compound of Formula (II) is of Formula (II-b-4):

(II-b-4)

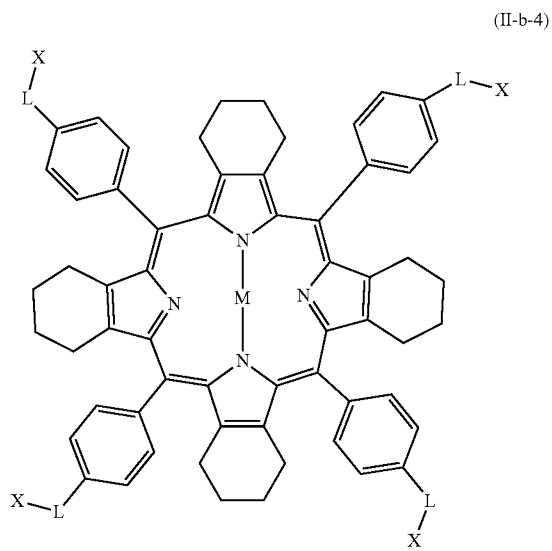

or a salt, or tautomer thereof; wherein M, L and X are as defined herein.

In certain embodiments, the compound of Formula (II) is of Formula (II-b-5):

(II-b-5)

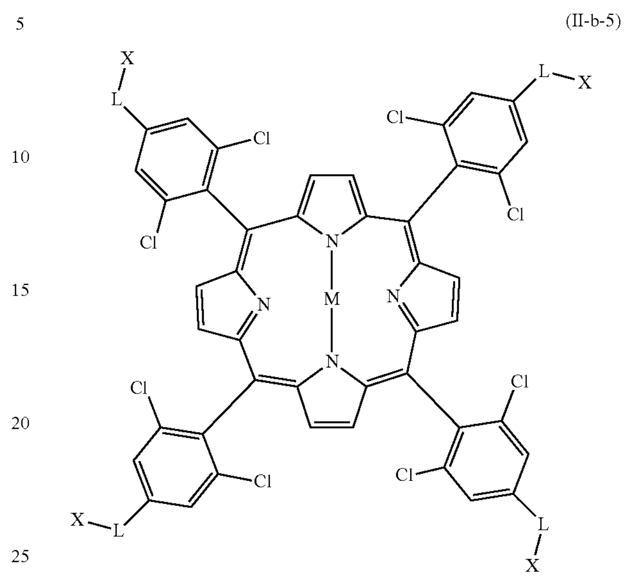

or a salt, or tautomer thereof; wherein M, L and X are as defined herein.

In certain embodiments, the compound of Formula (II) is of Formula (II-b-6):

(II-b-6)

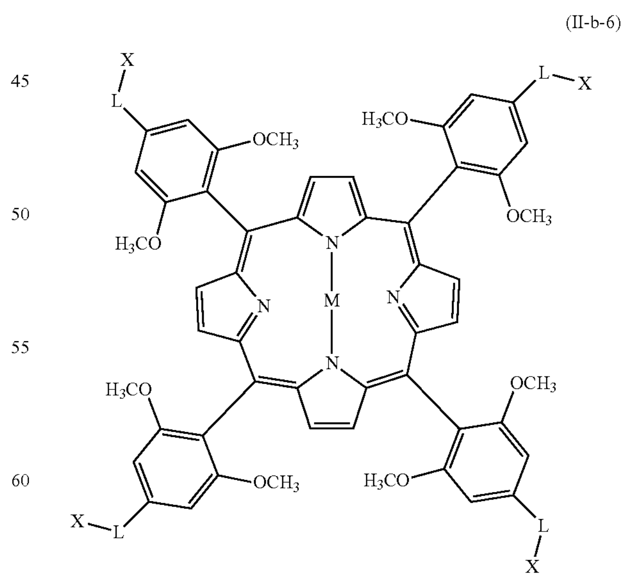

or a salt, or tautomer thereof; wherein M, L and X are as defined herein.

In certain embodiments, the compound of Formula (II) is of Formula (II-c):

(II-c)

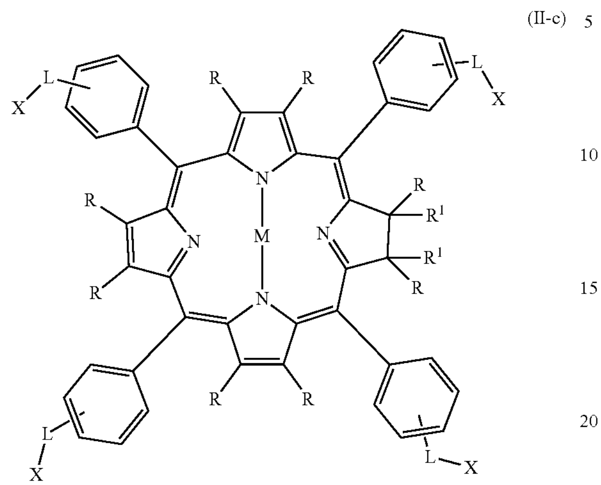

or a salt, or tautomer thereof; wherein M, R, L, and X are as defined herein.

In certain embodiments, the compound of Formula (II) is of Formula (II-c-1):

(II-c-1)

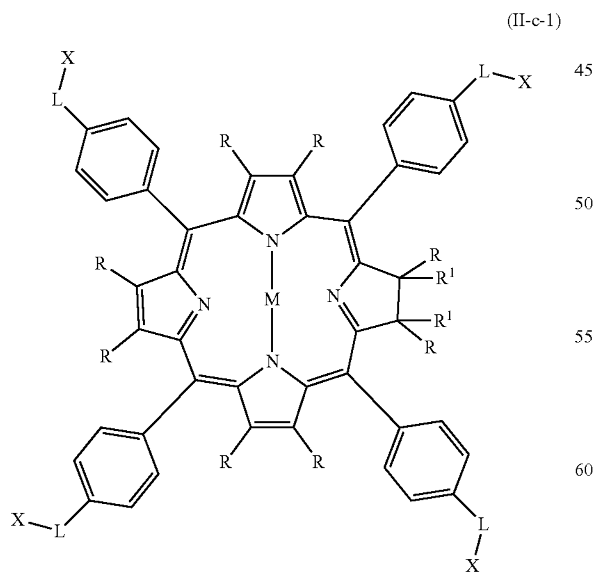

or a salt, or tautomer thereof; wherein M, R, L, and X are as defined herein.

In certain embodiments, the compound of Formula (II) is of Formula (II-c-2):

(II-c-2)

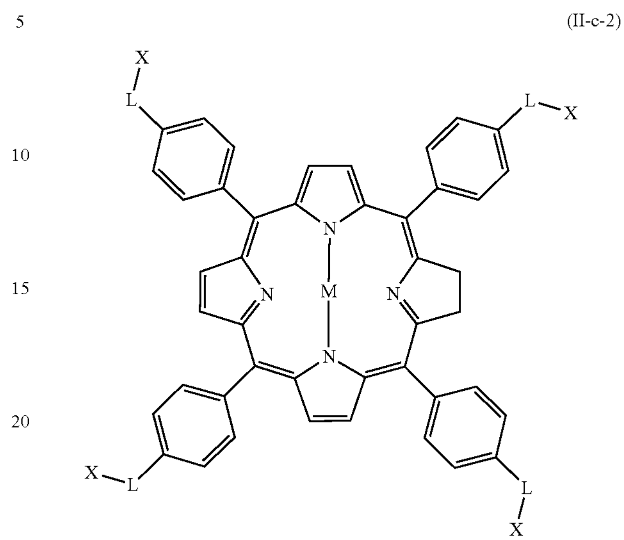

or a salt, or tautomer thereof; wherein M, L and X are as defined herein.

In certain embodiments, the compound of Formula (II) is of Formula (II-c-3):

(II-c-3)

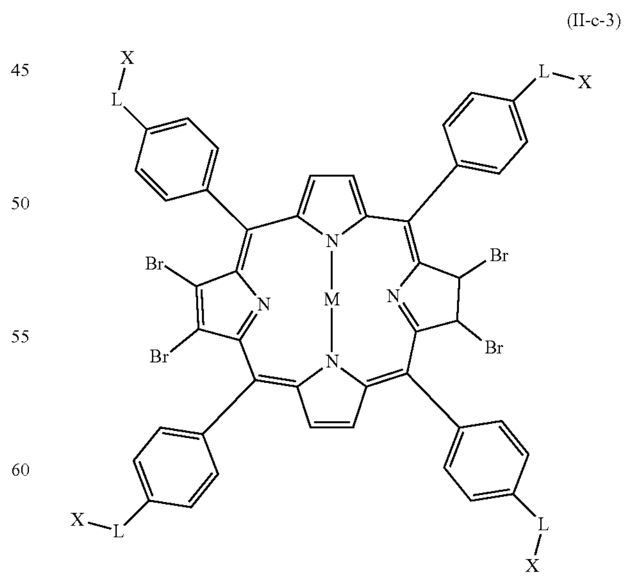

or a salt, or tautomer thereof; wherein M, L and X are as defined herein.

In certain embodiments, the compound of Formula (II) is of Formula (II-c-4):

(II-c-4)

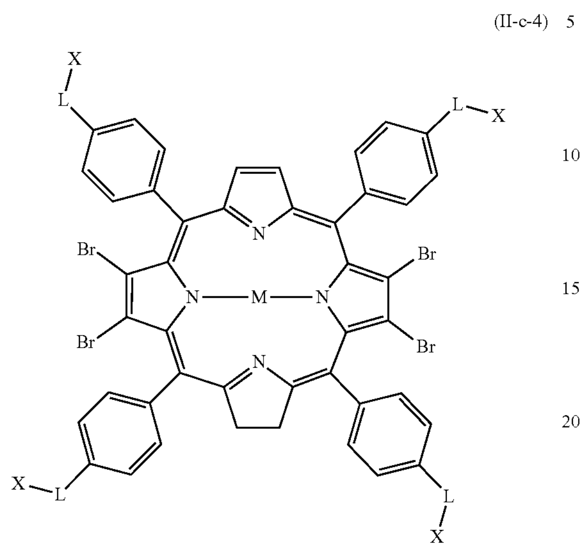

or a salt, or tautomer thereof; wherein M, L and X are as defined herein.

In certain embodiments, the compound of Formula (II) is of Formula (II-c-5):

(II-c-5)

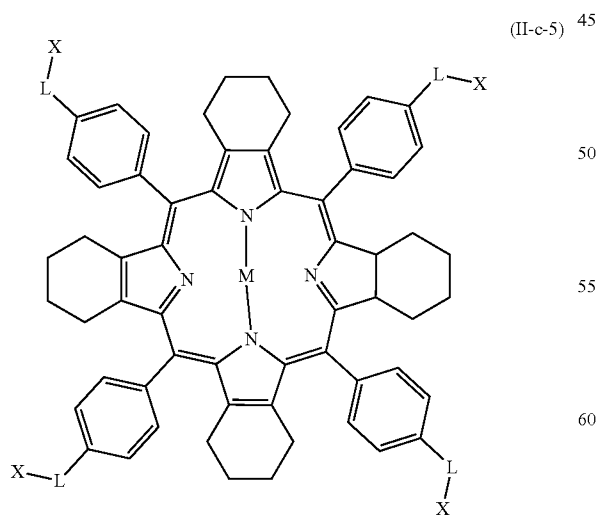

or a salt, or tautomer thereof; wherein M, L and X are as defined herein.

In certain embodiments, the compound of Formula (II) is of Formula (II-c-6):

(II-c-6)

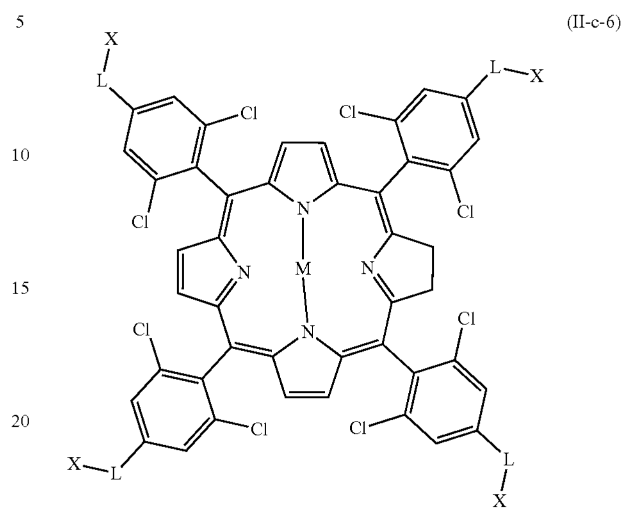

or a salt, or tautomer thereof; wherein M, L and X are as defined herein.

In certain embodiments, the compound of Formula (II) is of Formula (II-c-7):

(II-c-7)

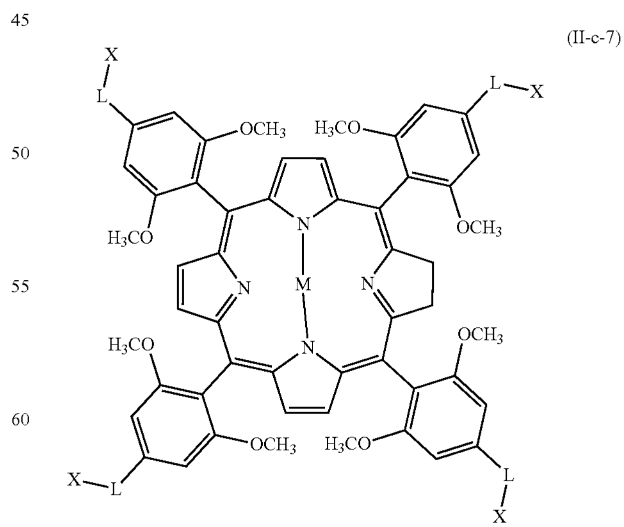

or a salt, or tautomer thereof; wherein M, L and X are as defined herein.

In certain embodiments, the compound of Formula (II) is of formula:
(8)
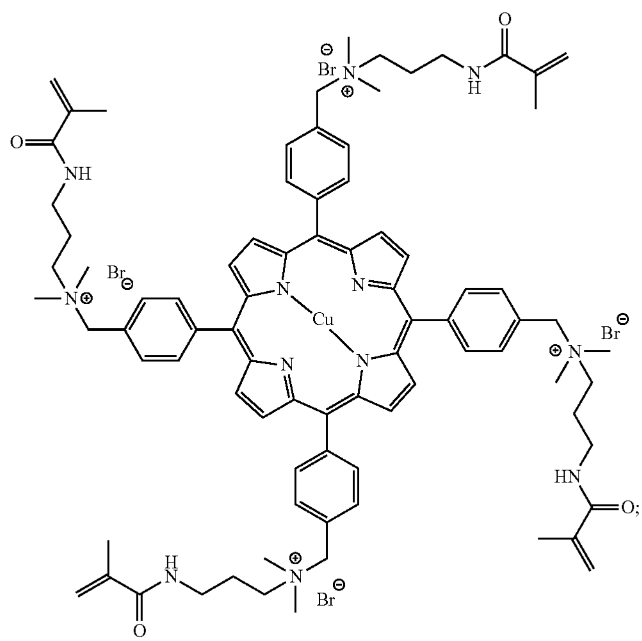
(9)
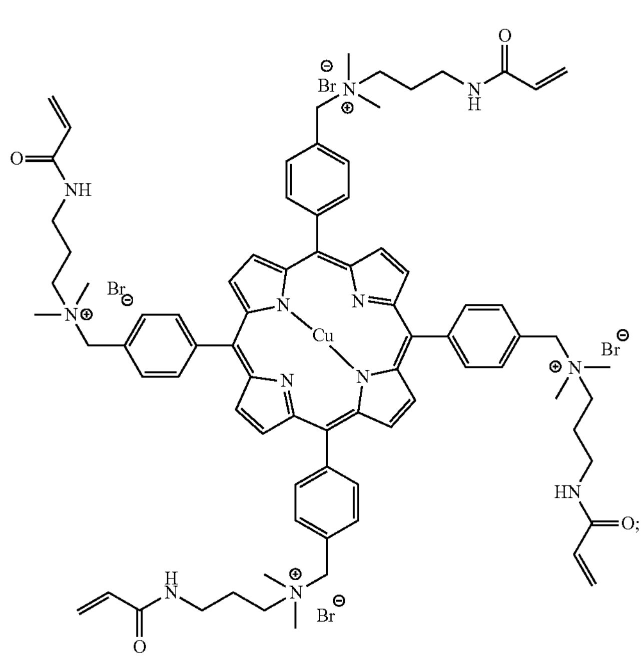

-continued
(10)
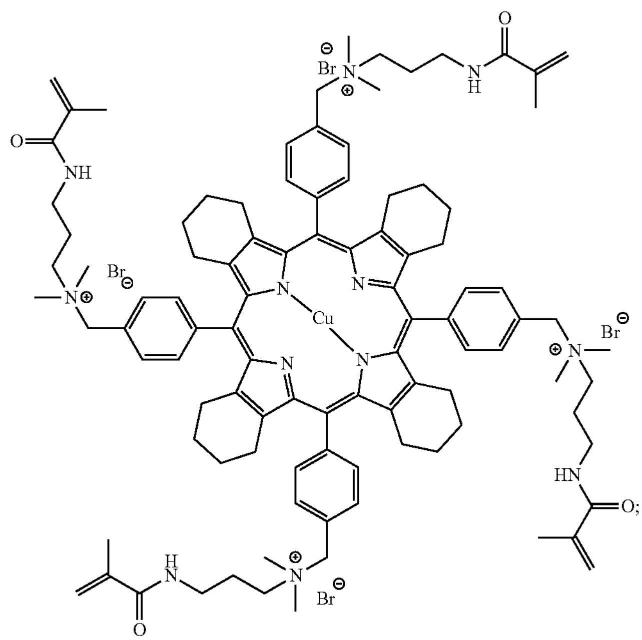
(11)
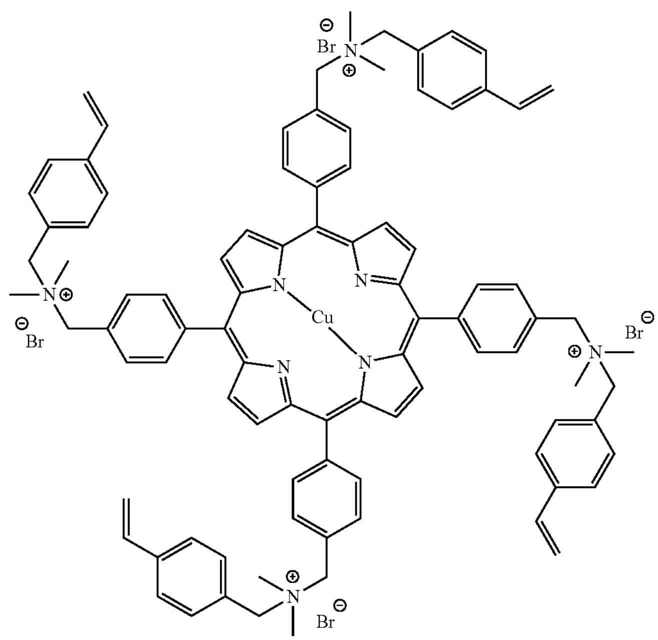
;

-continued
(12)
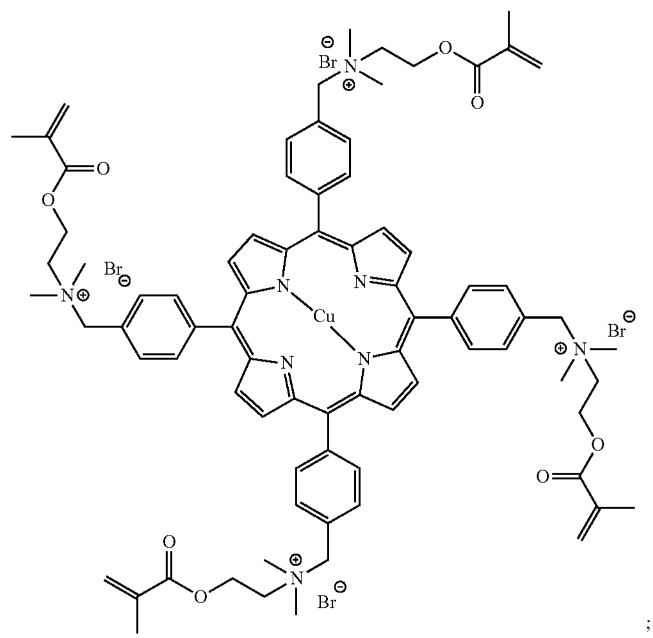
;
(13)
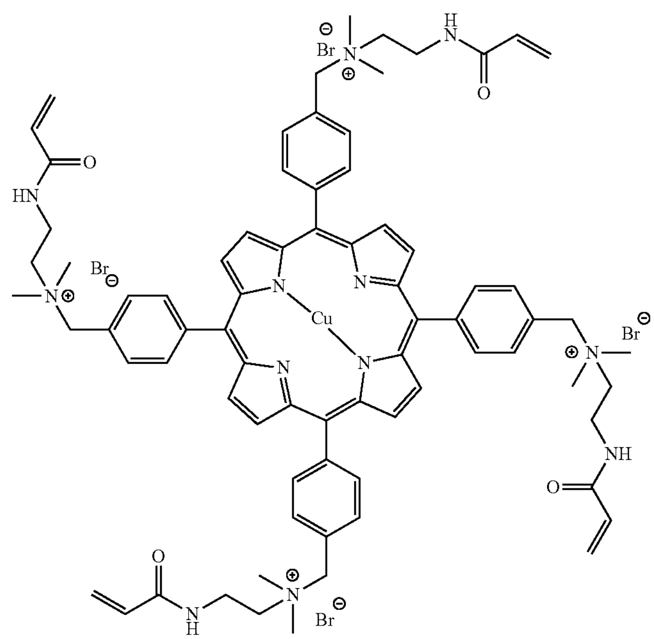
;

-continued
(14)
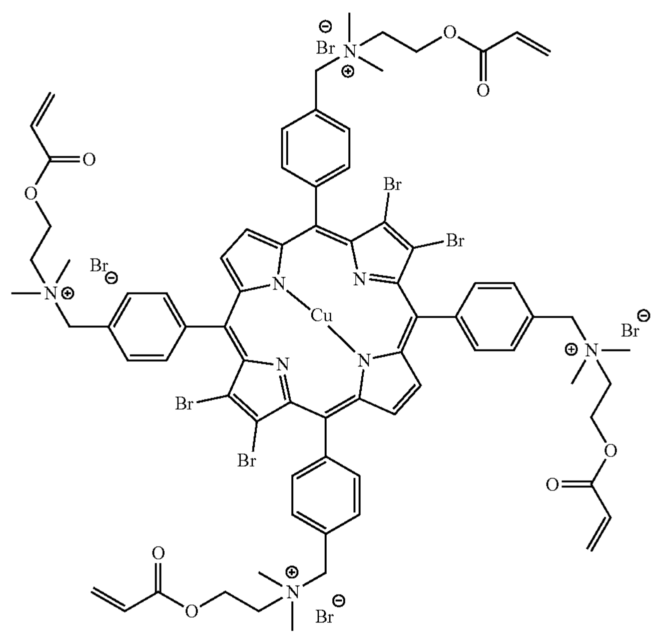
;
(16)
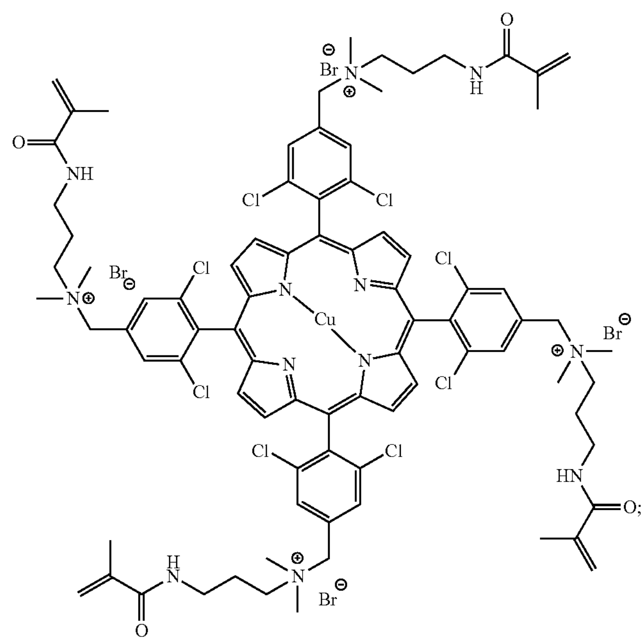
;

-continued (18)

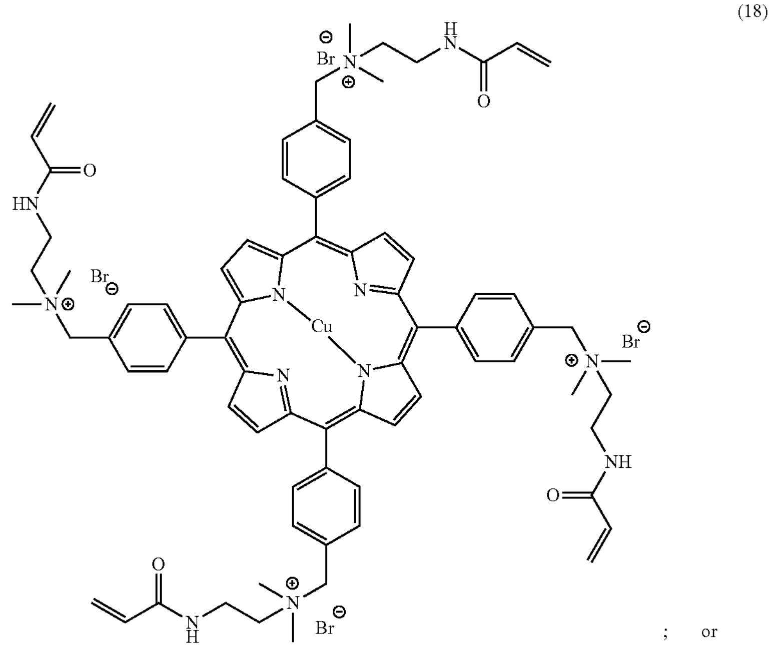

; or (20)

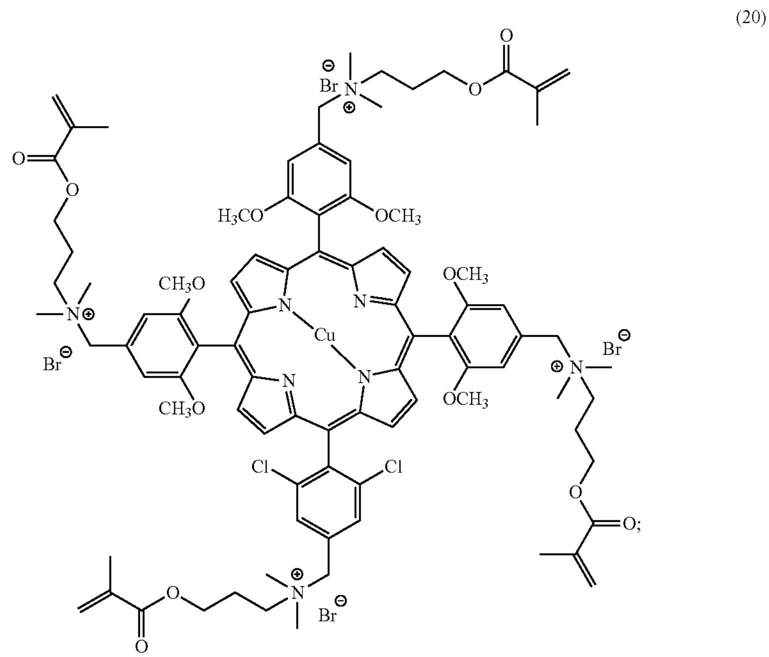

or a salt or tautomer thereof.

Devices

Disclosed are optical devices incorporating the compounds of the disclosure which take advantage of the beneficial properties of the compounds (e.g., selective blue light-blocking, minimal discomfort glare).

In one aspect, disclosed is an optical device comprising a metalloporphyrin or metallochlorin compound, or a salt or tautomer thereof, covalently bound to a polymeric matrix. In certain embodiments, the metalloporphyrin or metallochlorin compound may be any metalloporphyrin or metallochlorin compound.

In certain embodiments, the metalloporphyrin or metallochlorin compound of the device is a compound of Formula (III):

(III)

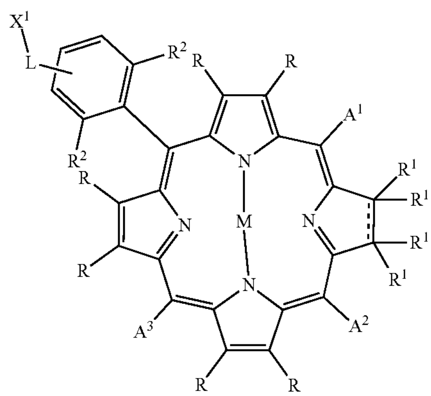

or a salt, or tautomer thereof, wherein:

M is a metal;

each R is independently hydrogen, halogen, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, or two adjacent R groups, together with the atoms to which they are attached, form a substituted or unsubstituted $C_6$-$C_{14}$ aryl, substituted or unsubstituted $C_3$-$C_{14}$ carbocyclyl, substituted or unsubstituted $C_5$-$C_{14}$ heteroaryl, or substituted or unsubstituted $C_3$-$C_{14}$ heterocyclyl;

each $R^1$ is independently hydrogen, halogen, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, or two adjacent R groups, together with the atoms to which they are attached, form a substituted or unsubstituted $C_6$-$C_{14}$ aryl, substituted or unsubstituted $C_3$-$C_{14}$ carbocyclyl, substituted or unsubstituted $C_5$-$C_{14}$ heteroaryl, or substituted or unsubstituted $C_3$-$C_{14}$ heterocyclyl; or one instance of $R^1$ and R on the same carbon form with that carbon a carbonyl;

$A^1$ is hydrogen or a substituted aryl of formula:

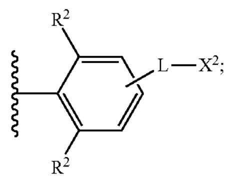

$A^2$ is hydrogen or a substituted aryl of formula:

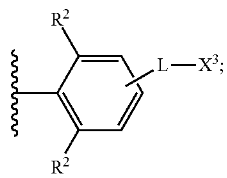

$A^3$ is hydrogen or a substituted aryl of formula:

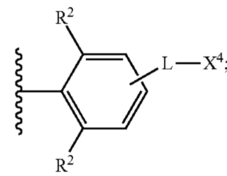

each $R^2$ is independently hydrogen, halogen, —$NO_2$, substituted or unsubstituted alkyl, —$NHR^A$, —$N(R^A)_2$, or —$OR^B$;

====== is a single or double bond, provided that when ====== is double bond, then each $R^1$ is absent;

each L is independently a bond or —$R^3$—$X^L$—$R^4$—;

each $R^3$ and $R^4$ are independently a bond, substituted or unsubstituted $C_1$-$C_{20}$ alkylene, substituted or unsubstituted $C_1$-$C_{20}$ heteroalkylene, substituted or unsubstituted $C_3$-$C_{14}$ carbocyclylene, or substituted or unsubstituted $C_3$-$C_{14}$ heterocyclylene;

each $X^L$ is independently a bond, —O—, —$N(R^A)$—, —$N+(R^A)_2$—, —S—, —C(=O)—, —C(=O)O—, —C(=O)$NR^A$—, —$NR^A$C(=O)—, —$NR^A$C(=O)$R^A$—, —C(=O)$R^A$—, —$NR^A$C(=O)O—, —$NR^A$C(=O)$N(R^A)$—, —OC(=O)—, —OC(=O)O—, —OC(=O)$N(R^A)$—, —$S(O)_2NR^A$—, —$NR^AS(O)_2$—, or a combination thereof;

each of $X^1$, $X^2$, $X^3$, and $X^4$ is independently hydrogen, halogen, substituted or unsubstituted $C_1$-$C_{20}$ alkyl, a polymerizable group, or a group derived from a polymerizable group and covalently bound to the polymeric matrix, wherein at least one of $X^1$, $X^2$, $X^3$, and $X^4$ is derived from a polymerizable group and covalently bound to the polymeric matrix; and each occurrence of $R^A$ is independently hydrogen, substituted or unsubstituted acyl, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, substituted or unsubstituted $C_3$-$C_{14}$ carbocyclyl, substituted or unsubstituted $C_3$-$C_{14}$ heterocyclyl, substituted or unsubstituted $C_6$-$C_{14}$ aryl, substituted or unsubstituted $C_5$-$C_{14}$ heteroaryl, a nitrogen protecting group, or two $R^A$ groups are joined to form a substituted or unsubstituted $C_3$-$C_{14}$ heterocyclyl, or a substituted or unsubstituted $C_5$-$C_{14}$ heteroaryl; and each occurrence of $R^B$ is independently hydrogen, substituted or unsubstituted acyl, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, substituted or unsubstituted $C_3$-$C_{14}$ carbocyclyl, substituted or unsubstituted $C_3$-$C_{14}$ heterocyclyl, substituted or unsubstituted $C_{6-14}$ aryl, or substituted or unsubstituted $C_{5-14}$ heteroaryl.

M

As defined herein, M is a metal. In certain embodiments, M is a transition metal. In certain embodiments, M is copper, vanadium, or cobalt. In certain embodiments, M is copper. In certain embodiments, M is vanadium. In certain embodiments, M is cobalt.

R

As defined herein, each R is independently hydrogen, halogen, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, or two adjacent R groups, together with the atoms to which they are attached, form a substituted or unsubstituted $C_6$-$C_{14}$ aryl, substituted or unsubstituted $C_3$-$C_{14}$ carbocyclyl, substituted or unsubstituted $C_5$-$C_{14}$ heteroaryl, or substituted or unsubstituted $C_3$-$C_{14}$ heterocyclyl.

In certain embodiments, each R is independently hydrogen, halogen, substituted or unsubstituted $C_1$-$C_{20}$ alkyl, or two adjacent R groups, together with the atoms to which they are attached, form a substituted or unsubstituted $C_3$-$C_{14}$ carbocyclyl.

In certain embodiments, each R is independently hydrogen, halogen, or two adjacent R groups, together with the atoms to which they are attached, form a substituted or unsubstituted $C_3$-$C_{14}$ carbocyclyl.

In certain embodiments, each R is independently hydrogen, bromo, chloro, or two adjacent R groups, together with the atoms to which they are attached, form a substituted or unsubstituted $C_3$-$C_{14}$ carbocyclyl.

In certain embodiments, each R is independently hydrogen or halogen. In certain embodiments, each R is independently hydrogen or bromo. In certain embodiments, each R is hydrogen.

In certain embodiments, each R forms a substituted or unsubstituted $C_3$-$C_{14}$ carbocyclyl with the R on the adjacent carbon. In certain embodiments, each R forms an unsubstituted $C_3$-$C_{14}$ carbocyclyl with the R on the adjacent carbon. In certain embodiments, each R forms an unsubstituted 6-membered carbocyclyl with the R on the adjacent carbon.

$R^1$

In certain embodiments, ------ is a single bond, thus providing a chlorin compound.

When ------ is a single bond, each $R^1$ is independently hydrogen, halogen, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, or two adjacent R groups, together with the atoms to which they are attached, form a substituted or unsubstituted $C_6$-$C_{14}$ aryl, substituted or unsubstituted $C_3$-$C_{14}$ carbocyclyl, substituted or unsubstituted $C_5$-$C_{14}$ heteroaryl, or substituted or unsubstituted $C_3$-$C_{14}$ heterocyclyl; or one instance of $R^1$ and R on the same carbon form with that carbon a carbonyl. In certain embodiments, each $R^1$ is independently hydrogen, or substituted or unsubstituted $C_1$-$C_{20}$ alkyl. In certain embodiments, each $R^1$ is independently hydrogen, or unsubstituted $C_1$-$C_{20}$ alkyl. In certain embodiments, each $R^1$ is hydrogen.

$R^2$

As defined herein, each $R^2$ is independently hydrogen, halogen, —$NO_2$, substituted or unsubstituted alkyl, —$NHR^A$, —$N(R^A)_2$, or —$OR^B$. In certain embodiments, each $R^2$ is independently hydrogen, —$OR^B$, or halogen. In certain embodiments, each $R^2$ is independently hydrogen, halogen, substituted or unsubstituted $C_{1-4}$ alkyl, or —$OC_{1-4}$ alkyl. In certain embodiments, each $R^2$ is independently hydrogen, halogen, unsubstituted $C_{1-4}$ alkyl, or —$OC_{1-4}$ alkyl. In certain embodiments, each $R^2$ is independently hydrogen, halogen, or —$OC_{1-4}$ alkyl. In certain embodiments, each $R^2$ is independently hydrogen, —Cl, or —$OCH_3$. In certain embodiments, each $R^2$ is independently hydrogen or —$OC_{1-4}$ alkyl. In certain embodiments, each $R^2$ is independently hydrogen or —$OCH_3$. In certain embodiments, each $R^2$ is independently halogen or —$OC_{1-4}$ alkyl. In certain embodiments, each $R^2$ is independently —Cl or —$OCH_3$. In certain embodiments, each $R^2$ is independently hydrogen or halogen. In certain embodiments, each $R^2$ is hydrogen or —Cl. In certain embodiments, each $R^2$ is independently —Cl. In certain embodiments, each $R^2$ is independently hydrogen. In certain embodiments, each $R^2$ is —$OCH_3$.

$A^1$, $A^2$, and $A^3$

As defined herein, $A^1$ is hydrogen or a substituted aryl of formula:

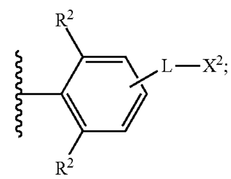

$A^2$ is hydrogen or a substituted aryl of formula:

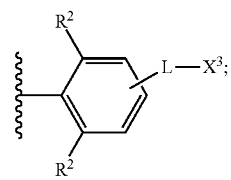

and $A^3$ is hydrogen or a substituted aryl of formula:

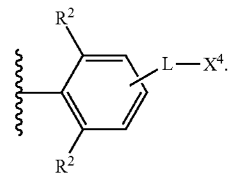

In certain embodiments, $A^1$ is of formula:

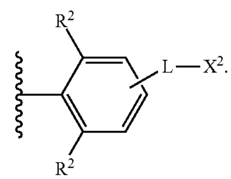

In certain embodiments, $A^1$ is of formula:

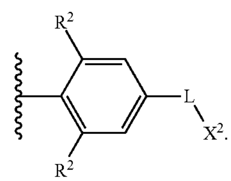

In certain embodiments, $A^1$ is hydrogen.

In certain embodiments, $A^2$ is of formula:

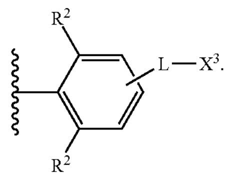

In certain embodiments, $A^1$ is of formula:

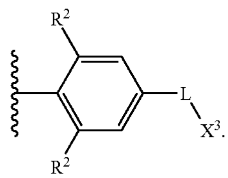

In certain embodiments, $A^2$ is hydrogen.

In certain embodiments, $A^3$ is of formula:

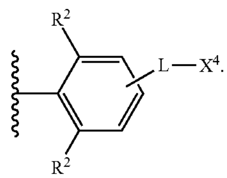

In certain embodiments, $A^1$ is of formula:

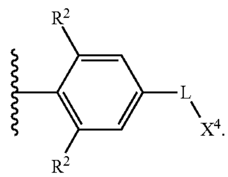

In certain embodiments, $A^3$ is hydrogen.

In certain embodiments, $A^1$, $A^2$, and $A^3$ are each hydrogen. In certain embodiments, $A^1$ is a substituted aryl of formula:

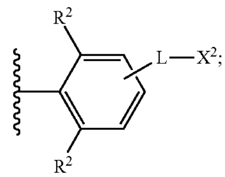

$A^2$ is a substituted aryl of formula:

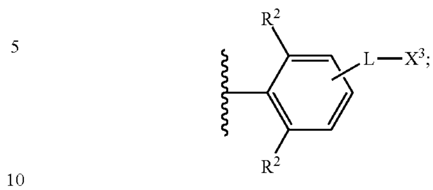

and $A^3$ is a substituted aryl of formula:

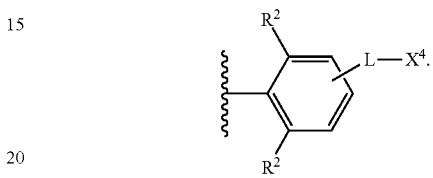

In certain embodiments, $A^1$ is a substituted aryl of formula:

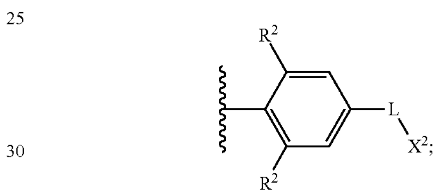

$A^2$ is a substituted aryl of formula:

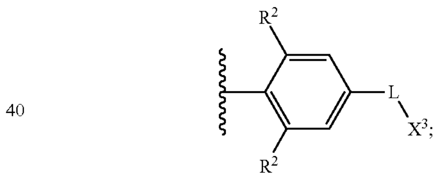

and $A^3$ is a substituted aryl of formula:

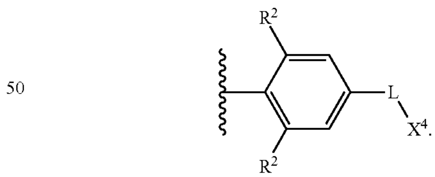

L

As defined herein, each L is independently a bond or $—R^3—X^L—R^4—$; wherein each $R^3$ and $R^4$ are independently a bond, substituted or unsubstituted $C_1$-$C_{20}$ alkylene, substituted or unsubstituted $C_1$-$C_{20}$ heteroalkylene, substituted or unsubstituted $C_3$-$C_{14}$ carbocyclylene, or substituted or unsubstituted $C_3$-$C_{14}$ heterocyclylene; and each $X^L$ is independently a bond, —O—, $—N(R^A)—$, $—N+(R^A)_2—$, —S—, —C(=O)—, —C(=O)O—, $—C(=O)NR^A—$, $—NR^AC(=O)—$, $—NR^AC(=O)R^A—$, $—C(=O)R^A—$, $—NR^AC(=O)O—$, $—NR^AC(=O)N(R^A)—$, —OC(=O)—, —OC(=O)O—, $—OC(=O)N(R^A)—$, $—S(O)_2NR^A—$, $—NR^AS(O)_2—$, or a combination thereof.

In certain embodiments, each L is independently —$R^3$—$X^L$—$R^4$—; wherein each $R^3$ and $R^4$ are independently substituted or unsubstituted $C_1$-$C_{20}$ alkylene, or substituted or unsubstituted $C_1$-$C_{20}$ heteroalkylene; and each $X^L$ is independently a bond, —O—, —N($R^A$)—, —N+($R^A$)$_2$—, —C(═O)—, —NR$^A$C(═O)—, —OC(═O)—, or a combination thereof.

In certain embodiments, each L is independently —$R^3$—$X^L$—$R^4$—; wherein each $R^3$ and $R^4$ are independently substituted or unsubstituted $C_1$-$C_{20}$ alkylene, or substituted or unsubstituted $C_1$-$C_{20}$ heteroalkylene; and each $X^L$ is independently —O—, —N($R^A$)—, —N+($R^A$)$_2$—, —C(═O)—, —NR$^A$C(═O)—, —OC(═O)—, or a combination thereof.

In certain embodiments, each L is independently —$R^3$—$X^L$—$R^4$—; wherein each $R^3$ and $R^4$ are independently a substituted or unsubstituted $C_1$-$C_{20}$ alkylene, or substituted or unsubstituted $C_1$-$C_{20}$ heteroalkylene; and each $X^L$ is independently a bond, —N($R^A$)—, or —N+($R^A$)$_2$—.

In certain embodiments, each L is independently —$R^3$—$X^L$—$R^4$—; wherein each $R^3$ and $R^4$ are independently a substituted or unsubstituted $C_1$-$C_{20}$ alkylene, or substituted or unsubstituted $C_1$-$C_{20}$ heteroalkylene; and each $X^L$ is independently —N($R^A$)— or —N+($R^A$)$_2$—.

In certain embodiments, each L is independently —$R^3$—$X^L$—$R^4$—; wherein each $R^3$ and $R^4$ are independently a substituted or unsubstituted $C_1$-$C_{20}$ alkylene; and each $X^L$ is independently a bond, —N($R^A$)—, or —N+($R^A$)$_2$—. In certain embodiments, each L is independently —$R^3$—$X^L$—$R^4$—; wherein each $R^3$ and $R^4$ are independently a substituted or unsubstituted $C_1$-$C_{20}$ alkylene; and each $X^L$ is independently —N($R^A$)— or —N+($R^A$)$_2$—. In certain embodiments, each L is independently —$R^3$—$X^L$—$R^4$—; wherein each $R^3$ and $R^4$ are independently substituted or unsubstituted $C_{1-3}$ alkylene; and each $X^L$ is independently —N($R^A$)— or —N+($R^A$)$_2$ In certain embodiments, each L is independently unsubstituted $C_{1-3}$ alkylene,

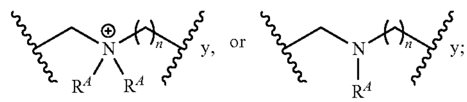

n is 1-6; each occurrence of $R^A$ is independently substituted or unsubstituted $C_1$-$C_{20}$ alkyl; and y labels the site with attachment to one of groups $X^1$-$X^4$. In certain embodiments, each L is independently

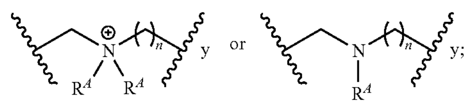

n is 1-6; each occurrence of $R^A$ is independently substituted or unsubstituted $C_1$-$C_{20}$ alkyl; and y labels the site with attachment to one of groups $X^1$-$X^4$.

In certain embodiments, each L is independently unsubstituted $C_{1-3}$ alkylene, or

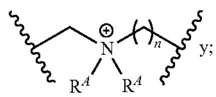

n is 1-6; each occurrence of $R^A$ is independently substituted or unsubstituted $C_1$-$C_{20}$alkyl; and y labels the site with attachment to one of groups $X^1$-$X^4$. In certain embodiments, each L is independently

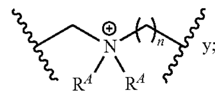

n is 1-6; each occurrence of $R^A$ is independently substituted or unsubstituted $C_1$-$C_{20}$ alkyl; and y labels the site with attachment to one of groups $X^1$-$X^4$.

In certain embodiments, each L is independently unsubstituted $C_{1-3}$ alkylene, or

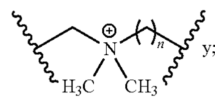

n is 1-3; and y labels the site with attachment to one of groups $X^1$-$X^4$. In certain embodiments, each L is independently

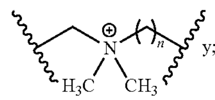

n is 1-3; and y labels the site with attachment to one of groups $X^1$-$X^4$.

In certain embodiments, each L is independently unsubstituted methylene,

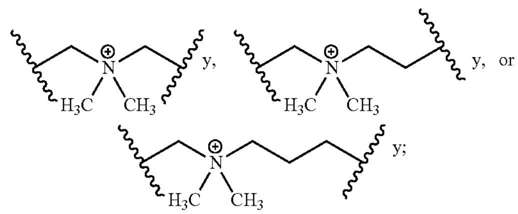

wherein y labels the site with attachment to one of groups $X^1$-$X^4$. In certain embodiments, each L is independently

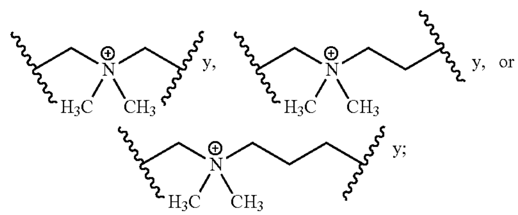

wherein y labels the site with attachment to one of groups $X^1$-$X^4$.

In certain embodiments, each L is independently unsubstituted methylene, or

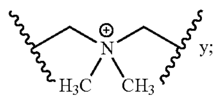

wherein y labels the site with attachment to one of groups $X^1$-$X^4$. In certain embodiments, each L is

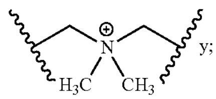

wherein y labels the site with attachment to one of groups $X^1$-$X^4$.

In certain embodiments, each L is independently unsubstituted methylene, or

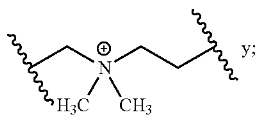

wherein y labels the site with attachment to one of groups $X^1$-$X^4$. In certain embodiments, each L is

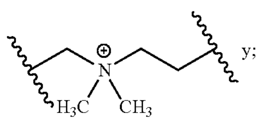 [SMILES: *CC[N+](C)(C)C*]

wherein y labels the site with attachment to one of groups $X^1$-$X^4$.

In certain embodiments, each L is independently unsubstituted methylene, or

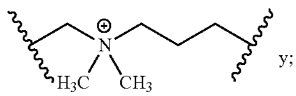

wherein labels the site with attachment to one of groups $X^1$-$X^4$. In certain embodiments, each L is

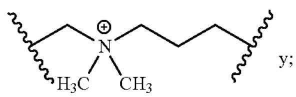

wherein y labels the site with attachment to one of groups $X^1$-$X^4$.

$X^1$-$X^4$

As defined herein, $X^1$, $X^2$, $X^3$, and $X^4$ are each independently hydrogen, halogen, substituted or unsubstituted $C_1$-$C_{20}$ alkyl, a polymerizable group, or derived from a polymerizable group. In certain embodiments, $X^1$, $X^2$, $X^3$, and $X^4$ each represent functional groups that are either polymerizable groups (e.g., acrylate, acrylamide, vinyl sulfone, styrene) or derived from a polymerizable group. When any of $X^1$, $X^2$, $X^3$, and $X^4$ are defined as being derived from a polymerizable group, the polymerizable group has formed a covalent cross-linking with a functional group of another molecule (e.g., polymeric matrix). In certain embodiments, the covalent cross-linking may include polymerization. In certain embodiments, the compounds comprising the polymerizable groups may act as monomers, whereby polymerization of the polymerizable group cross-links the compounds comprising the polymerizable groups with a matrix polymer.

In certain embodiments, at least one of $X^1$, $X^2$, $X^3$, and $X^4$ is a $C_1$-$C_{20}$ haloalkyl. In certain embodiments, at least one of $X^1$, $X^2$, $X^3$, and $X^4$ is a $C_1$-$C_4$ haloalkyl. In certain embodiments, at least one of $X^1$, $X^2$, $X^3$, and $X^4$ is a $C_1$-$C_4$ bromoalkyl. In certain embodiments, at least one of $X^1$, $X^2$, $X^3$, and $X^4$ is a bromomethyl. In certain embodiments, at least one of $X^1$, $X^2$, $X^3$, and $X^4$ is a halogen.

In certain embodiments, $X^1$, $X^2$, $X^3$, and $X^4$ is a halogen only when the L that it is attached to is unsubstituted methylene; and the remaining $X^1$, $X^2$, $X^3$, and $X^4$ groups are polymerizable groups or derived from a polymerizable group as defined herein.

In certain embodiments, $X^1$, $X^2$, $X^3$, and $X^4$ are each independently —Cl, —Br, a polymerizable group, or derived from a polymerizable group. In certain embodiments, $X^1$, $X^2$, $X^3$, and $X^4$ are each independently —Br, a polymerizable group, or derived from a polymerizable group.

In certain embodiments, one of $X^1$, $X^2$, $X^3$, and $X^4$ is derived from a polymerizable group (i.e., it is covalently cross-linked with another molecule, e.g., a polymeric matrix) and the three remaining of $X^1$, $X^2$, $X^3$, and $X^4$ are polymerizable groups. In certain embodiments, two of $X^1$, $X^2$, $X^3$, and $X^4$ are derived from a polymerizable group (i.e., covalently cross-linked with another molecule, e.g., a polymeric matrix) and the two remaining of $X^1$, $X^2$, $X^3$, and $X^4$ are polymerizable groups. In certain embodiments, three of $X^1$, $X^2$, $X^3$, and $X^4$ are derived from a polymerizable group (i.e., covalently cross-linked with another molecule, e.g., a polymeric matrix) and the remaining of $X^1$, $X^2$, $X^3$, and $X^4$ is a polymerizable group. In certain embodiments, each of $X^1$, $X^2$, $X^3$, and $X^4$ are derived from a polymerizable group (i.e., covalently cross-linked with another molecule, e.g., a polymeric matrix).

In certain embodiments, each of $X^1$, $X^2$, $X^3$, and $X^4$ is independently a substituted or unsubstituted acrylate, a substituted or unsubstituted methacrylate, a substituted or unsubstituted acrylamide, a substituted or unsubstituted methacrylamide, a substituted or unsubstituted styrene, a substituted or unsubstituted vinyl sulfone, or substituted or unsubstituted alkenyl; or derived from a substituted or unsubstituted acrylate, a substituted or unsubstituted methacrylate, a substituted or unsubstituted acrylamide, a substituted or unsubstituted methacrylamide, a substituted or unsubstituted styrene, a substituted or unsubstituted vinyl sulfone, or substituted or unsubstituted alkenyl, and covalently bound to the polymeric matrix.

In certain embodiments, three of $X^1$, $X^2$, $X^3$, and $X^4$ is independently a substituted or unsubstituted acrylate, a substituted or unsubstituted methacrylate, a substituted or unsubstituted acrylamide, a substituted or unsubstituted methacrylamide, a substituted or unsubstituted styrene, a substituted or unsubstituted vinyl sulfone, or substituted or unsubstituted alkenyl; and one of $X^1$, $X^2$, $X^3$, and $X^4$ is derived from a substituted or unsubstituted acrylate, a substituted or unsubstituted methacrylate, a substituted or unsubstituted acrylamide, a substituted or unsubstituted methacrylamide, a substituted or unsubstituted styrene, a substituted or unsubstituted vinyl sulfone, or substituted or unsubstituted alkenyl, and covalently bound to the polymeric matrix.

In certain embodiments, two of $X^1$, $X^2$, $X^3$, and $X^4$ is independently a substituted or unsubstituted acrylate, a substituted or unsubstituted methacrylate, a substituted or unsubstituted acrylamide, a substituted or unsubstituted methacrylamide, a substituted or unsubstituted styrene, a substituted or unsubstituted vinyl sulfone, or substituted or unsubstituted alkenyl; and two of $X^1$, $X^2$, $X^3$, and $X^4$ is derived from a substituted or unsubstituted acrylate, a substituted or unsubstituted methacrylate, a substituted or unsubstituted acrylamide, a substituted or unsubstituted methacrylamide, a substituted or unsubstituted styrene, a substituted or unsubstituted vinyl sulfone, or substituted or unsubstituted alkenyl, and covalently bound to the polymeric matrix.

In certain embodiments, one of $X^1$, $X^2$, $X^3$, and $X^4$ is independently a substituted or unsubstituted acrylate, a substituted or unsubstituted methacrylate, a substituted or unsubstituted acrylamide, a substituted or unsubstituted methacrylamide, a substituted or unsubstituted styrene, a substituted or unsubstituted vinyl sulfone, or substituted or unsubstituted alkenyl; and three of $X^1$, $X^2$, $X^3$, and $X^4$ is derived from a substituted or unsubstituted acrylate, a substituted or unsubstituted methacrylate, a substituted or unsubstituted acrylamide, a substituted or unsubstituted methacrylamide, a substituted or unsubstituted styrene, a substituted or unsubstituted vinyl sulfone, or substituted or unsubstituted alkenyl, and covalently bound to the polymeric matrix.

In certain embodiments, each of $X^1$, $X^2$, $X^3$, and $X^4$ is derived from a substituted or unsubstituted acrylate, a substituted or unsubstituted methacrylate, a substituted or unsubstituted acrylamide, a substituted or unsubstituted methacrylamide, a substituted or unsubstituted styrene, a substituted or unsubstituted vinyl sulfone, or substituted or unsubstituted alkenyl, and covalently bound to the polymeric matrix.

In certain embodiments, one of $X^1$, $X^2$, $X^3$, and $X^4$ is independently a substituted or unsubstituted acrylate, a substituted or unsubstituted methacrylate, a substituted or unsubstituted acrylamide, a substituted or unsubstituted methacrylamide, or a substituted or unsubstituted styrene; and three of $X^1$, $X^2$, $X^3$, and $X^4$ is derived from a substituted or unsubstituted acrylate, a substituted or unsubstituted methacrylate, a substituted or unsubstituted acrylamide, a substituted or unsubstituted methacrylamide, or a substituted or unsubstituted styrene, and covalently bound to the polymeric matrix.

In certain embodiments, each of $X^1$, $X^2$, $X^3$, and $X^4$ is derived from a substituted or unsubstituted acrylate, a substituted or unsubstituted methacrylate, a substituted or unsubstituted acrylamide, a substituted or unsubstituted methacrylamide, or a substituted or unsubstituted styrene, and covalently bound to the polymeric matrix.

In certain embodiments, each of $X^1$, $X^2$, $X^3$, and $X^4$ is independently —Cl, —Br,

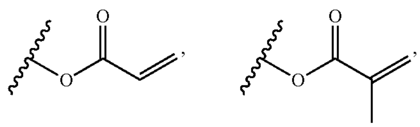

-continued

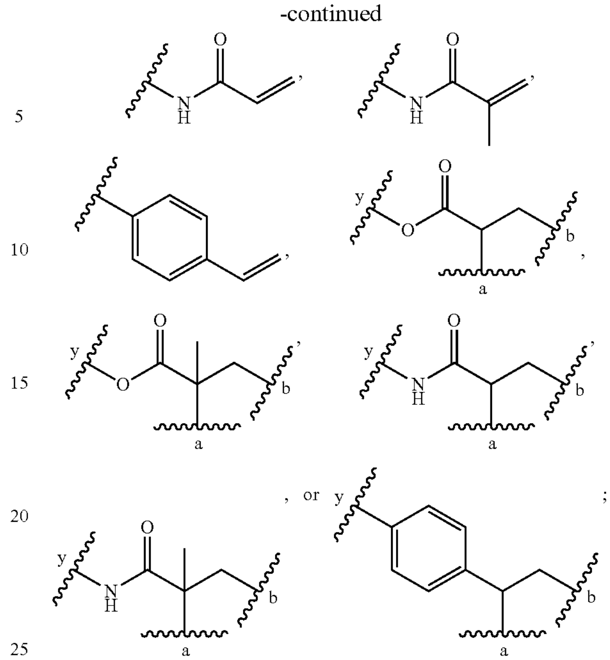

, or ;

wherein y labels the site with attachment to group L and a and b label sites with covalent attachment to the polymeric matrix.

In certain embodiments, each of $X^1$, $X^2$, $X^3$, and $X^4$ is independently

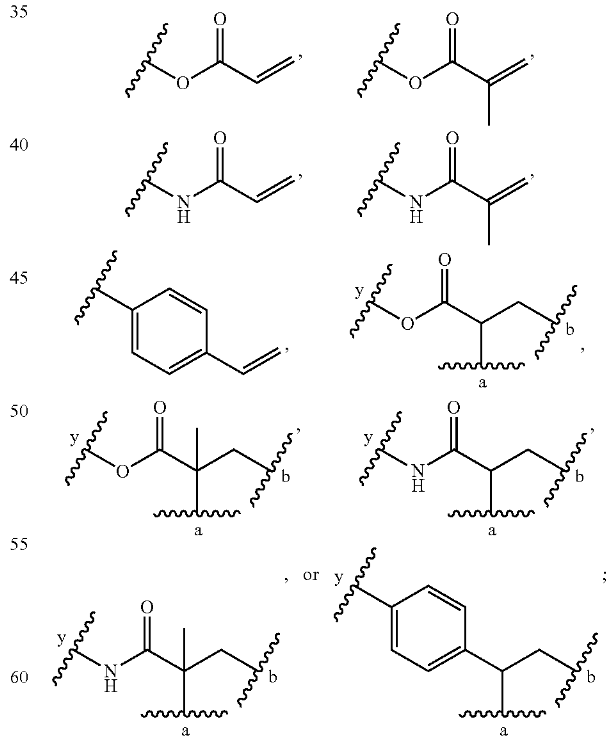

, or ;

wherein y labels the site with attachment to group L and a and b label sites with covalent attachment to the polymeric matrix.

In certain embodiments, three of $X^1$, $X^2$, $X^3$, and $X^4$ are

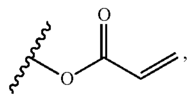 [SMILES: *OC(=O)C=C]

and one of $X^1$, $X^2$, $X^3$, and $X^4$ is

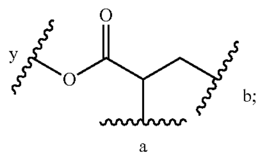 [SMILES: *CC(*)C(=O)O*]

wherein y labels the site with attachment to group L and a and b label sites with covalent attachment to the polymeric matrix. In certain embodiments, two of $X^1$, $X^2$, $X^3$, and $X^4$ are

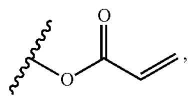 [SMILES: *OC(=O)C=C]

and two of $X^1$, $X^2$, $X^3$, and $X^4$ are

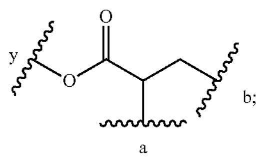 [SMILES: *CC(*)C(=O)O*]

wherein y labels the site with attachment to group L and a and b label sites with covalent attachment to the polymeric matrix. In certain embodiments, one of $X^1$, $X^2$, $X^3$, and $X^4$ is

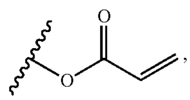

and three of $X^1$, $X^2$, $X^3$, and $X^4$ are

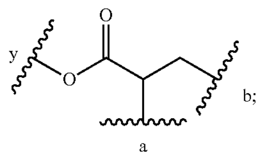 [SMILES: *CC(*)C(=O)O*]

wherein y labels the site with attachment to group L and a and b label sites with covalent attachment to the polymeric matrix.

In certain embodiments, each of $X^1$, $X^2$, $X^3$, and $X^4$ is

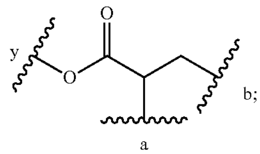 [SMILES: *CC(*)C(=O)O*]

wherein y labels the site with attachment to group L and a and b label sites with covalent attachment to the polymeric matrix.

In certain embodiments, three of $X^1$, $X^2$, $X^3$, and $X^4$ are

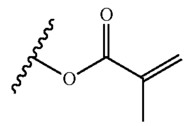

and one of $X^1$, $X^2$, $X^3$, and $X^4$ is

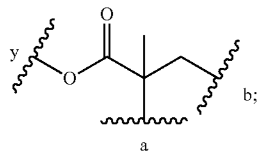 [SMILES: *CC(*)(C)C(=O)O*]

wherein y labels the site with attachment to group L and a and b label sites with covalent attachment to the polymeric matrix. In certain embodiments, two of $X^1$, $X^2$, $X^3$, and $X^4$ are

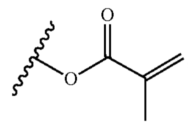

and two of $X^1$, $X^2$, $X^3$, and $X^4$ are

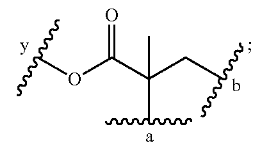 [SMILES: *CC(*)(C)C(=O)O*]

wherein y labels the site with attachment to group L and a and b label sites with covalent attachment to the polymeric matrix. In certain embodiments, one of $X^1$, $X^2$, $X^3$, and $X^4$ is

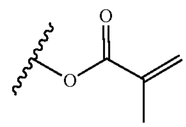

and three of $X^1$, $X^2$, $X^3$, and $X^4$ are

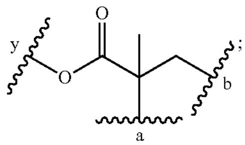 [SMILES: *CC(*)(C)C(=O)O*]

wherein y labels the site with attachment to group L and a and b label sites with covalent attachment to the polymeric matrix.

In certain embodiments, each of $X^1$, $X^2$, $X^3$, and $X^4$ is

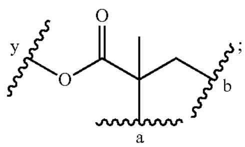 [SMILES: *CC(*)(C)C(=O)O*]

wherein y labels the site with attachment to group L and a and b label sites with covalent attachment to the polymeric matrix.

In certain embodiments, three of $X^1$, $X^2$, $X^3$, and $X^4$ are

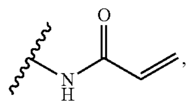 [SMILES: *NC(=O)C=C]

and one of $X^1$, $X^2$, $X^3$, and $X^4$ is

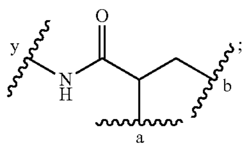 [SMILES: *CC(*)C(=O)N*]

wherein y labels the site with attachment to group L and a and b label sites with covalent attachment to the polymeric matrix. In certain embodiments, two of $X^1$, $X^2$, $X^3$, and $X^4$ are

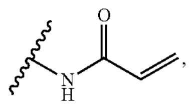 [SMILES: *NC(=O)C=C]

and two of $X^1$, $X^2$, $X^3$, and $X^4$ are

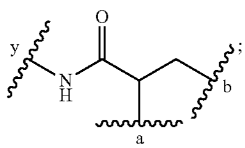 [SMILES: *CC(*)C(=O)N*]

wherein y labels the site with attachment to group L and a and b label sites with covalent attachment to the polymeric matrix. In certain embodiments, one of $X^1$, $X^2$, $X^3$, and $X^4$ is

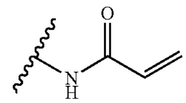

and three of $X^1$, $X^2$, $X^3$, and $X^4$ are

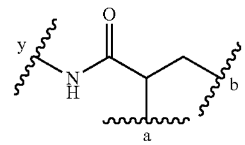

wherein y labels the site with attachment to group L and a and b label sites with covalent attachment to the polymeric matrix. In certain embodiments, each of $X^1$, $X^2$, $X^3$, and $X^4$ is

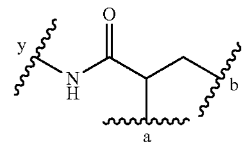

wherein y labels the site with attachment to group L and a and b label sites with covalent attachment to the polymeric matrix.

In certain embodiments, three of $X^1$, $X^2$, $X^3$, and $X^4$ are

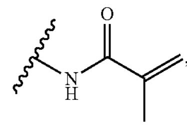

and one of $X^1$, $X^2$, $X^3$, and $X^4$ is

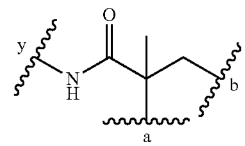

wherein y labels the site with attachment to group L and a and b label sites with covalent attachment to the polymeric matrix. In certain embodiments, two of $X^1$, $X^2$, $X^3$, and $X^4$ are

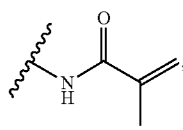 [SMILES: *NC(=O)C(=C)C]

and two of $X^1$, $X^2$, $X^3$, and $X^4$ are

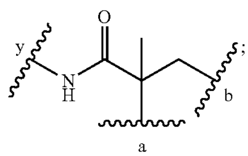 [SMILES: *CC(*)(C)C(=O)N*]

wherein y labels the site with attachment to group L and a and b label sites with covalent attachment to the polymeric matrix. In certain embodiments, one of $X^1$, $X^2$, $X^3$, and $X^4$ is

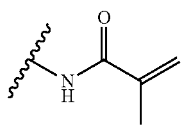

and three of $X^1$, $X^2$, $X^3$, and $X^4$ are

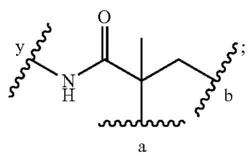 [SMILES: *CC(*)(C)C(=O)N*]

wherein y labels the site with attachment to group L and a and b label sites with covalent attachment to the polymeric matrix.

In certain embodiments, each of $X^1$, $X^2$, $X^3$, and $X^4$ is

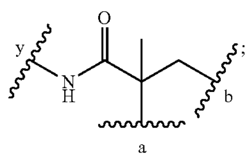 [SMILES: *CC(*)(C)C(=O)N*]

wherein y labels the site with attachment to group L and a and b label sites with covalent attachment to the polymeric matrix.

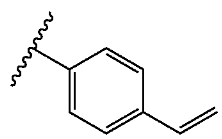

In certain embodiments, three of $X^1$, $X^2$, $X^3$, and $X^4$ are and one of $X^1$, $X^2$, $X^3$, and $X^4$ is

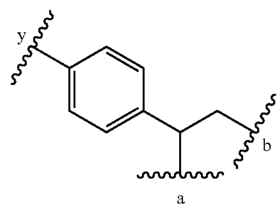

wherein y labels the site with attachment to group L and a and b label sites with covalent attachment to the polymeric matrix. In certain embodiments, two of $X^1$, $X^2$, $X^3$, and $X^4$ are

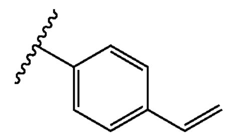

and two of $X^1$, $X^2$, $X^3$, and $X^4$ are

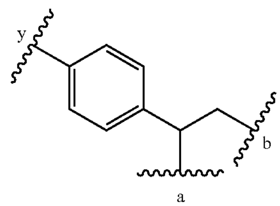

wherein y labels the site with attachment to group L and a and b label sites with covalent attachment to the polymeric matrix. In certain embodiments, one of $X^1$, $X^2$, $X^3$, and $X^4$ is

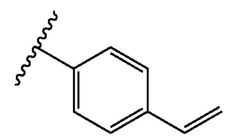

and three of $X^1$, $X^2$, $X^3$, and $X^4$ are

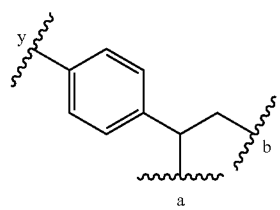

wherein y labels the site with attachment to group L and a and b label sites with covalent attachment to the polymeric matrix. In certain embodiments, each of $X^1$, $X^2$, $X^3$, and $X^4$ is

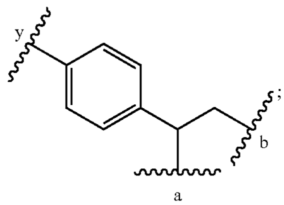 [SMILES: *CC(*)c1ccc(*)cc1]

wherein y labels the site with attachment to group L and a and b label sites with covalent attachment to the polymeric matrix.

Embodiments of Formula (III)

In certain embodiments, the compound of Formula (III) is of Formula (III-1):

(III-1)

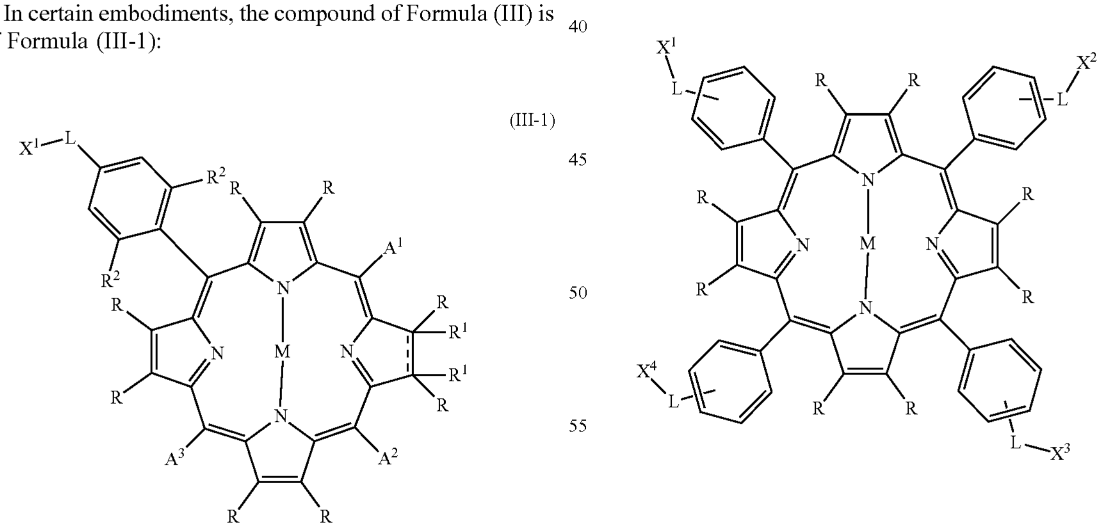

or a salt, or tautomer thereof; wherein M, R, $R^1$, $R^2$, $A^1$, $A^2$, $A^3$, L, and $X^1$ are as defined herein.

In certain embodiments, the compound of Formula (III) is of Formula (III-a):

(III-a)

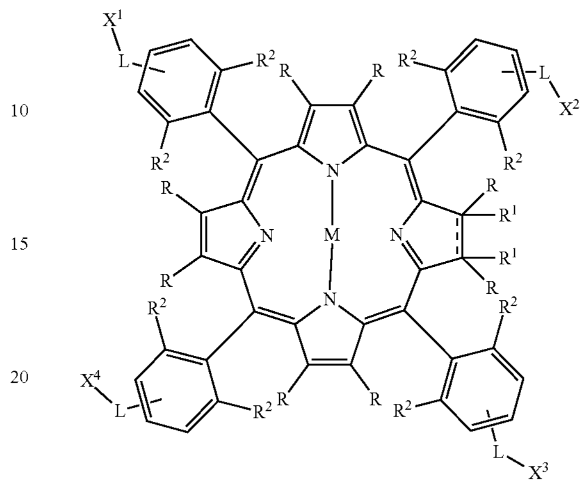

or a salt, or tautomer thereof; wherein M, R, $R^1$, $R^2$, L, and $X^1$-$X^4$ are as defined herein.

In certain embodiments, the compound of Formula (III) is of Formula (III-b):

(III-b)

or a salt, or tautomer thereof; wherein M, R, L, and $X^1$-$X^4$ are as defined herein.

In certain embodiments, the compound of Formula (III) is of Formula (III-b-1):

(III-b-1)

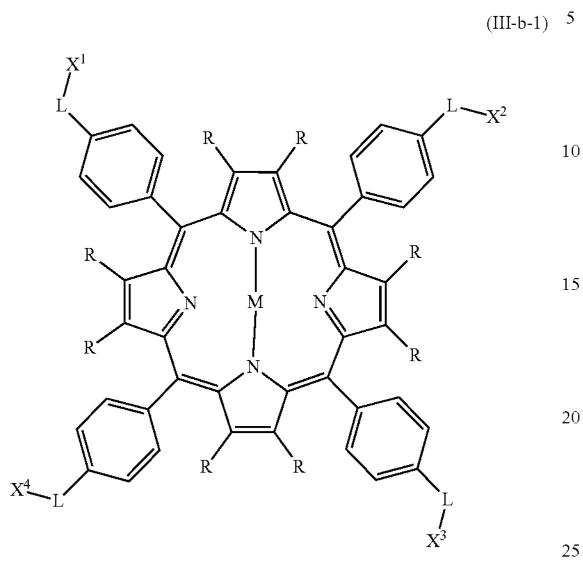

or a salt, or tautomer thereof; wherein M, R, L, and $X^1$-$X^4$ are as defined herein.

In certain embodiments, the compound of Formula (III) is of Formula (III-b-2):

(III-b-2)

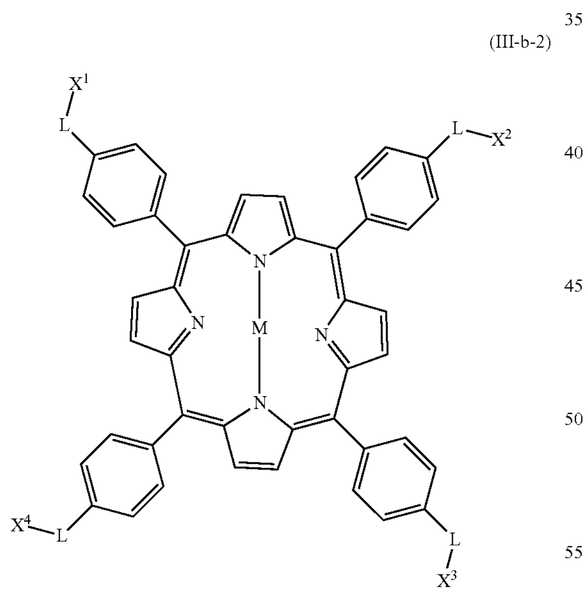

or a salt, or tautomer thereof; wherein M, L and $X^1$-$X^4$ are as defined herein.

In certain embodiments, the compound of Formula (III) is of Formula (III-b-3):

(III-b-3)

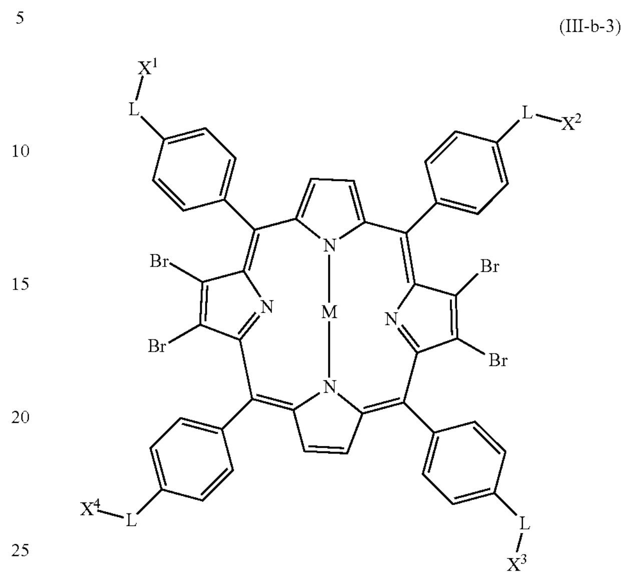

or a salt, or tautomer thereof; wherein M, L and $X^1$-$X^4$ are as defined herein.

In certain embodiments, the compound of Formula (III) is of Formula (III-b-4):

(III-b-4)

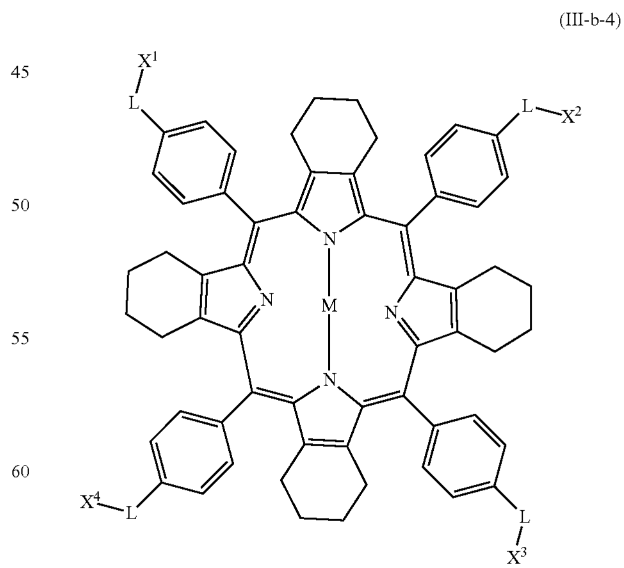

or a salt, or tautomer thereof; wherein M, L and $X^1$-$X^4$ are as defined herein.

In certain embodiments, the compound of Formula (III) is of Formula (III-b-5):

(III-b-5)

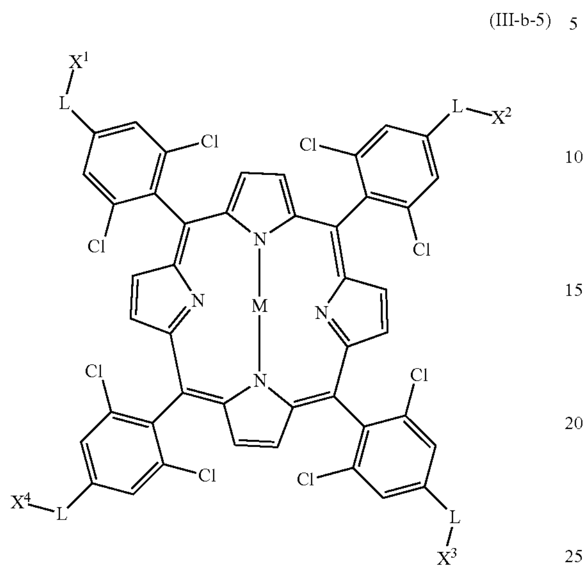

or a salt, or tautomer thereof; wherein M, L and $X^1$-$X^4$ are as defined herein.

In certain embodiments, the compound of Formula (III) is of Formula (III-b-6):

(III-b-6)

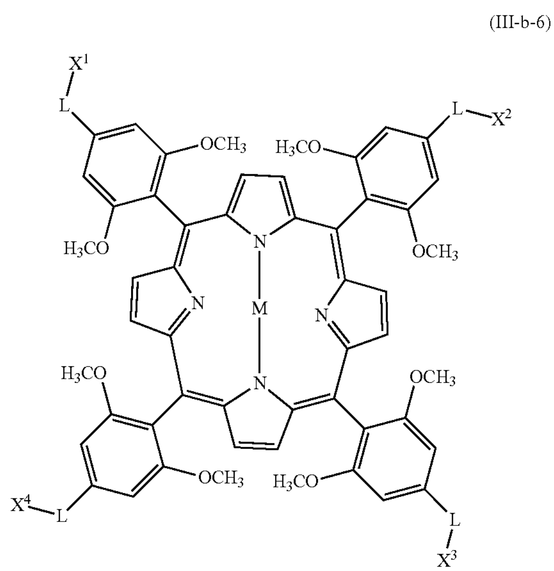

or a salt, or tautomer thereof; wherein M, L and $X^1$-$X^4$ are as defined herein.

In certain embodiments, the compound of Formula (III) is of Formula (III-c):

(III-c)

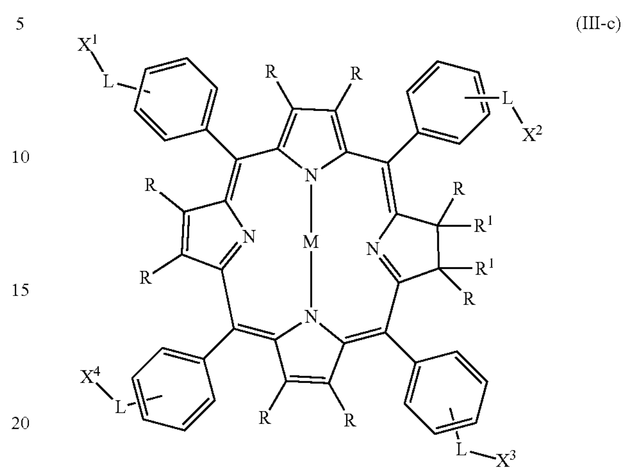

or a salt, or tautomer thereof; wherein M, R, L, and $X^1$-$X^4$ are as defined herein.

In certain embodiments, the compound of Formula (III) is of Formula (III-c-1):

(III-c-1)

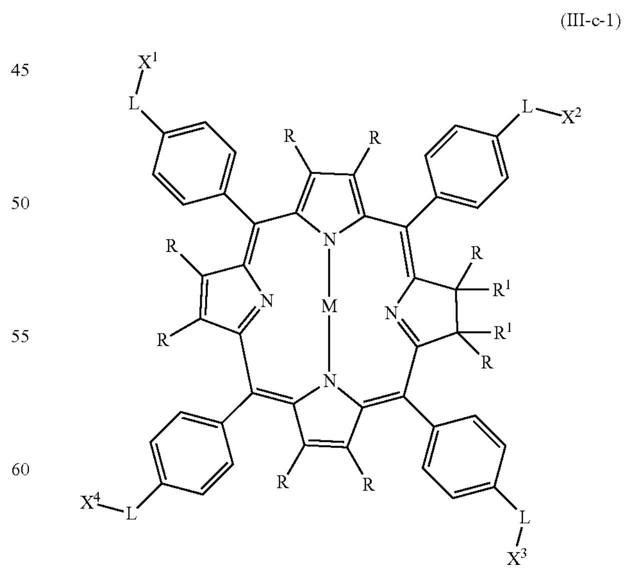

or a salt, or tautomer thereof; wherein M, R, L, and $X^1$-$X^4$ are as defined herein.

In certain embodiments, the compound of Formula (III) is of Formula (III-c-2):

(III-c-2)

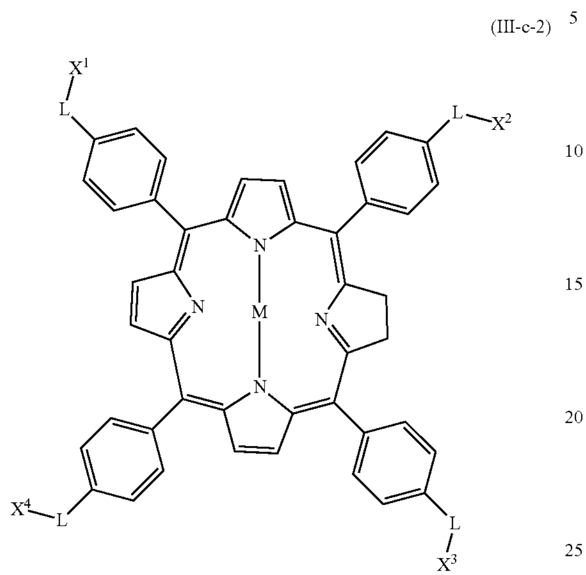

or a salt, or tautomer thereof; wherein M, L and $X^1$-$X^4$ are as defined herein.

In certain embodiments, the compound of Formula (III) is of Formula (III-c-3):

(III-c-3)

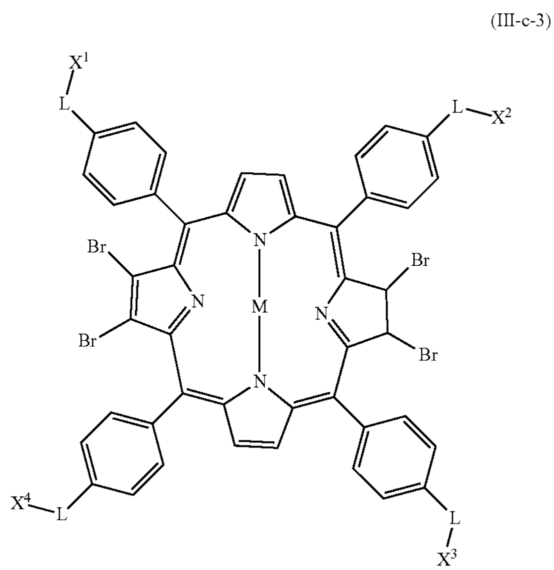

or a salt, or tautomer thereof; wherein M, L and $X^1$-$X^4$ are as defined herein.

In certain embodiments, the compound of Formula (III) is of Formula (III-c-4):

(III-c-4)

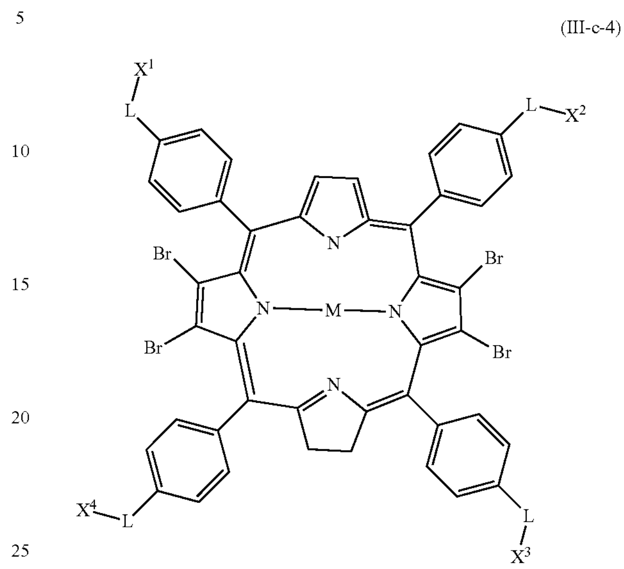

or a salt, or tautomer thereof; wherein M, L and $X^1$-$X^4$ are as defined herein.

In certain embodiments, the compound of Formula (III) is of Formula (III-c-5):

(III-c-5)

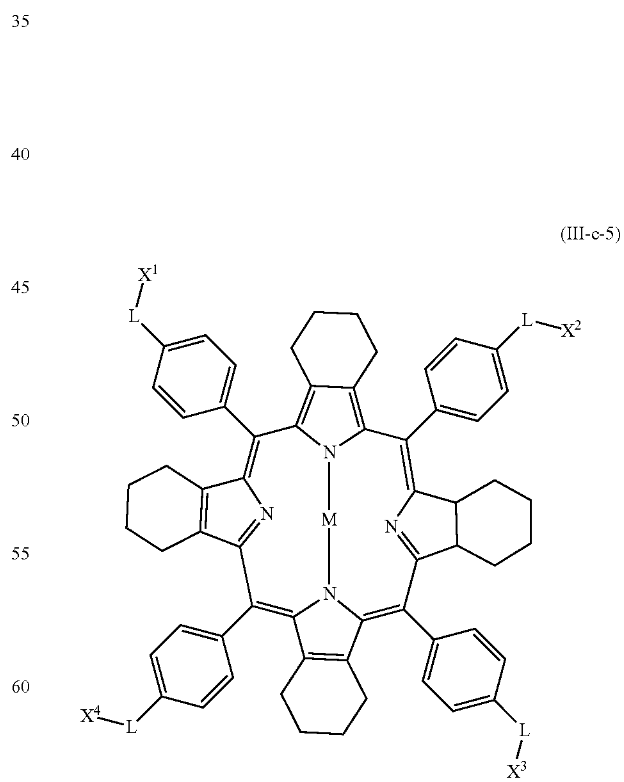

or a salt, or tautomer thereof; wherein M, L and $X^1$-$X^4$ are as defined herein.

In certain embodiments, the compound of Formula (III) is of Formula (III-c-6):

(III-c-6)

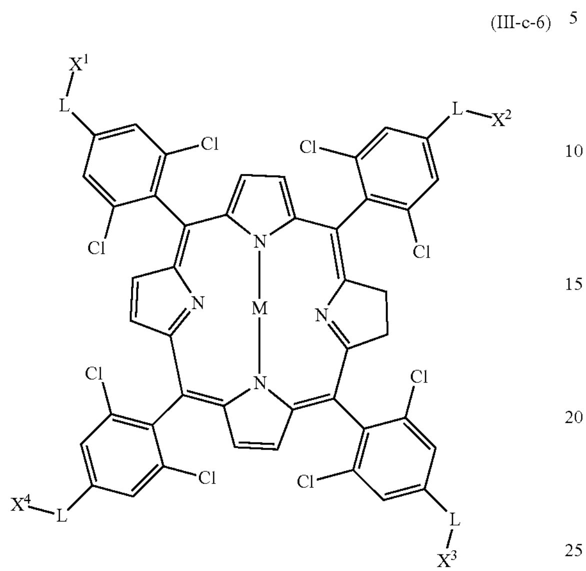

or a salt, or tautomer thereof; wherein M, L and $X^1$-$X^4$ are as defined herein.

In certain embodiments, the compound of Formula (III) is of Formula (III-c-7):

(III-c-7)

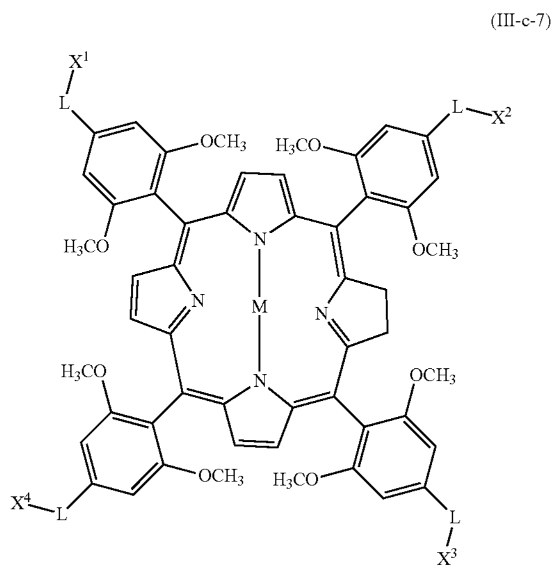

or a salt, or tautomer thereof; wherein M, L and $X^1$-$X^4$ are as defined herein.

In certain embodiments, the compound of Formula (III) is of formula:

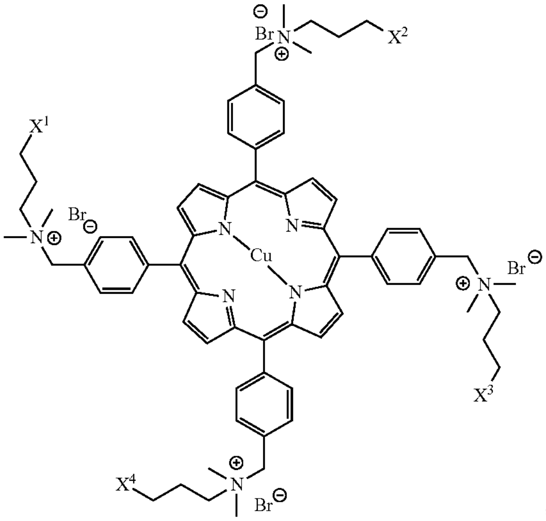

;

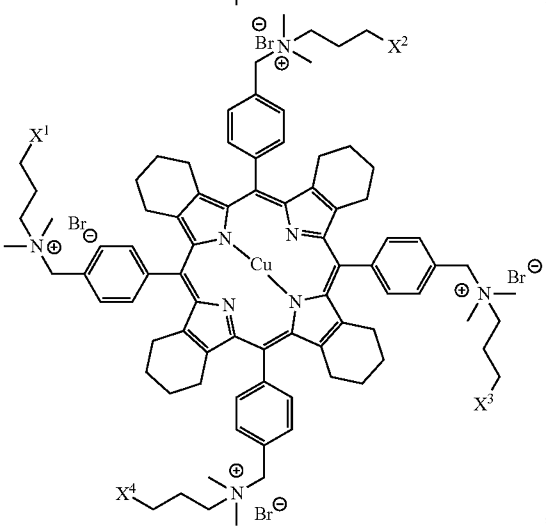

;

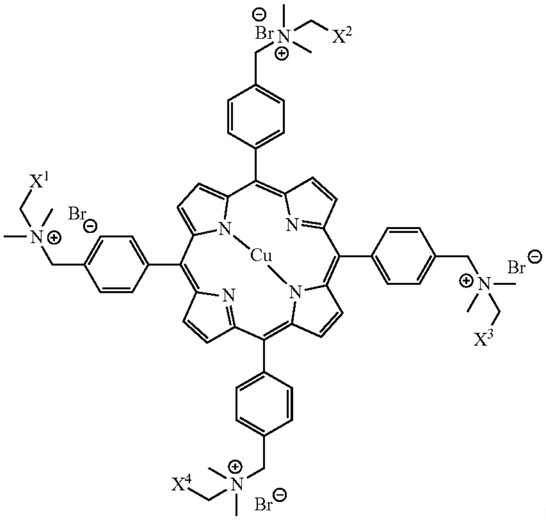

;

-continued

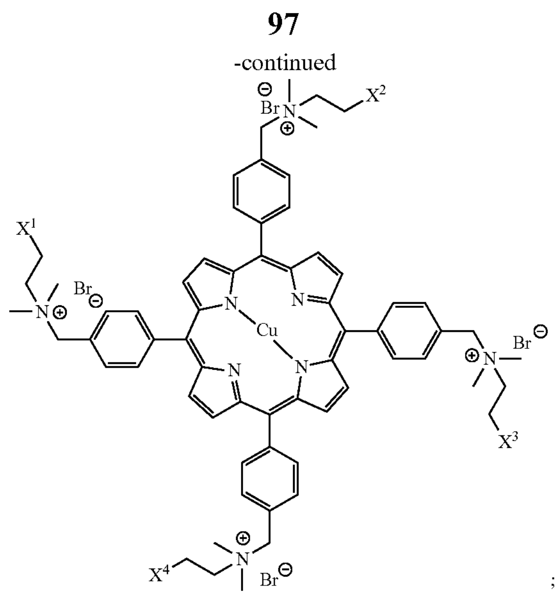

;

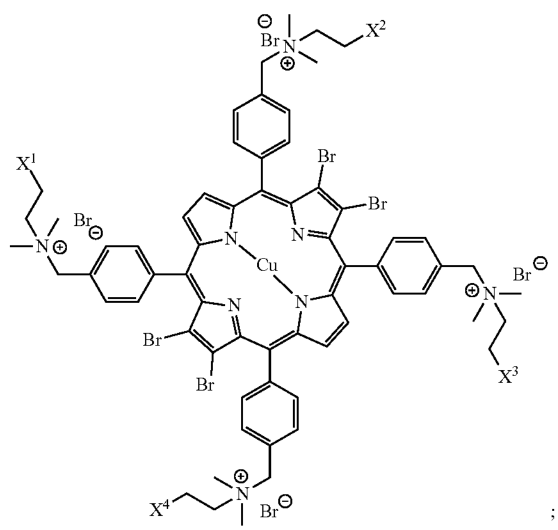

;

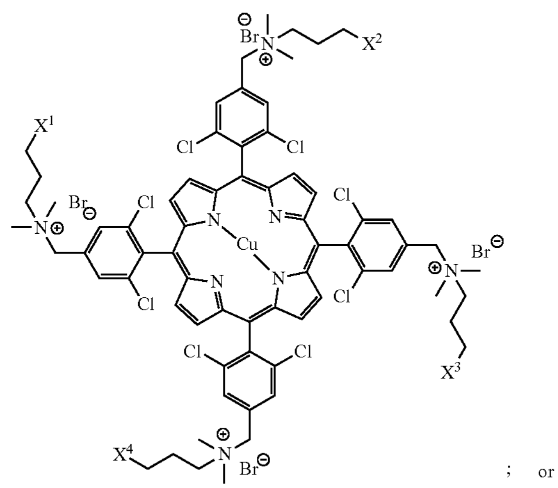

; or

-continued

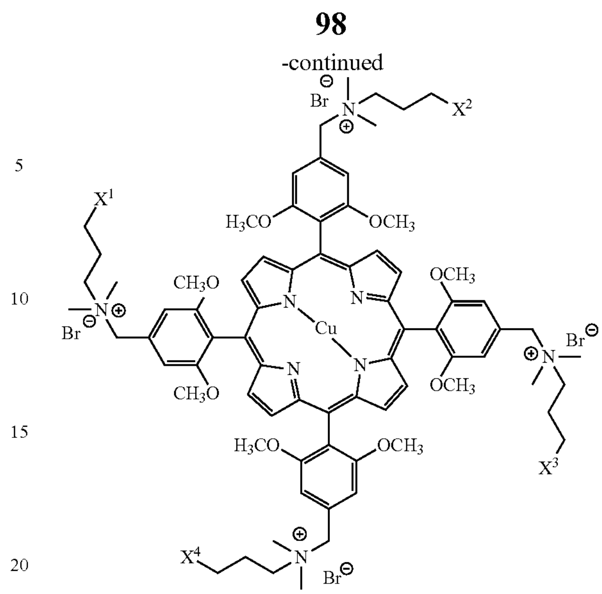

or a salt, or tautomer thereof.

In certain embodiments, the optical device is a contact lens or an intraocular lens. In certain embodiments, the optical device is a contact lens, an intraocular lens, or an implantable contact lens. In certain embodiments, the optical device is a contact lens. In certain embodiments, the optical device is an intraocular lens. In certain embodiments, the optical device is an implantable contact lens. An implantable contact lens may also be referred to as an implantable collamer lens.

In certain embodiments, the compound of Formula (III) in the device imparts beneficial properties as compared to a device without the compound of Formula (III).

In certain embodiments, the optical device selectively filters blue light. In certain embodiments, blue light has a wavelength between 380-550 nm, 380-530 nm, or 380-520 nm, 380-470 nm. In certain embodiments, transmittance of light through the device is less than 40% at one or more wavelength between 380-800 nm and at least 90% at one or more wavelength between 450-700 nm. In certain embodiments, transmittance of light through the device is less than 30% at one or more wavelength between 380-800 nm and at least 90% at one or more wavelength between 450-700 nm. In certain embodiments, transmittance of light through the device is less than 20% at one or more wavelength between 380-800 nm and at least 90% at one or more wavelength between 450-700 nm. In certain embodiments, transmittance of light through the device is less than 10% at one or more wavelength between 380-800 nm and at least 90% at one or more wavelength between 450-700 nm.

In certain embodiments, transmittance of light through the device is less than 40% at one or more wavelengths between 380-550 nm and at least 90% at one or more wavelength between 450-700 nm. In certain embodiments, transmittance of light through the device is less than 30% at one or more wavelengths between 380-550 nm and at least 90% at one or more wavelength between 450-700 nm. In certain embodiments, transmittance of light through the device is less than 20% at one or more wavelengths between 380-550 nm and at least 90% at one or more wavelength between 450-700 nm. In certain embodiments, transmittance of light through the device is less than 10% at one or more wavelengths between 380-550 nm and at least 90% at one or more wavelength between 450-700 nm.

In certain embodiments, transmittance of light through the device is less than 40% at one or more wavelengths between 380-470 nm and at least 90% at one or more wavelength between 450-700 nm. In certain embodiments, transmittance of light through the device is less than 30% at one or more wavelengths between 380-470 nm and at least 90% at one or more wavelength between 450-700 nm. In certain embodiments, transmittance of light through the device is less than 20% at one or more wavelengths between 380-470 nm and at least 90% at one or more wavelength between 450-700 nm.

In certain embodiments, transmittance of light through the device is less than 10% at one or more wavelengths between 380-470 nm and at least 90% at one or more wavelength between 450-700 nm.

In certain embodiments, the presence of the compound of Formula (III) in the device reduces photopic transmission of light by less than 50%, less than 40%, less than 30%, less than 20%, less than 10%, less than 5%, less than 3%, or less than 1% as compared to a device without the compound of Formula (III).

In certain embodiments, the presence of the compound of Formula (III) in the device reduces scotopic transmission of light by less than 50%, less than 40%, less than 30%, less than 20%, less than 10%, less than 5%, less than 3%, or less than 1% as compared to a device without the compound of Formula (III).

In certain embodiments, the presence of the compound of Formula (III) in the device suppresses melatonin by less than 50%, less than 40%, less than 30%, less than 20%, less than 10%, less than 5%, less than 3%, or less than 1% as compared to a device without the compound of Formula (III).

In certain embodiments, the presence of the compound of Formula (III) in the device increases discomfort glare by less than 50%, less than 40%, less than 30%, less than 20%, less than 10%, less than 5%, less than 3%, or less than 1% as compared to a device without the compound of Formula (III).

In certain embodiments, the presence of the compound of Formula (III) in the device decreases discomfort glare by at least 50%, at least 40%, at least 30%, at least 20%, at least 10%, at least 5%, at least 3%, or at least 1% as compared to a device without the compound of Formula (III).

In certain embodiments, the presence of the compound of Formula (III) in the device results in color distortion of less than 12 JND, less than 11 JND, less than 10 JND, less than 9 JND, less than 8 JND, less than 7 JND, less than 6 JND, less than 5 JND, less than 4 JND, less than 3 JND, less than 2 JND, or less than 1 JND as compared to a device without the compound of Formula (III), wherein color distortion is measured by the shift in the L*a*b* uniform color space coordinates.

Also disclosed herein is a method of protecting retinal pigment epithelium from blue light in a subject in need thereof, the method comprising applying the disclosed optical device to the eye of the subject.

In certain embodiments, the presence of the compound of Formula (III) in the device increases retinal pigment epithelial toxicity by less than 50%, less than 40%, less than 30%, less than 20%, less than 10%, less than 5%, less than 3%, or less than 1% as compared to a device without the compound of Formula (III).

In certain embodiments, the presence of the compound of Formula (III) in the device decreases retinal pigment epithelial toxicity by at least 50%, at least 40%, at least 30%, at least 20%, at least 10%, at least 5%, at least 3%, or at least 1% as compared to a device without the compound of Formula (III).

Also disclosed herein is a method of preparing the optical device. In certain embodiments, the method comprises combining the compound of Formula (II) with a polymeric matrix. In certain embodiments, the polymeric matrix is any polymeric matrix suitable for the manufacture of a contact lens or an intraocular lens. In certain embodiments, the polymeric matrix is any polymeric matrix suitable for the manufacture of a contact lens, an intraocular lens, and/or an implantable contact lens. In certain embodiments, the polymeric matrix is any polymeric matrix suitable for the manufacture of a contact lens. In certain embodiments, the polymeric matrix is any polymeric matrix suitable for the manufacture of an intraocular lens. In certain embodiments, the polymeric matrix is any polymeric matrix suitable for the manufacture of an implantable contact lens. In certain embodiments, the polymeric matrix is an acrylic, acrylamide, vinyl, allyl, or vinyl ester polymer. In certain embodiments, the method further comprises heating at a temperature above room temperature to induce cross-linking of the compound of Formula (II) and/or polymerization. In certain embodiments, the method comprises photoinitiation to induce cross-linking of the compound of Formula (II) and/or polymerization.

In certain embodiments, the method comprises photocuring to induce cross-linking of the compound of Formula (II) and/or polymerization.

In certain embodiments, the device may be described by the method used to prepare the device. In such embodiments, the optical device is prepared by combining the compound of Formula (II) with a polymeric matrix.

EXAMPLES

In order that the invention described herein may be more fully understood, the following examples are set forth. The examples described in this application are offered to illustrate the compounds, devices, and methods provided herein and are not to be construed in any way as limiting their scope.

The following synthesis examples disclose methods and compositions that have been successfully linked into lens resins with optimized weighted properties.

$^1$H-NMR spectra were recorded on Bruker 600 MHz spectrometer. $CD_3OD$ (Methanol-$d_3$) and DMSO-$d_6$ (Dimethyl sulfoxide-$d_6$) were used as solvents. UPLC of porphyrins was acquired on ACQUITY UPLC H-Class PLUS UPLC with Waters PDA detector, using Phenomenex Jupiter® 5 μm C18 300 Å, LC Column (150×2.0 mm). LC-MS of porphyrins was acquired on The Thermo Scientific™ Q Exactive™ HF hybrid quadrupole-Orbitrap mass spectrometer, using Phenomenex Aeris™ 3.6 μm WIDEPORE C4 200 Å, LC Column (50×2.1 mm). UV-vis spectra were obtained on Perkin Elmer Lambda 850 UV-Vis Spectrophotometer.

tetra-(Dimethylaminopropylmethacrylamidophenyl) porphine tetrabromide (1) and Cu(II) tetra-(dimethylaminopropylmethacrylamidophenyl) porphine tetrabromide (8)
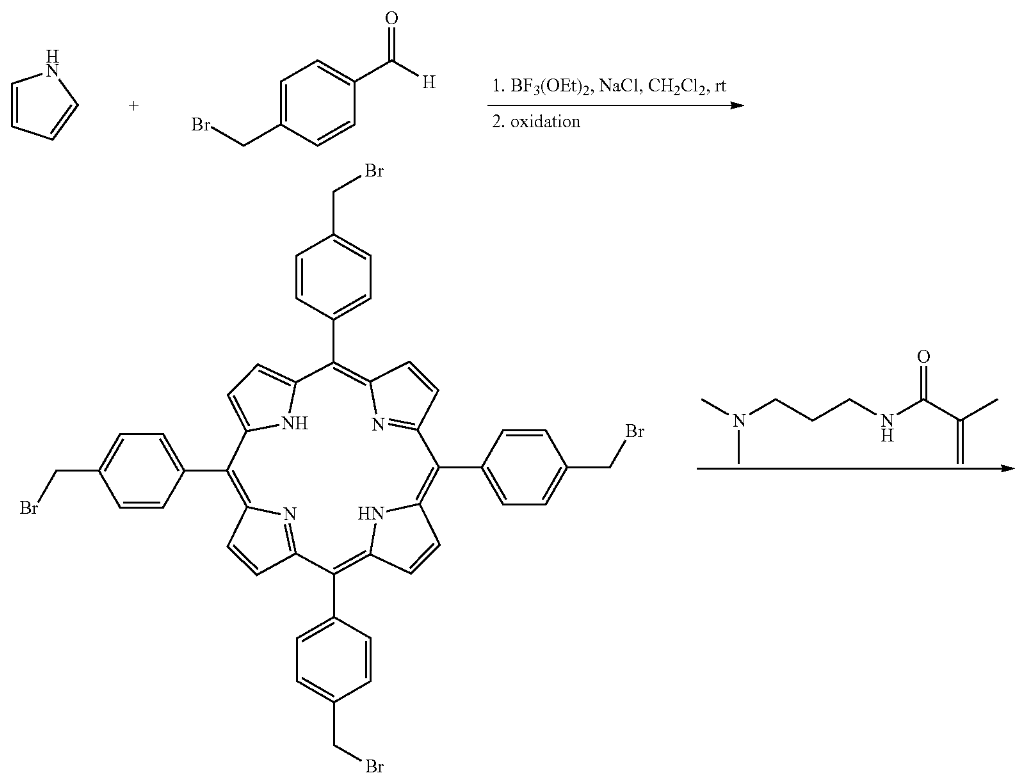
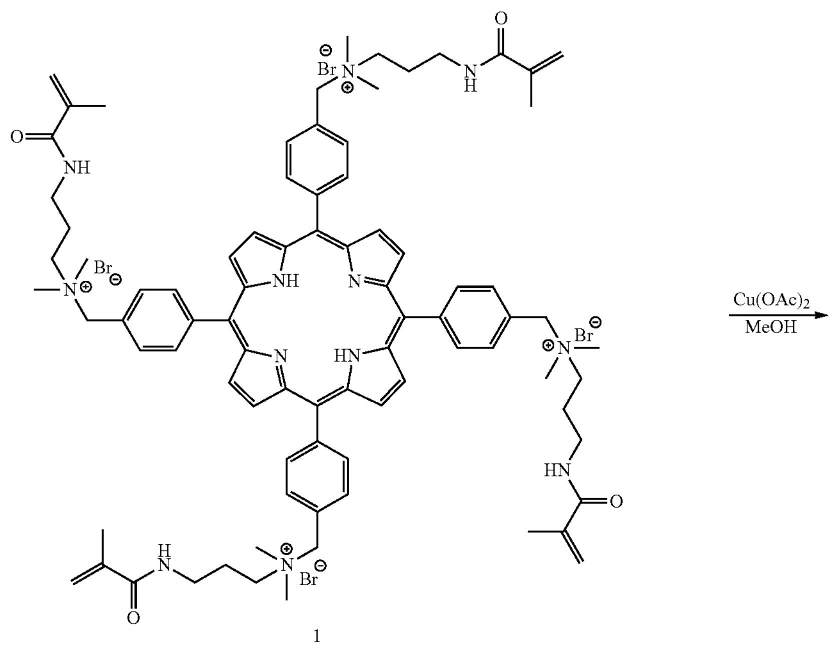
1

-continued

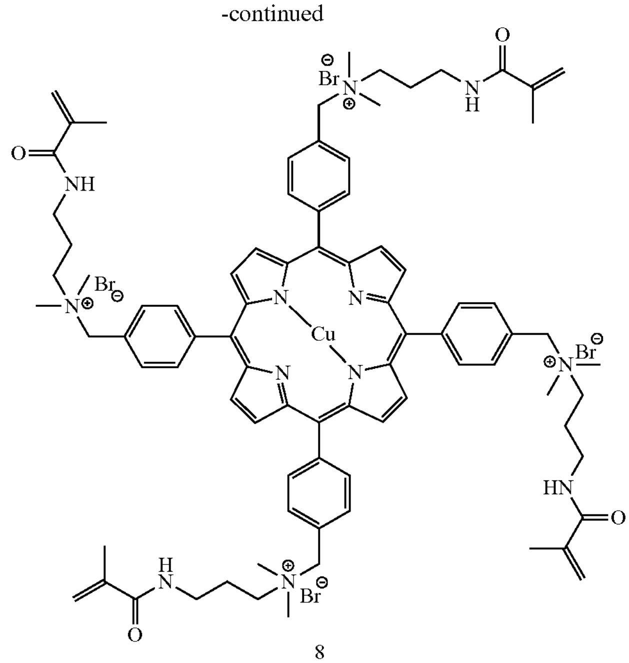

8

Step 1: The target porphyrin was generated using reaction conditions reported by Lindsay et. al. (J. Porphyrins Phthalocyanines 2002; 6: 159-185). 95 g (1.42 mol) Pyrrole and 120 g (1.489 mol) 4-bromomethylbenzaldehyde were charged to methylene chloride. A nitrogen purge of the reaction flask was performed for 15 minutes and then 11 mL (0.09 mol) $BF_3$-$Et_2O$ was charged. The reaction was stirred for 1 hour at ambient temperature before 261 g (1.06 mol) p-chloranil was charged. Following an 18 hour hold, the reaction solution was passed through a silica gel plug eluting with methylene chloride and the filtrate collected. Concentration of the solution produced a finely divided purple solid suspension. The suspension was filtered, and the resulting wet cake washed with minimal MeOH. 250.36 g (72% yield) of meso-tetra (4-bromomethylphenyl) porphine was isolated after lyophilization. $^1$H NMR ($CDCl_3$) δ 8.812 (s, 8H), 8.166 (d, 8H), 7.770 (d, 8H), 4.826 (s, 8H), −2.858 (s, 2H); UV-VIS ($CH_2Cl_2$) 419.0, 515.5, 551.0, 590.5, 646.0 nm.

Figure 12:
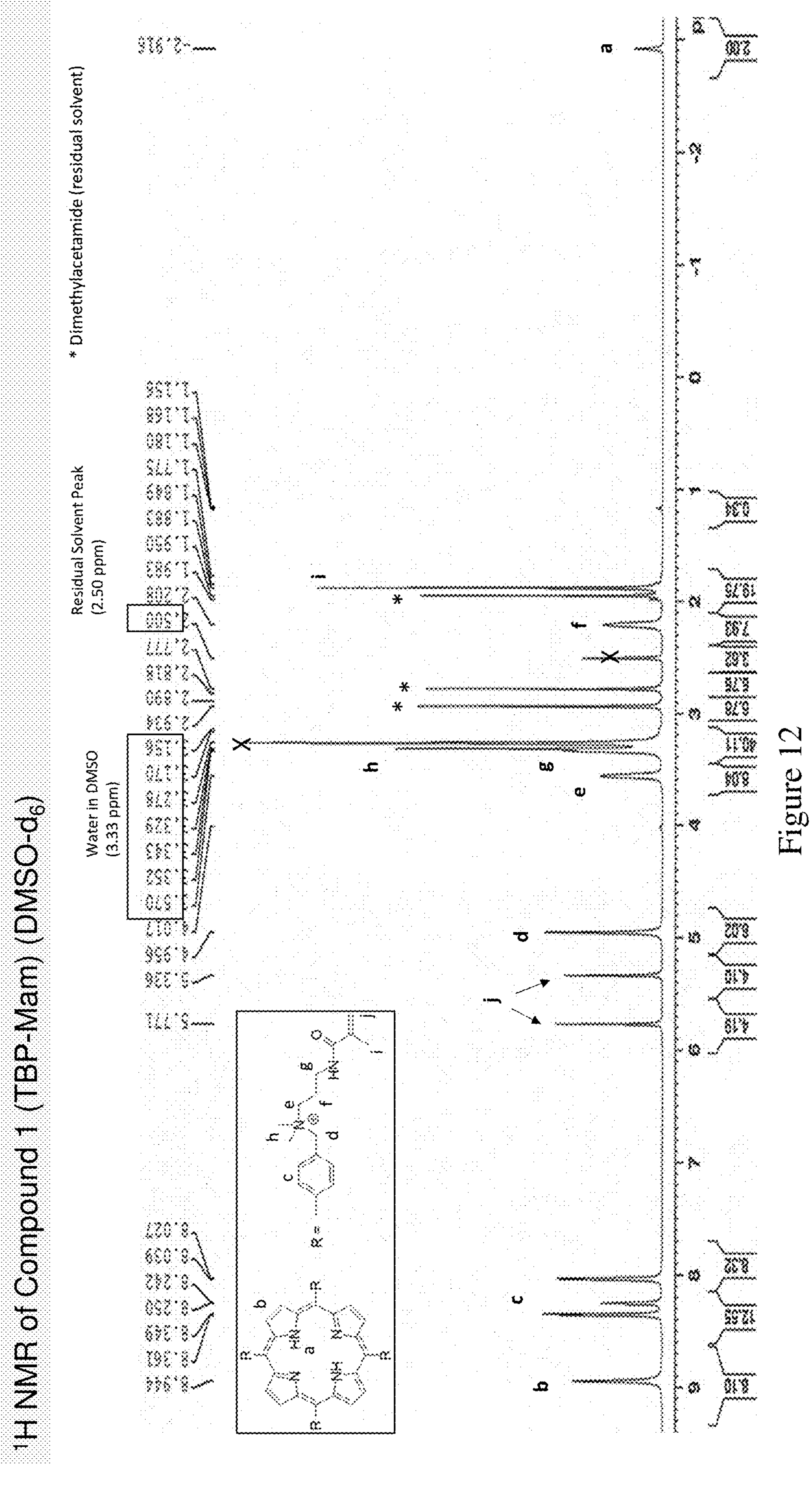
FIG. 12. $^1H$ NMR spectrum of exemplary compound 1.

Step 2: 1 g (1 mmol) meso-Tetra (4-bromomethylphenyl) porphine and 1.47 mL (8 mmol)N-[3-(dimethylamino)propyl]methacrylamide were charged to 20 mL N,N-dimethylacetamide (DMAc). The reaction solution was agitated for 2 hours at ambient temperature and then poured into 250 mL ethyl acetate (EtOAc) and the resulting solid was collected by filtration and washed with minimal EtOAc to provide compound 1. This crude solid was then carried forward to Step 3 without drying. See $^1$H NMR in FIG. 12.

Step 3: The crude solid obtained from Step 2 was dissolved in 75 mL MeOH and 0.26 g (1 mmol) $Cu(OAc)_2$ charged to the reaction solution. The reaction was stirred at 50° C. for 1 hour and then poured into 200 mL EtOAc. The resulting suspension was filtered and the isolated solid washed with minimal EtOAc. The solid was dried using a lyophilizer to give 1.653 g (94% yield over two steps) Cu(II) tetra-(dimethylaminopropylmethacrylamidophenyl)porphine. UV-VIS ($CH_3OH$) 412.0, 537.5 nm.

Figure 14:
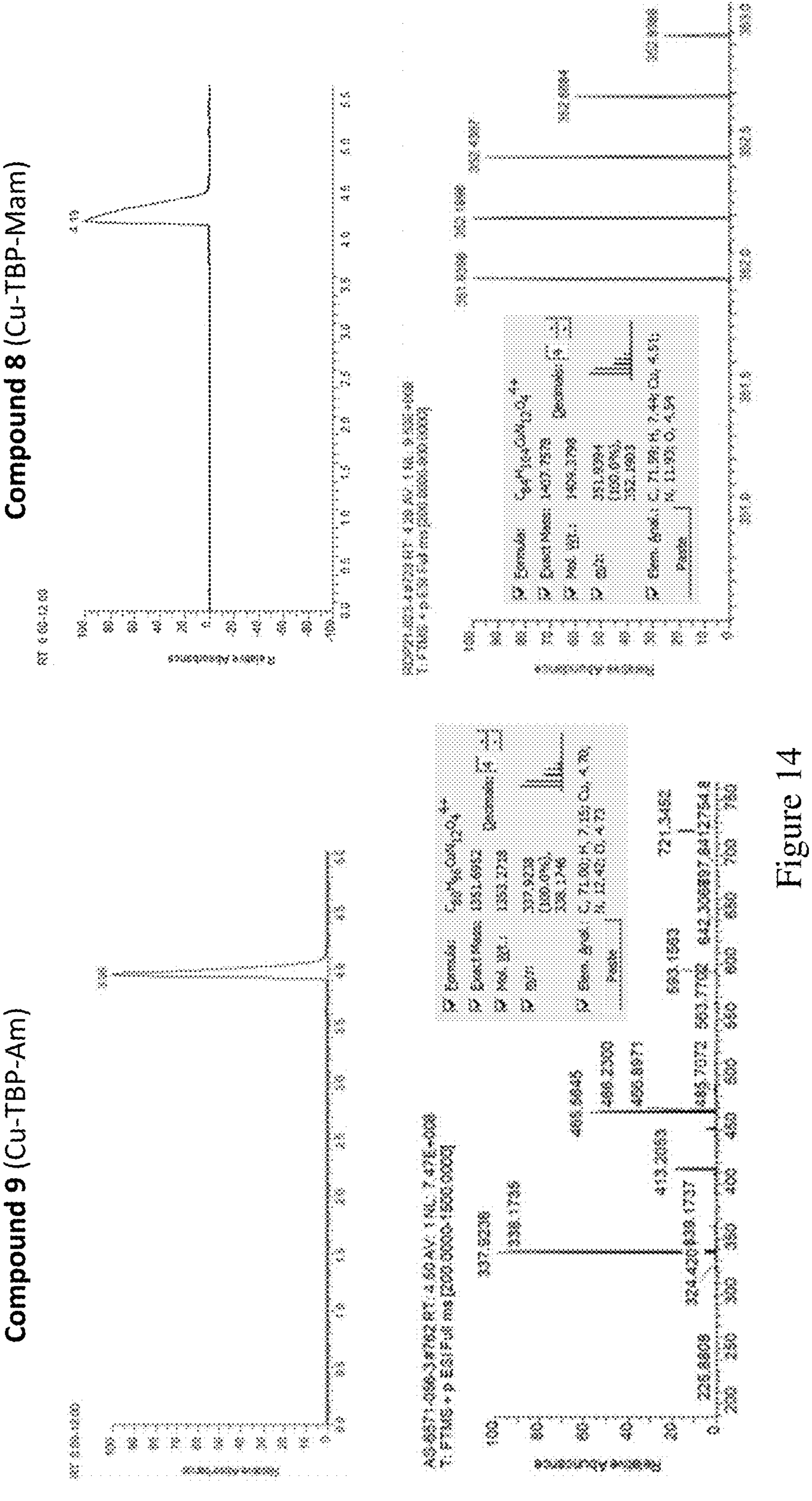
FIG. 14. LC-MS chromatogram and spectra of exemplary compounds 8 and 9.

Liquid Chromatography-Mass Spectrometry (LC-MS): mass spectrometry shows quadruple charged ions (4+) with m/z in agreement with theoretical values (FIG. 14).

Figure 15:
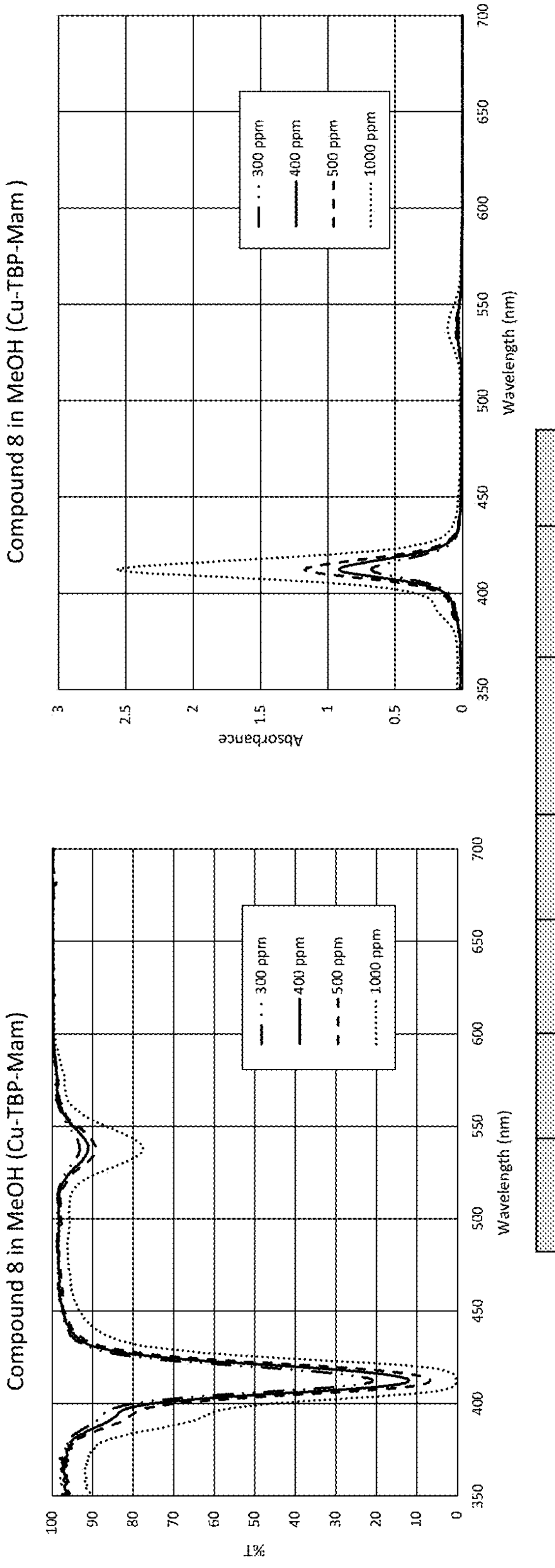
FIG. 15. UV-visible transmittance at various concentrations for exemplary compound 8.

Compound 8 also characterized by UV-visible transmittance at concentrations ranging from 300 to 1000 ppm (FIG. 15). Molar extinction coefficients of 490,000-544,000 M-1 cm-1 for Soret band are in agreement with literature values for similar metallated porphyrins (Taniguchi, M.; Lindsey, J. S. Photochemistry and Photobiology, 2018, 94, 290-327).

Tetra-(dimethylaminopropylacrylamidophenyl) porphine tetrabromide (2) and Cu(II) tetra-(dimethylaminopropylacrylamidophenyl) porphine tetrabromide (9)

(2)

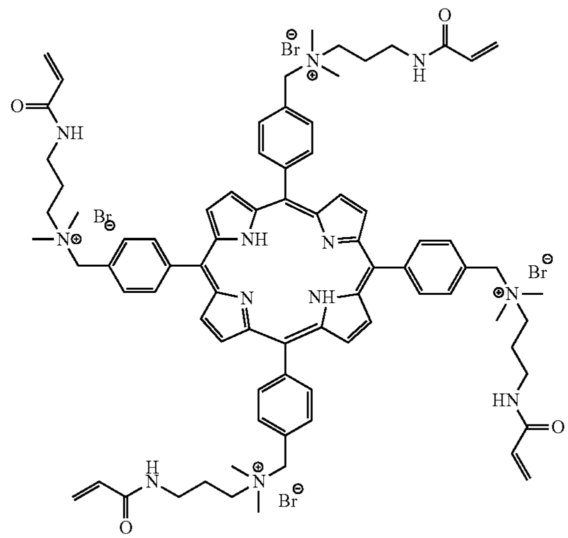

-continued (9)

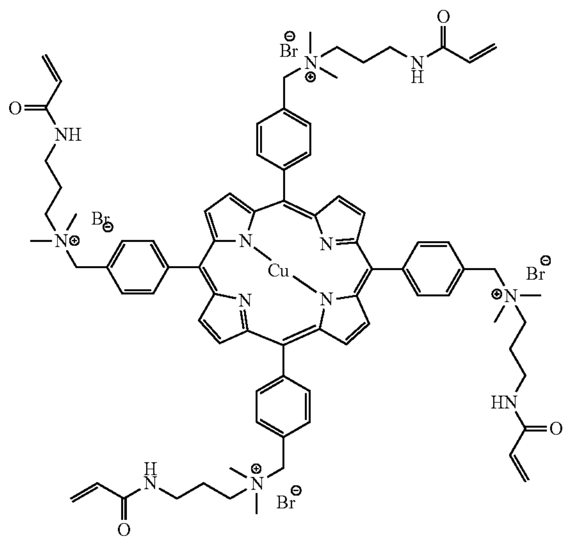

-continued (10)

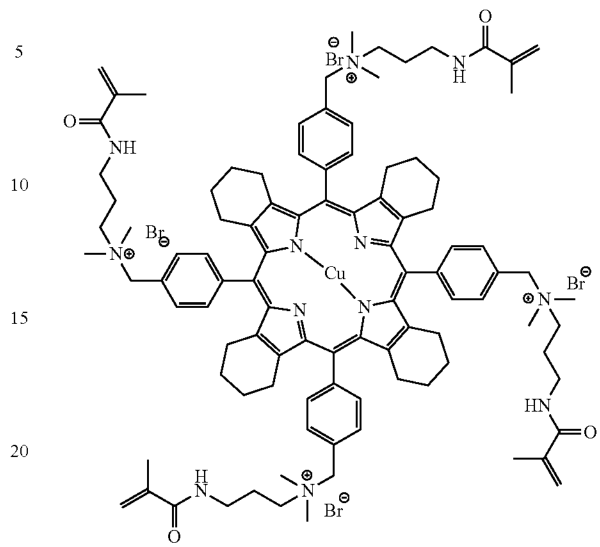

Compounds 2 and 9 were prepared in a manner analogous to that used to prepare compounds 1 and 8. of the disclosure were prepared in an analogous manner as described below.

Figure 13:
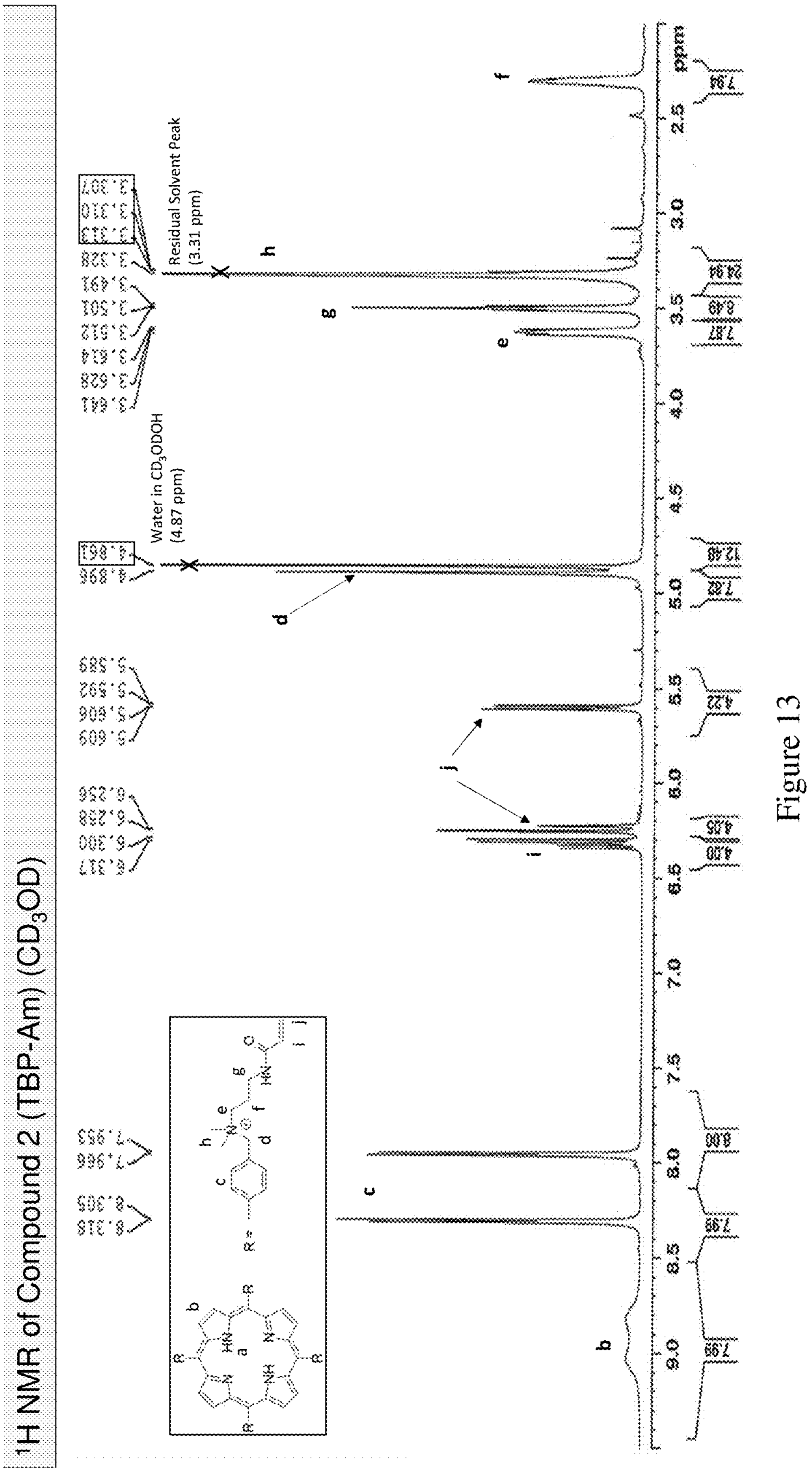
FIG. 13. $^1H$ NMR spectrum of exemplary compound 2.

Compound 2: see $^1H$ NMR spectrum in FIG. 13

Compound 9 characterization: Liquid Chromatography-Mass Spectrometry (LC-MS): mass spectrometry shows quadruple charged ions (4+) with m/z in agreement with theoretical values (FIG. 14).

Figure 16:
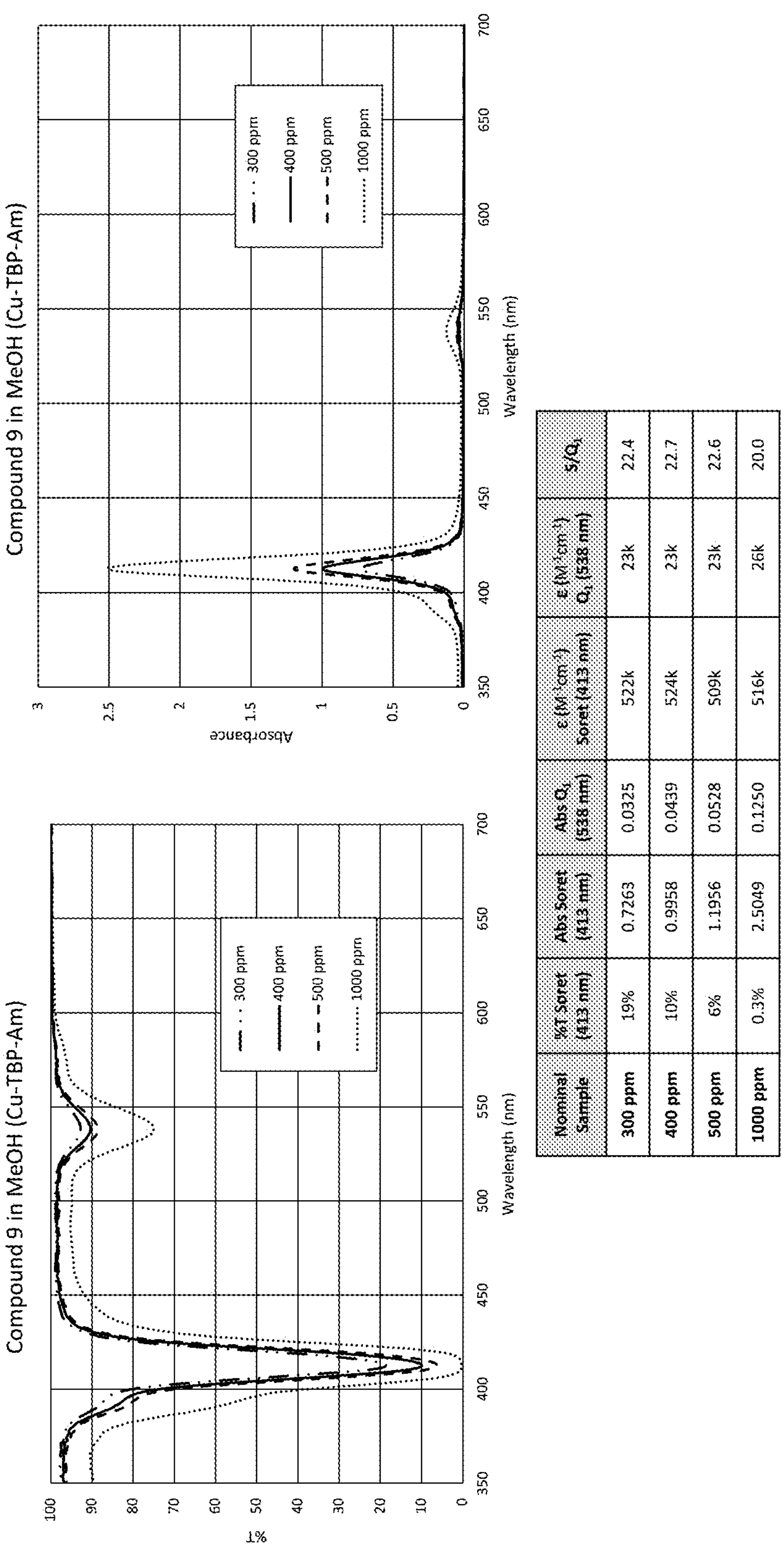
FIG. 16. UV-visible transmittance at various concentrations for exemplary compound 9.

Compound 9 also characterized by UV-visible transmittance at concentrations ranging from 300 to 1000 ppm (FIG. 16). Molar extinction coefficients of 490,000-544,000 $M^{-1}$ $cm^{-1}$ for Soret band are in agreement with literature values for similar metallated porphyrins (Taniguchi, M.; Lindsey, J. S. Photochemistry and Photobiology, 2018, 94, 290-327).

Cyclohexyl tetra-(dimethylaminopropylmethacrylamidophenyl)porphine tetrabromide (3) and Cu(II) Cyclohexyl tetra-(dimethylaminopropylmethacrylamidophenyl)porphine tetrabromide (10)

(3)

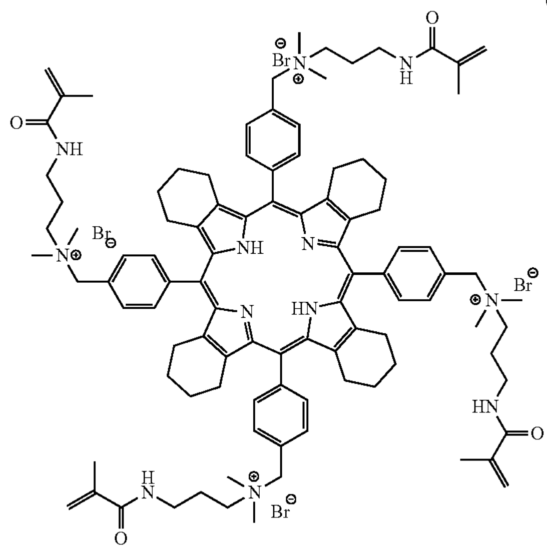

4.5 g (25 mmol) of the methyl isoindole carboxylate and 100 mL ethylene glycol were charged to a reactor purged with nitrogen and equipped with a condenser and heating mantle. 2.54 g (45 mmol) KOH was charged and the reaction heated to reflux with agitation. The reaction was cooled to ambient after 1.5 hours. A second reactor was charged with 1.35 L DCM and purged with nitrogen. 5 g (25 mmol) 4-bromomethylbenzaldehyde and 36.7 g NaCl were also charged to the second reactor and agitation initiated. The reaction solution from the first reactor was extracted with 3×50 mL DCM. The combined organic layers back were extracted with 2×50 mL water and dried with $Na_2SO_4$. Following filtration to remove $Na_2SO_4$, the solution was charged to the second reactor with 0.2 mL $BF_3$-$Et_2O$. After two hours of agitation at ambient temperature, 4.63 g (19 mmol) p-chloranil was charged and the nitrogen stream removed. After stirring for 18 hours, the reaction solution was concentrated by rotavap and the residue purified by silica gel column chromatography using a 1-3% MeOH/DCM gradient. 6.15 g of the desired cyclohexyl TBP was isolated.

0.53 g (0.4 mmol) cyclohexyl TBP and 175 mg $Cu(OAc)_2$ were charged to 30 mL MeOH. The reaction solution was agitated for 5 minutes at ambient temperature and then the suspension was filtered to collect the precipitated solid. The isolated solids were dissolved in 50 mL DCM and filtered. The filtrate was then treated with 0.6 mL DMAPMA agitating at ambient for 30 minutes. 20 mL MeOH was charged and the solution heated to 50° C. holding for one hour. The reaction was then poured into 400 mL ethyl acetate (EtOAc) and the resulting solid collected by filtration and washed with 50 mL EtOAc. 650 mg Cu(II) Cyclohexyl TBP DMAPMA (compound 10) was isolated. UV-Vis (MeOH): $\lambda_{max}$ 423.0 nm, $\lambda_{max}$ 554.5 nm, $\lambda_{max}$ 582.5 nm.

Tetra-(4-dimethylaminomethylstyrenylphenyl)porphine tetrabromide (4) and Cu(II) tetra-(4-dimethylaminomethylstyrenylphenyl)porphine tetrabromide (11)

(4)

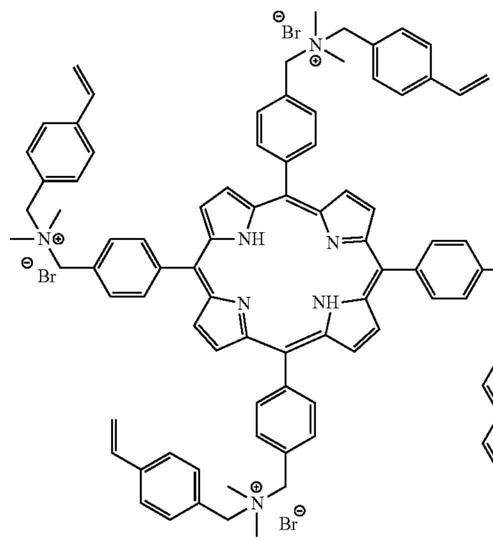

(11)

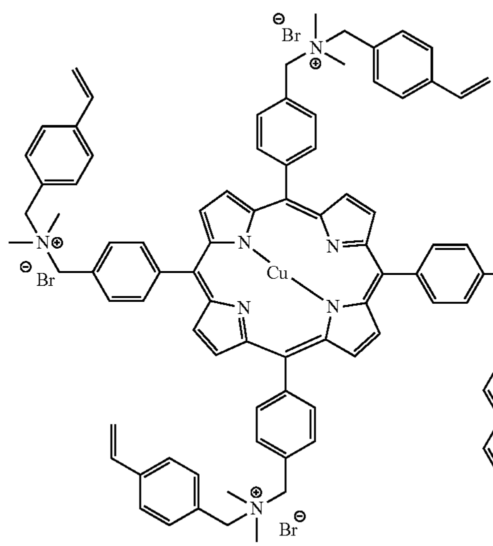

1 g (1 mmol) meso-Tetra (4-bromomethylphenyl) porphine and 1.3 g (8 mmol)N-(4-Vinylbenzyl)-N,N-dimethylamine were charged to 20 mL DMAc. The reaction solution was agitated for 2 hours at ambient temperature and then poured into 250 mL ethyl acetate (EtOAc) and the resulting solid collected by filtration and washed with 50 mL EtOAc to provide compound 4.

The crude solid was dissolved in 250 mL MeOH and 0.5 g (2.5 mmol) $Cu(OAc)_2$ charged to the reaction solution. The reaction was stirred at 50° C. for 1 hour and then poured into 1000 mL EtOAc. The resulting suspension was filtered and the isolated solid washed with 50 mL EtOAc. The solid was dried using a lyophilizer to give Cu (II) TBP Styrene (compound 11). UV-Vis (MeOH): $\lambda_{max}$ 412.0 nm, $\lambda_{max}$ 537.5 nm.

Tetra-(dimethylaminoethylmethacrylatephenyl)porphine tetrabromide (5) and Cu(II) tetra-(dimethylaminoethylmethacrylatephenyl)porphine tetrabromide (12)

(5)

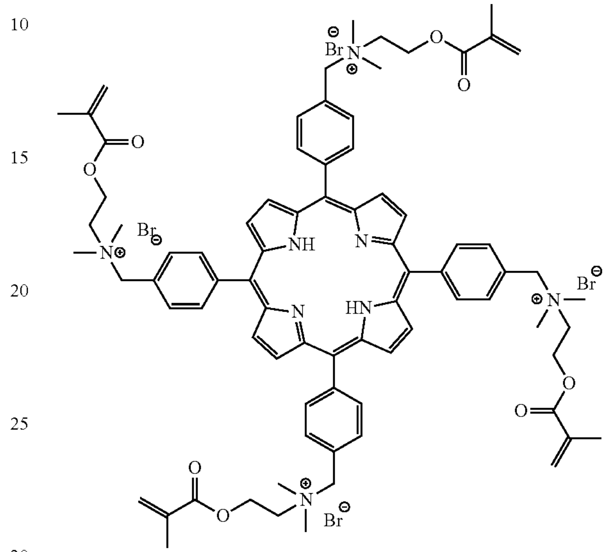

(12)

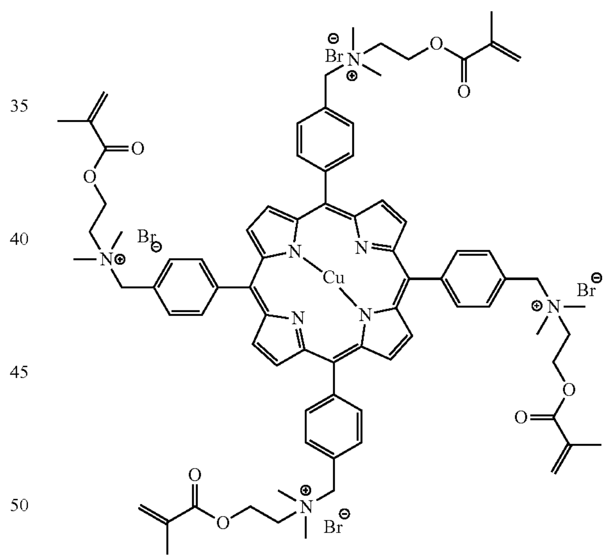

1.5 g (2 mmol) meso-Tetra (4-bromomethylphenyl) porphine and 2.05 mL (12 mmol) 2-(N,N-dimethylamino)ethyl methacrylate were charged to 50 mL $CHCl_3$ and allowed to agitate for 18 hours. The intermediate precipitated and adhered to the reaction vessel. The solvent was decanted and the resulting solid dissolved in 150 mL chilled (0° C.) MeOH to provide compound 5.

0.34 g $Cu(OAc)_2$ was charged while maintaining a reaction temperature of 0° C. After 30 minutes, the reaction mixture was poured into 800 mL EtOAc. The resulting suspension was filtered, washed with minimal EtOAc, and dried by lyophilizer. 0.86 g Cu(II) TBP DMEMA (compound 12) was isolated. UV-Vis ($H_2O$): $\lambda_{max}$ 412.0 nm, $\lambda_{max}$ 539.0 nm.

tetra-(dimethylaminoethylacrylamidophenyl)porphine tetrabromide (6) and Cu(II) tetra-(dimethylaminoethylacrylamidophenyl)porphine tetrabromide (13)

(6)

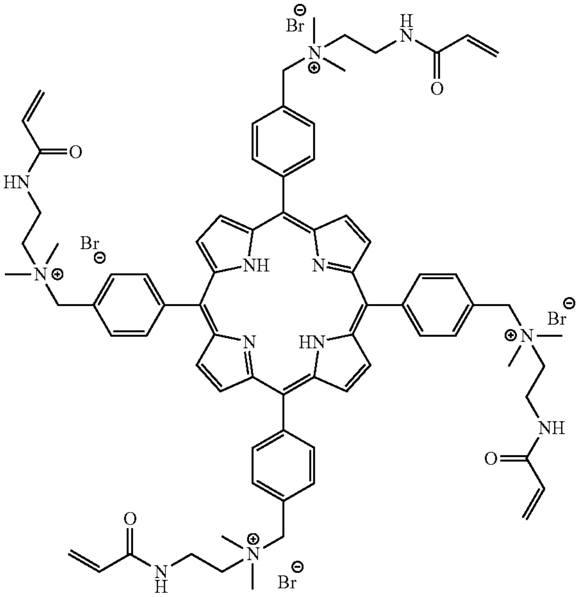

(13)

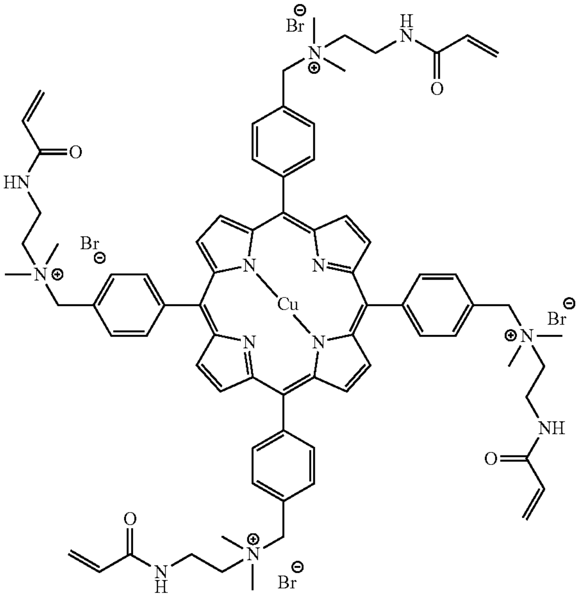

7.65 g (7.8 mmol) meso-Tetra (4-bromomethylphenyl) porphine and 10.3 mL (68.2 mmol)N-[2-(dimethylamino) ethyl]acrylamide were charged to 80 mL DMAc. The reaction solution was agitated for 2 hours at ambient temperature and then poured into 800 mL ethyl acetate (EtOAc) and the resulting solid collected by filtration and washed with 50 mL EtOAc to provide compound 6.

The crude solid was dissolved in 250 mL MeOH and 2 g (248 mmol) $Cu(OAc)_2$ charged to the reaction solution. The reaction was stirred at 50° C. for 1 hour and then poured into 800 mL EtOAc. The resulting suspension was filtered and the isolated solid washed with minimal EtOAc. The solid was dried using a lyophilizer to give Cu(II) tetra-(dimethylaminoethylmethacrylamidophenyl) porphine (compound 13). UV-Vis (MeOH): $\lambda_{max}$ 412.0 nm, $\lambda_{max}$ 537.5 nm.

Cu(II) tetra-bromo-tetra-(dimethylaminoethylacrylatephenyl)porphine (14)

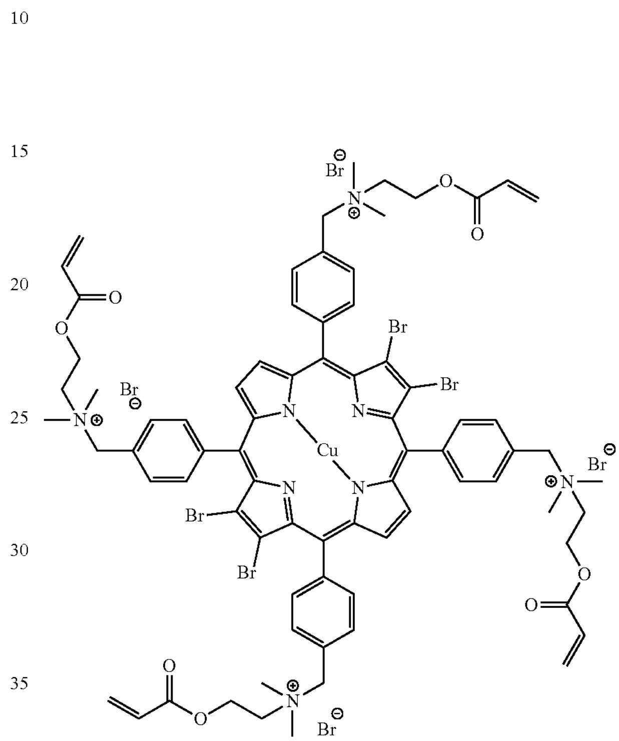

5 g (5 mmol) meso-tetra (4-bromomethylphenyl) porphine and 7.22 g N-bromosuccinimide were charged to 400 mL chloroform and heated to reflux. After two hours, the reaction was cooled to ambient and concentrated by rotavap. The resulting residue was dissolved in minimal chloroform and purified using a silica gel plug eluting with chloroform. Fractions containing the desired tetrabromo TBP intermediate were concentrated and the residue dissolved in 500 mL methanol.

7.2 g copper (II) acetate was charged and the reaction stirred for one hour. Concentration by rotavap followed by purification using a silica plug eluted with chloroform yielded 1.5 g Cu (II) tetrabromo TBP.

0.9 g (1 mmol) Cu (II) tetrabromo TBP was dissolved in 5 mL DMF. 5.5 mL DMEMA was charged dropwise and the reaction stirred for 2 hours. The reaction solution was poured into 300 mL EtOAc. The precipitated solids were collected by filtration, washed with minimal EtOAc, and dried by lyophilizer. 0.87 g Cu(II) tetrabromo DMEMA was isolated (compound 14). UV-Vis (ACN/MeOH): $\lambda_{max}$ 428.0 nm, $\lambda_{max}$ 556.0 nm, $\lambda_{max}$ 599.0 nm.

N,N',N"-(((20-(2,6-dichloro-4-(((3-methacrylamidopropyl)dimethyl-14-azaneyl)methyl)phenyl)porphyrin-5,10,15-triyl)tris(3,5-dichlorobenzene-4,1-diyl))tris(methylene))tris(3-methacrylamido-N,N-dimethylpropan-1-aminium) tetrabromide (15) and Cu(II) N,N',N"-(((20-(2,6-dichloro-4-(((3-methacrylamidopropyl)dimethyl-14-azaneyl)methyl)phenyl)porphyrin-5,10,15-triyl)tris(3,5-dichlorobenzene-4,1-diyl))tris(methylene))tris(3-methacrylamido-N,N-dimethylpropan-1-aminium) tetrabromide (16)

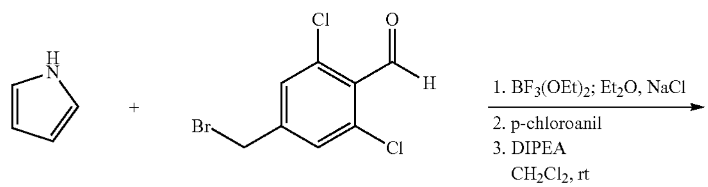

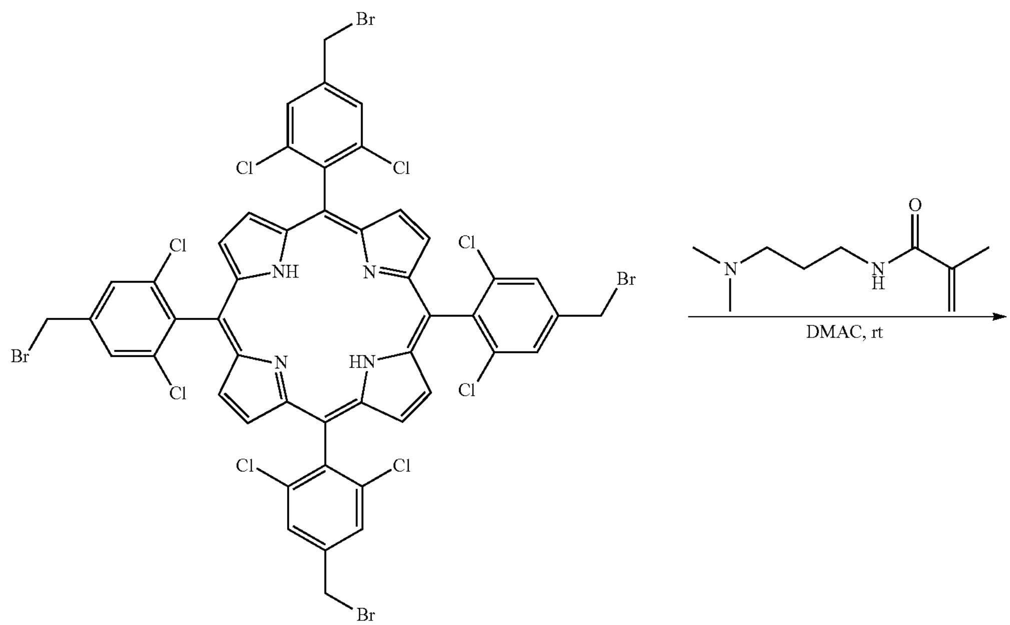

-continued
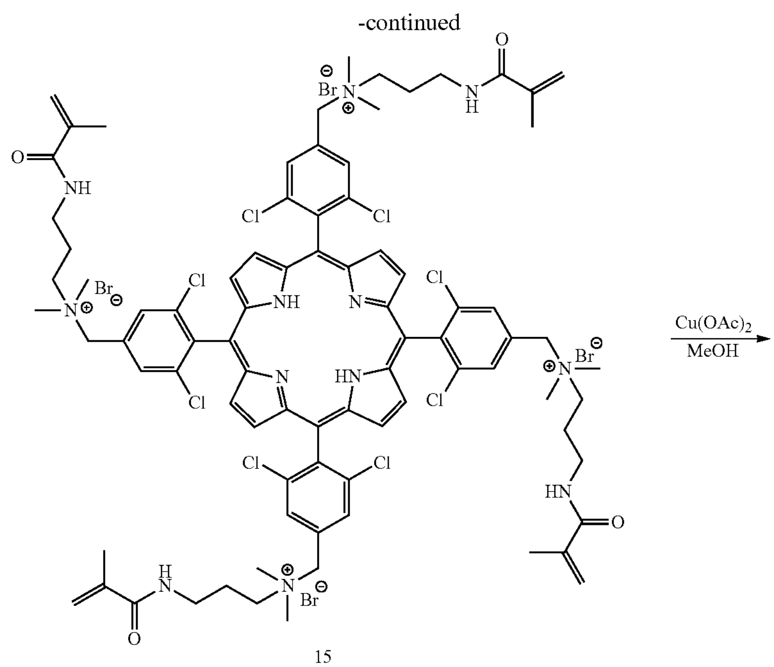
15
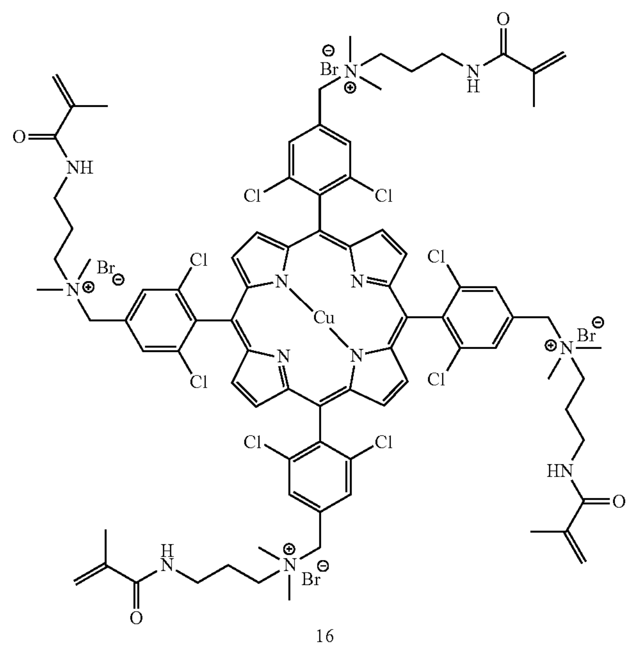
16

Compounds (15) and (16) may be prepared by the synthetic route above and in a manner analogous to that used to prepare compounds (1) and (8).

tetra-(dimethylaminoethylmethacrylamidophenyl) porphine tetrabromide (17) and Cu(II) tetra-(dimethylaminoethylmethacrylamidophenyl)porphine tetrabromide (18)

(17)

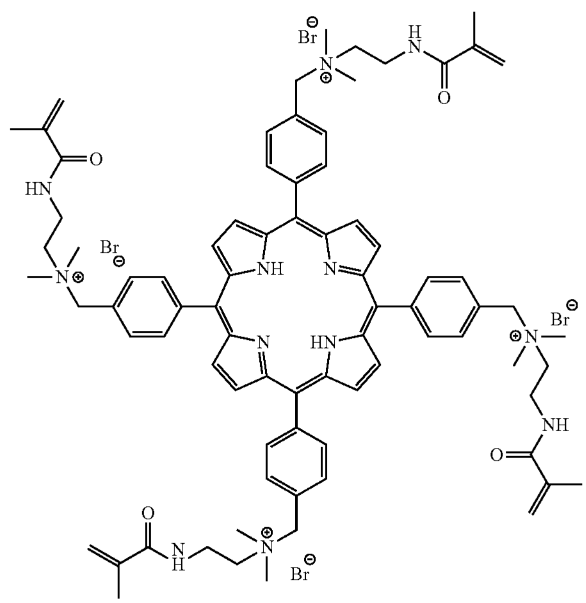

-continued (18)

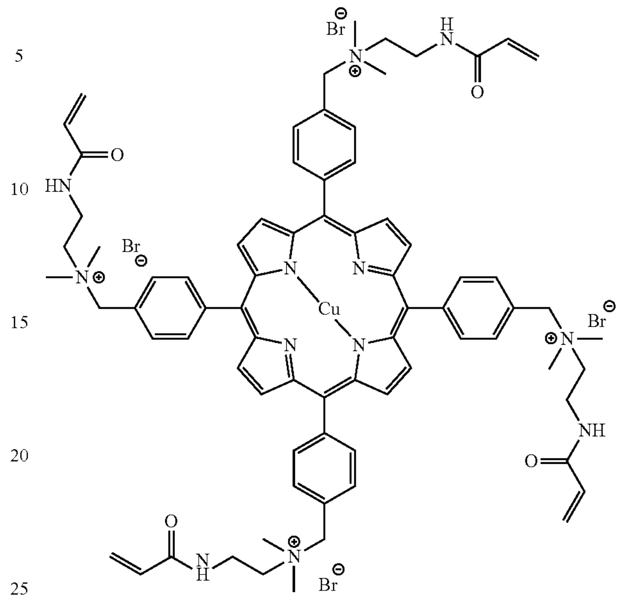

Compounds (17) and (18) may be prepared in a manner analogous to that used to prepare compounds (6) and (13).

Solubility Studies

The solubilities of exemplary compounds 8 and 9 were evaluated in various solvent systems in comparison with copper tetraphenylporphyrin (Cu-TPP) as a control. The results in Table 2 show significantly improved solubility in the tested solvent, monomers and simulated formulation systems.

Experimental Procedure:

1. Weigh 3 to 4 mg of the Copper porphyrin compound into an 8 mL scintillation vial
2. In the case of one solvent or monomer, dilute to 500 ppm with the solvent or monomer, add a stir bar, and stir mixture overnight.
3. In the case of multiple solvents, add the best solvent for the copper porphyrin first, add a stir bar and stir for 1 hour. Add the other solvents and stir overnight.

4. Evaluate solution miscibility after stirring overnight.

TABLE 2

| | $Solution_{500\ ppm}$ | Cu-TPP (control | Compound 9 (Cu-TBP Acrylamide) | Compound 8 (Cu-TBP Methacrylamide) |
|---|---|---|---|---|
| | Polymerizable groups | no | yes | yes |
| Solvents | 1-Propanol | Insoluble | Soluble | Soluble |
| Monomers | DMA | Soluble | Partially Soluble | Soluble |
| | HEMA | Insoluble | Soluble | Soluble |
| Simulated | 1-PrOH/DMA/TRIS (1:1:1) | Insoluble | Soluble | Soluble |
| Formulation (Monomer + TRIS + Silicone Oil) | 1-PrOH/DMA/TRIS/Silicone oil (1:1:1:1) | Insoluble | Partially Soluble | Soluble |

Stability Studies

Figure 17:
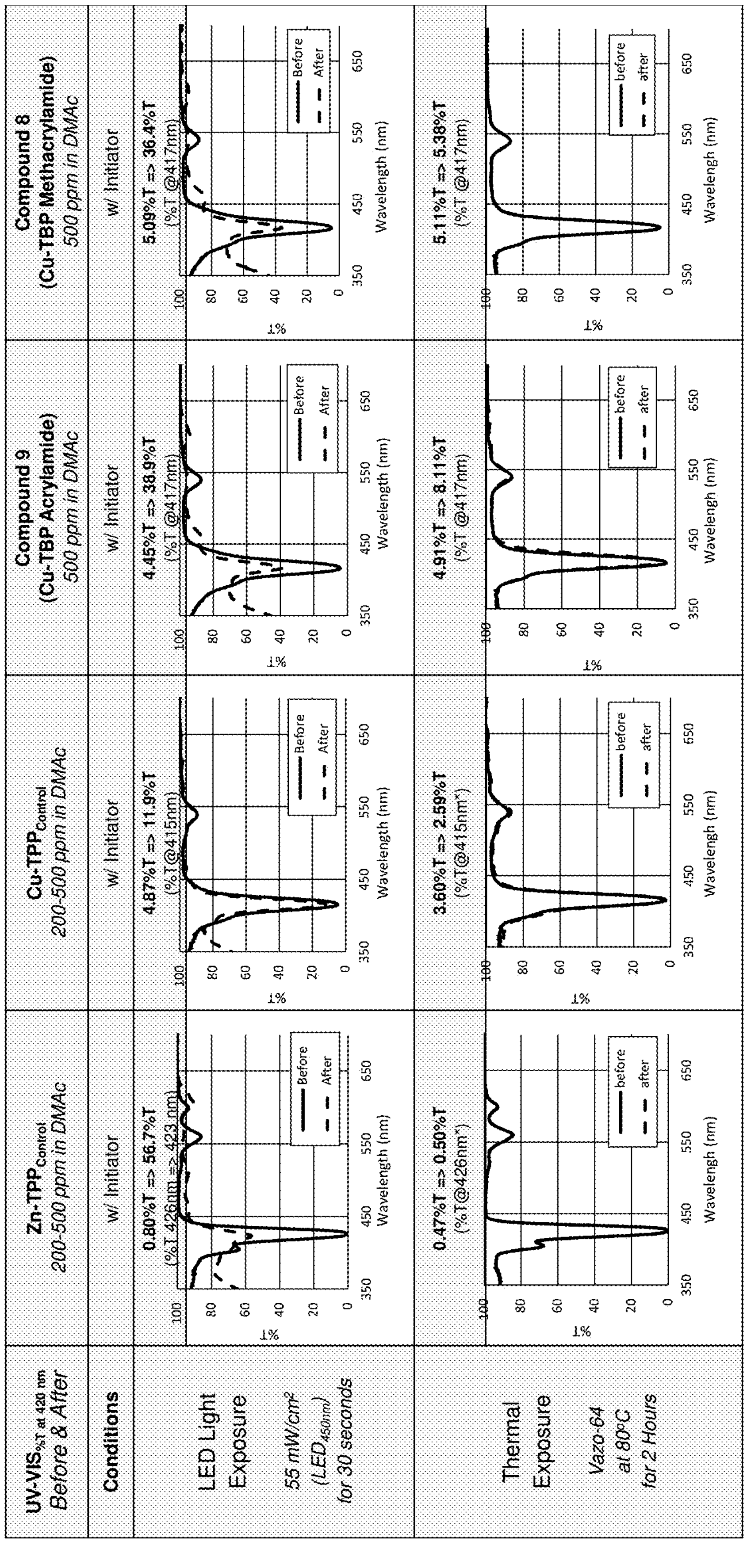
FIG. 17. Stabilities of exemplary compounds 8 and 9 evaluated under various conditions in the presence of initiator and monomer under curing conditions in comparison with copper tetraphenylporphyrin (Cu-TPP) and zinc tetraphenylporphyrin (Zn-TPP) as controls. Spectra were obtained before and after light or thermal exposure as detailed in the figure.
Figure 18:
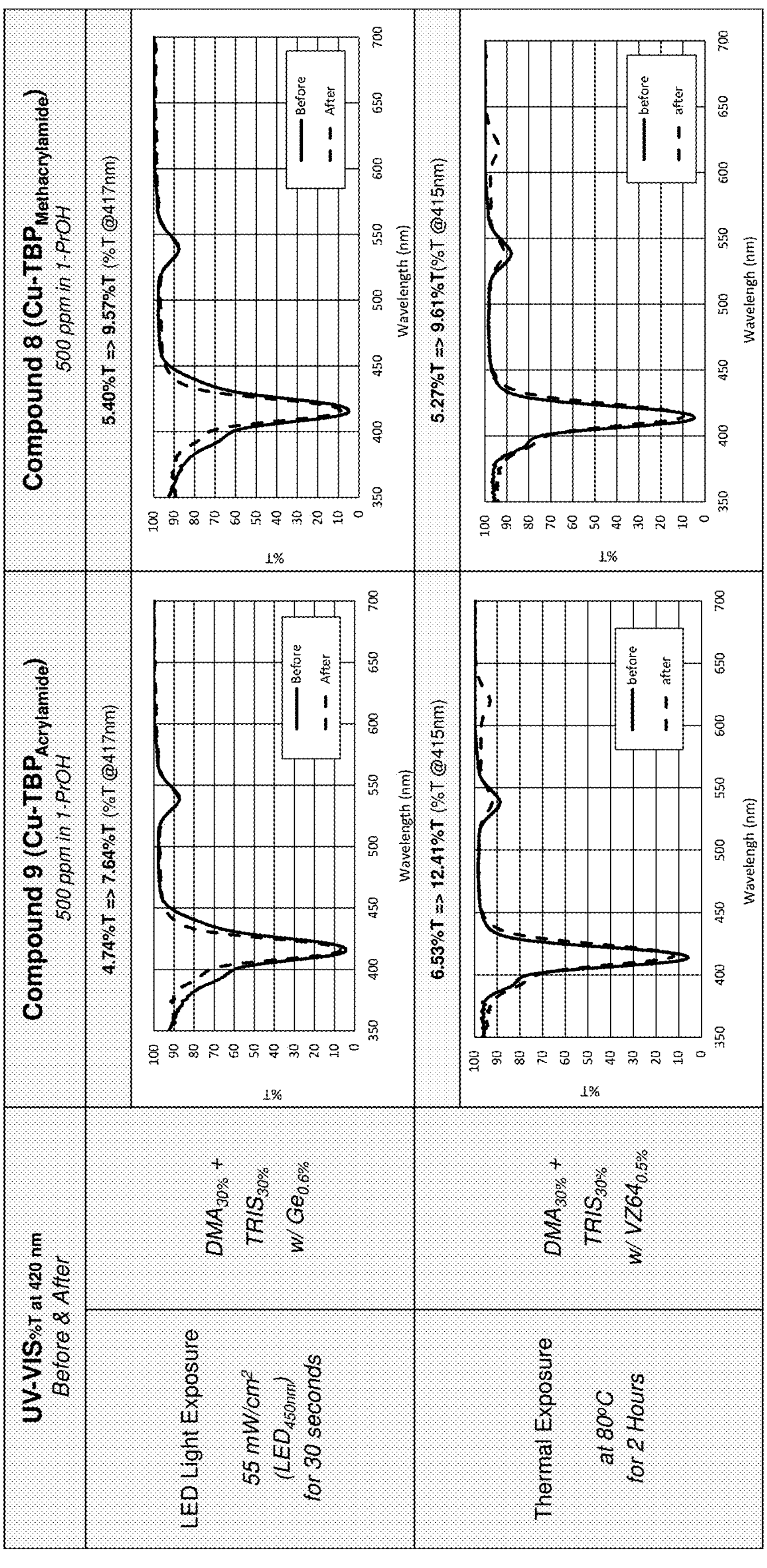
FIG. 18. Stabilities of exemplary compounds 8 and 9 evaluated under various conditions. Spectra were obtained before and after light or thermal exposure as detailed in the figure.

The stabilities of exemplary compounds 8 and 9 were evaluated under various conditions in the presence of initiator and monomer under curing conditions in comparison with copper tetraphenylporphyrin (Cu-TPP) and zinc tetraphenylporphyrin (Zn-TPP) as controls. The results in FIGS. 17 and 18 show that CuTPP is significantly more stable than ZnTPP under the tested LED light in the presence of photoinitiator. This difference is not observed under simulated thermal curing conditions (FIG. 17, column 1 and 2)

Under simulated photocuring conditions, compound 9 (Cu-TBP-Am) and compound 8 (Cu-TBP-Mam) show % T increase (FIG. 17, column 3 and 4, 1st raw), however this is not observed in the presence of monomers (FIG. 18, 1st raw)

Both compounds 8 and 9 show much better stability under simulated thermal curing conditions, either with and without monomers (FIG. 17, column 3 and 4 bottom and FIG. 18, 2nd raw)

Experimental Procedure for Photo-Curing System:

(A) for Stability Test without Monomers

1. Parent solution: Dimethylacetamide (DMAC) solutions (200-500 ppm) of corresponding porphyrins, namely ZnTPP (200 ppm), CuTPP (200 ppm), Cu-TBP-Am (500 ppm), and Cu-TBP-MAm (500 ppm) were prepared in amber glass vial. The solutions were allowed to stir at room temperature for about 0.5 hour to provide homogeneous solutions. Photoinitiator (0.6 wt %) was added to each solution (under yellow light), and the solution was stirred for another 1 hour.
2. Solution "BEFORE" Thermal Treatment & UV-VIS Measurement: The solution was transferred into 100 μm quartz cell and UV-Vis spectra were recorded using Perkin Elmer Lambda 850 UV-Vis Spectrophotometer. The spectrum was regarded as "before".
3. Photocuring of Parent Solution: Each quartz cell was exposed to 450 nm LED light with intensity of 55 $mW/cm^2$ for 30 s.
4. Solution "AFTER" photocuring & UV-VIS Measurement: UV-Vis spectra of solutions in 100 μm quartz cell exposed to LED light were recorded using Perkin Elmer Lambda 850 UV-Vis Spectrophotometer. The spectrum was regarded as "after".
5. % T Calculation: % Loss is expressed as % T increase at the specific wavelength of Soret band for each porphyrin solution.

(B) For Stability Test with Monomers

1. Parent solution: Cu-TBP-Am and Cu-TBP-MAm were dissolved in DMA (30 wt %), TRIS (30 wt %) and 1-PrOH (40 wt %) in amber glass vial to afford 500 ppm porphyrin solutions. The solutions were allowed to stir at room temperature for about 0.5 hour to provide homogeneous solutions. Photoinitiator (0.6 wt %) was added to each solution (under yellow light), and the solution was stirred for another 1 hour.
2. Solution "BEFORE" Thermal Treatment & UV-VIS Measurement: The solution was transferred into 100 μm quartz cell and UV-Vis spectra were recorded using Perkin Elmer Lambda 850 UV-Vis Spectrophotometer. The spectrum was regarded as "before".
3. Photocuring of Parent Solution: Each quartz cell was exposed to 450 nm LED light with intensity of 55 $mW/cm^2$ for 30 s.
4. Solution "AFTER" photocuring & UV-VIS Measurement: UV-Vis spectra of solutions in 100 μm quartz cell exposed to LED light were recorded using Perkin Elmer Lambda 850 UV-Vis Spectrophotometer. The spectrum was regarded as "after".
5. % T Calculation: % Loss is expressed as % T increase at the specific wavelength of Soret band for each porphyrin solution.

Experimental Procedure for Thermal-Curing System:

(A) for Stability Test without Monomers

1. Parent solution: Dimethylacetamide (DMAC) solutions (500 ppm) of corresponding porphyrins, namely ZnTPP, CuTPP, Cu-TBP-Am, and Cu-TBP-MAm were prepared in amber glass vial. The solutions were allowed to stir at room temperature for about 0.5 hours to provide homogeneous solutions. Vazo 64 (0.5 wt %) was added to each solution, and the solution was stirred for another 10 minutes. Each solution was bubbled with nitrogen for 5 minutes to remove oxygen.
2. Solution "BEFORE" Thermal Treatment & UV-VIS Measurement: About 0.2 g of parent solution was withdrawn by nitrogen filled syringe and diluted with 99 parts of DMAC to afford a homogeneous solution. Specifically, for the controls (ZnTPP and CuTPP), about 0.2 g of the solution was further diluted with 199 parts of DMAC and then homogenized. The solution was transferred into 1 cm quartz cell and UV-Vis spectra were recorded using Perkin Elmer Lambda 850 UV-Vis Spectrophotometer. The spectrum was regarded as "before".
3. Thermal treatment of Parent Solution: The remaining parent solution was placed into a pre-set 80° C. oven, and heated for 2 hours. After that, the vial was taken out from the oven, and allowed to cool down to room temperature.

4. Solution "AFTER" thermal Treatment & UV-VIS Measurement: Same as the procedure mentioned above, about 0.2 g of the thermally treated parent solution was withdrawn by a syringe and diluted with 99 parts of DMAC to afford a homogeneous solution. Specifically, for the controls (ZnTPP and CuTPP), 1 part of solution was diluted with 199 parts of DMAC and then homogenized. The solution was transferred into 1 cm quartz cell and UV-Vis spectra were recorded using Perkin Elmer Lambda 850 UV-Vis Spectrophotometer. The spectrum was regarded as "after".
5. % T Calculation: % Loss is expressed as % T increase at the specific wavelength of Soret band for each porphyrin solution.

(B) For Stability Test with Monomers

1. Parent Solution: Cu-TBP-Am and Cu-TBP-MAm were dissolved in DMA (30 wt %), TRIS (30 wt %) and 1-PrOH (40 wt %) in amber glass vial to afford 500 ppm porphyrin solutions. The solutions were allowed to stir at room temperature for about 0.5 hours to provide homogeneous solutions. Vazo 64 (0.5 wt %) was added to each solution, and the solution was stirred for another 10 minutes. Each solution was bubbled with nitrogen for 5 minutes to remove oxygen.
2. Solution "BEFORE" Thermal Treatment & UV-VIS Measurement: About 0.2 g of parent solution was withdrawn by nitrogen filled syringe and diluted with 99 parts of 1-PrOH to afford a homogeneous solution. Then, the solution was transferred into 1 cm quartz cell and UV-Vis spectra were recorded using Perkin Elmer Lambda 850 UV-Vis Spectrophotometer. The spectrum was regarded as "before".
3. Thermal treatment of Parent Solution: The remaining parent solution was placed into a pre-set 80° C. oven, and heated for 2 hours. After that, the vial was taken out from the oven, and allowed to cool down to room temperature.
4. Solution "AFTER" thermal Treatment & UV-VIS Measurement: Same as the procedure mentioned above, about 0.2 g of the thermally treated parent solution was withdrawn by a syringe and diluted with 99 parts of 1-PrOH to afford a homogeneous solution. Then, the solution was transferred into 1 cm quartz cell and UV-Vis spectra were recorded using Perkin Elmer Lambda 850 UV-Vis Spectrophotometer. The spectrum was regarded as "after".
5. % T Calculation: % Loss is expressed as % T increase at the specific wavelength of Soret band for each porphyrin solution.

The foregoing non-limiting synthetic examples use copper atoms to enhance the absorptive properties of the dye material. Alternative compositions with different metal centers, as well as varied porphyrin and chlorin heterocycles may be prepared and subjected to the same selection method based on weighted optical properties including luminous transmission, color distortion, circadian rhythm interference, retinal pigment epithelium protection, and discomfort glare.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising," "including," and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

(I)

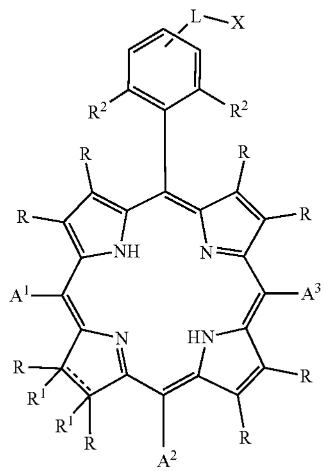

or a salt, or tautomer thereof, wherein:

each R is independently hydrogen, halogen, substituted or unsubstituted $C_1$-$C_{20}$ alkenyl, substituted or unsubstituted $C_1$-$C_{20}$ alkynyl, or two adjacent R groups, together with the atoms to which they are attached, form a substituted or unsubstituted $C_6$-$C_{14}$ aryl, substituted or unsubstituted $C_5$-$C_{14}$ heteroaryl, or substituted or unsubstituted $C_3$-$C_{14}$ heterocyclyl, or two adjacent R groups are each substituted or unsubstituted $C_1$-$C_{20}$ alkyl and, together with the atoms to which they are attached, form a substituted or unsubstituted $C_3$-$C_{14}$ carbocyclyl;

each $R^1$ is independently hydrogen, halogen, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, or two adjacent $R^1$ groups, together with the atoms to which they are attached, form a substituted or unsubstituted $C_6$-$C_{14}$ aryl, substituted or unsubstituted $C_3$-$C_{14}$ carbocyclyl, substituted or unsubstituted $C_5$-$C_{14}$ heteroaryl, or substituted or unsubstituted $C_3$-$C_{14}$ heterocyclyl; or one instance of $R^1$ and R on the same carbon form with that carbon a carbonyl;

$A^1$, $A^2$, and $A^3$ are independently hydrogen or a substituted aryl of formula:

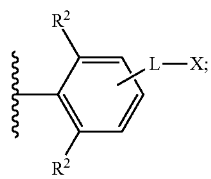

each $R^2$ is independently hydrogen, halogen, —$NO_2$, substituted or unsubstituted alkyl, —$NHR^A$, —$N(R^A)_2$, or —$OR^B$;

$\overline{\phantom{xxx}}$ is a single or double bond, provided that when is double bond, then each $R^1$ is absent;

each L is independently:

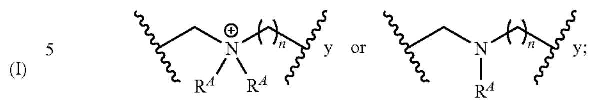

wherein:

n is 1-6;

each occurrence of $R^A$ is independently substituted or unsubstituted $C_1$-$C_{20}$ alkyl; and y labels the site with attachment to group X;

each X is independently hydrogen, halogen, substituted or unsubstituted $C_1$-$C_{20}$ alkyl, or a polymerizable group, provided that at least one X is a polymerizable group; and each occurrence of $R^B$ is independently hydrogen, substituted or unsubstituted acyl, substituted or unsubstituted $C_1$-$C_{20}$ alkyl, substituted or unsubstituted $C_1$-$C_{20}$ alkenyl, substituted or unsubstituted $C_1$-$C_{20}$ alkynyl, substituted or unsubstituted $C_3$-$C_{14}$ carbocyclyl, substituted or unsubstituted $C_3$-$C_{14}$ heterocyclyl, substituted or unsubstituted $C_6$-14 aryl, or substituted or unsubstituted $C_5$-14 heteroaryl.

2. The compound of claim 1, or a salt, or tautomer thereof, wherein each R is independently hydrogen, halogen, or two adjacent R groups, together with the atoms to which they are attached, form a substituted or unsubstituted $C_3$-$C_{14}$ carbocyclyl.

3. The compound of claim 1, or a salt, or tautomer thereof, wherein each $R^2$ is independently hydrogen, —$OR^B$, or halogen.

4. The compound of claim 1, or a salt, or tautomer thereof, wherein each X is independently an acrylate, a methacrylate, an acrylamide, a methacrylamide, a styrene, a vinyl sulfone, or alkenyl; wherein each X is substituted or unsubstituted.

5. The compound of claim 1, or a salt, or tautomer thereof, wherein each X is independently

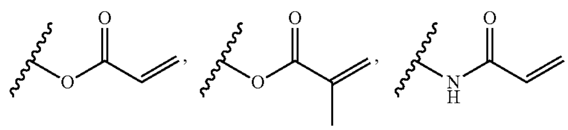

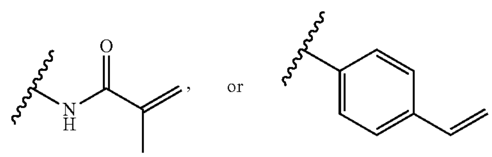

6. The compound of claim 1, wherein the compound is of Formula (I-a), (I-b), (I-b-1), (I-b-2), (I-b-3), (I-b-4), (I-b-5), (I-b-6), or (I-c):

-continued
(I-a)
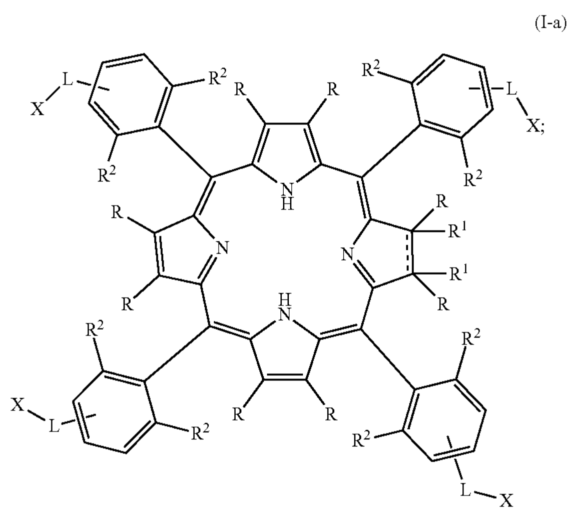
(I-b-2)
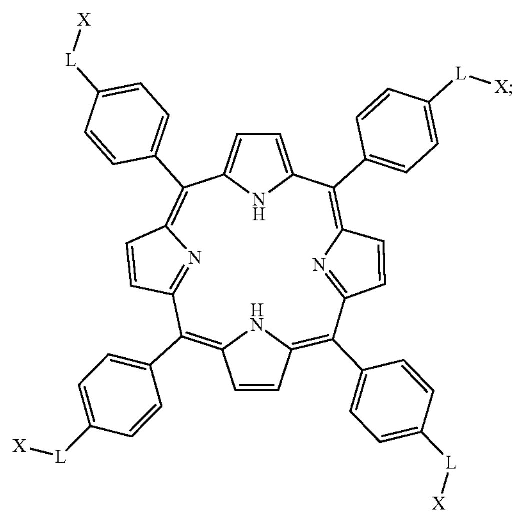
(I-b)
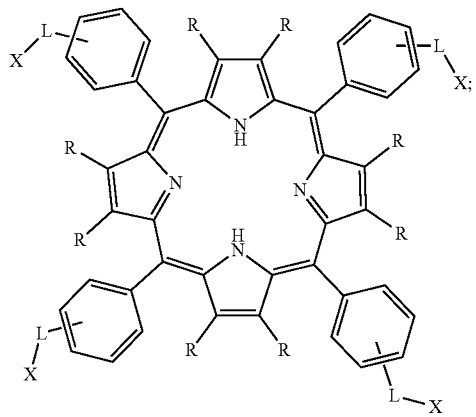
(I-b-1)
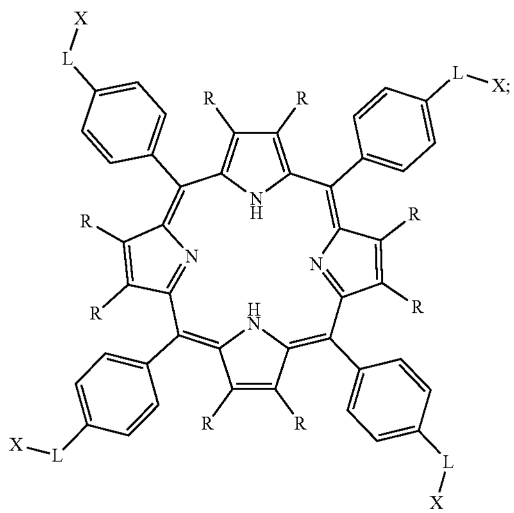
(I-b-3)
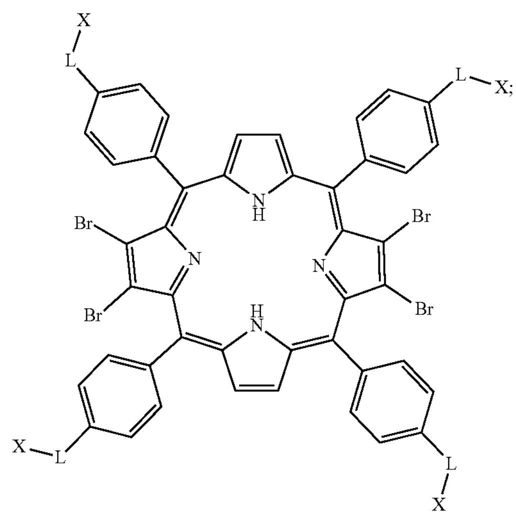

-continued
(I-b-4)
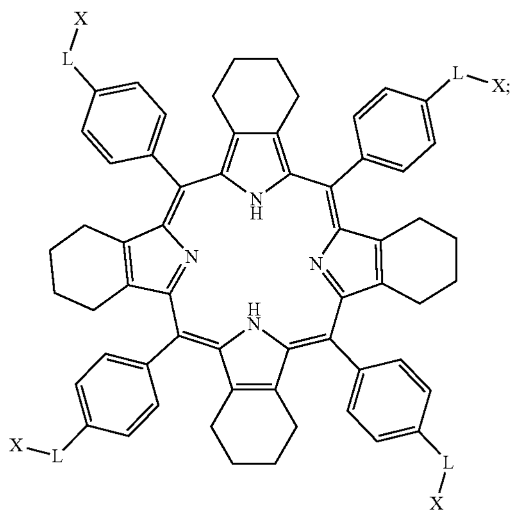
-continued
(I-b-6)
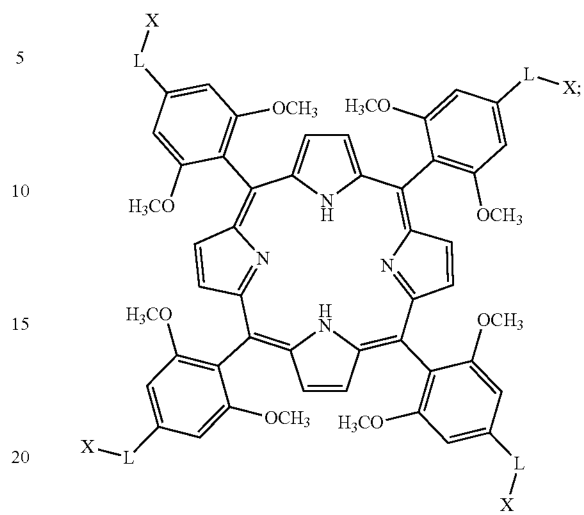
(I-b-5)
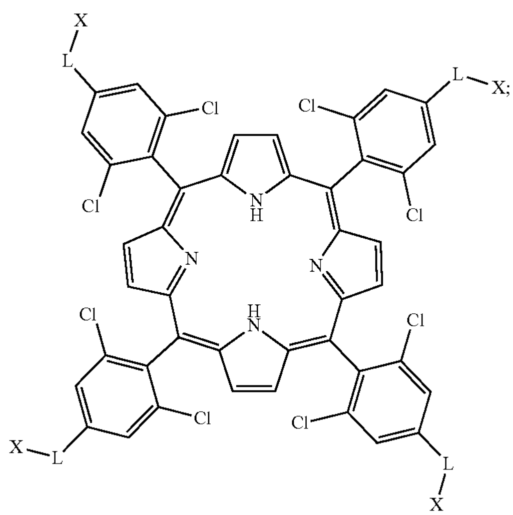
(I-c)
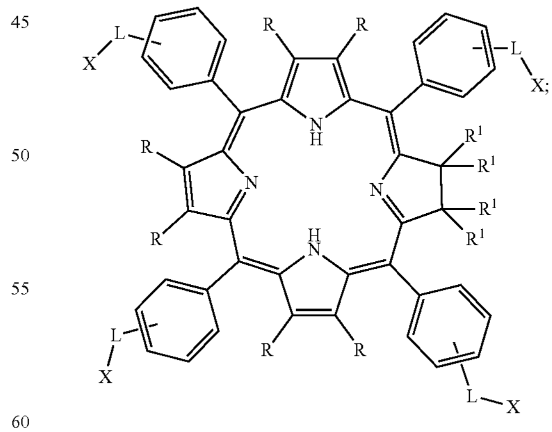
or a salt, or tautomer thereof.

7. The compound of claim 1, wherein the compound is
(1)
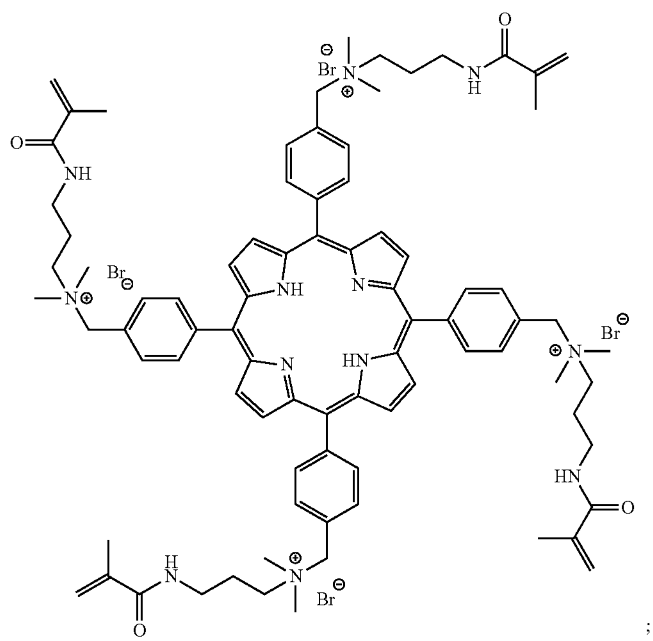
;
(2)
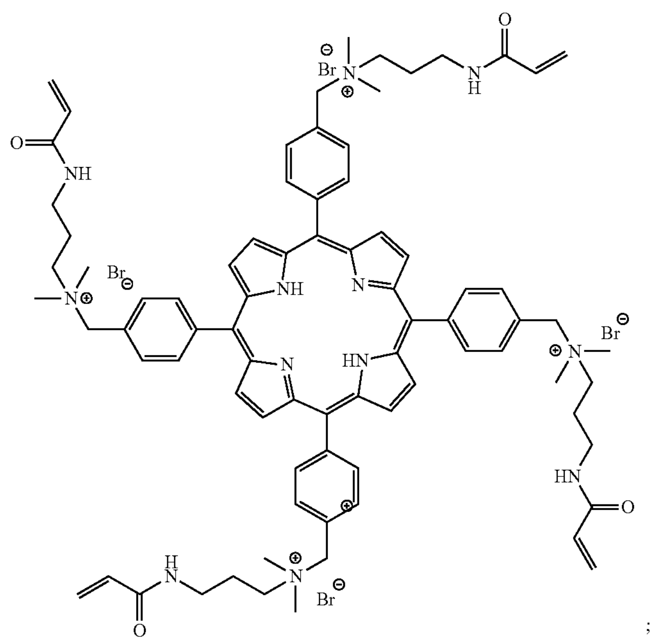
;

-continued
(3)
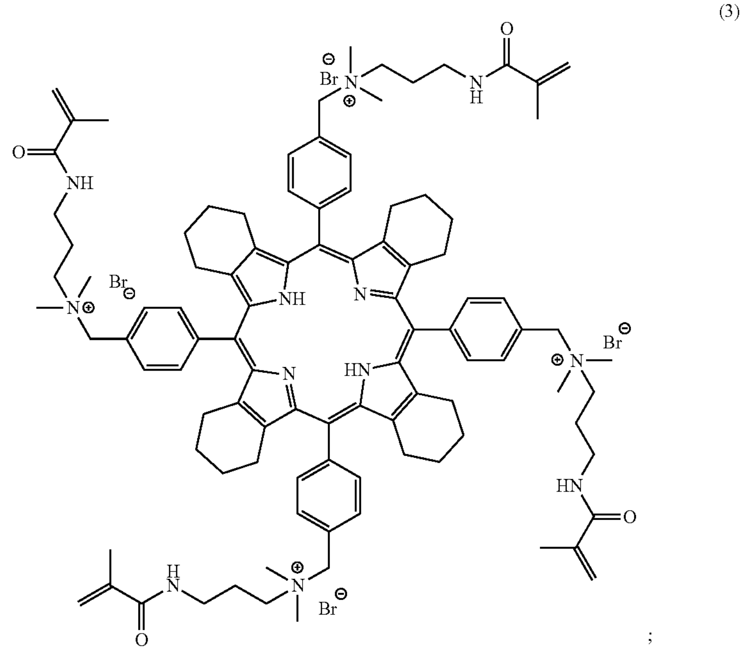
;
(4)
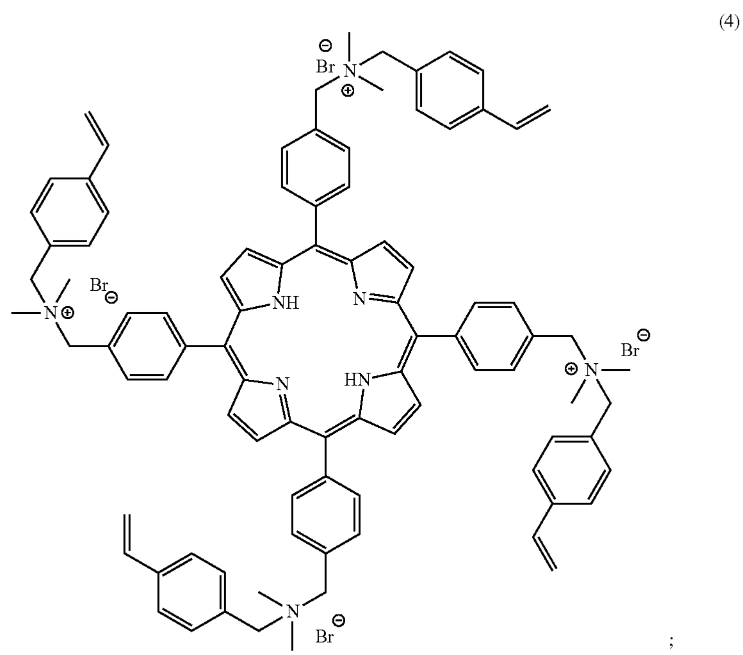
;

-continued
(5)
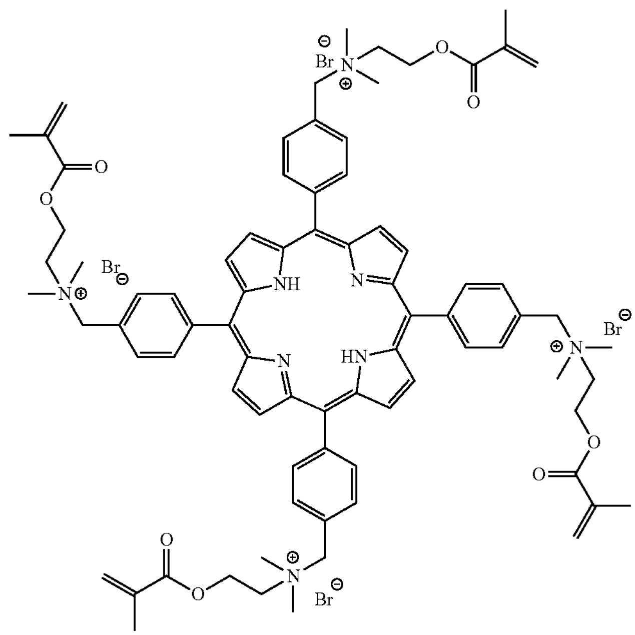
;
(6)
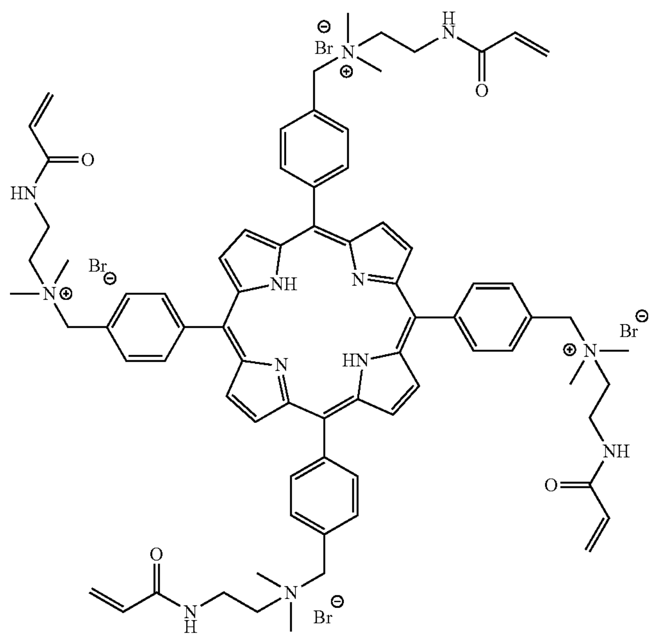
;

-continued
(7)
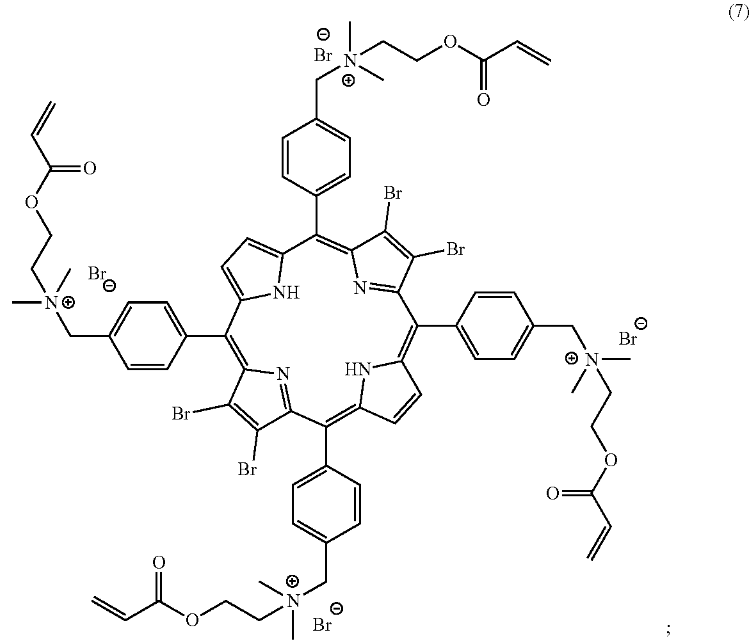
;
(15)
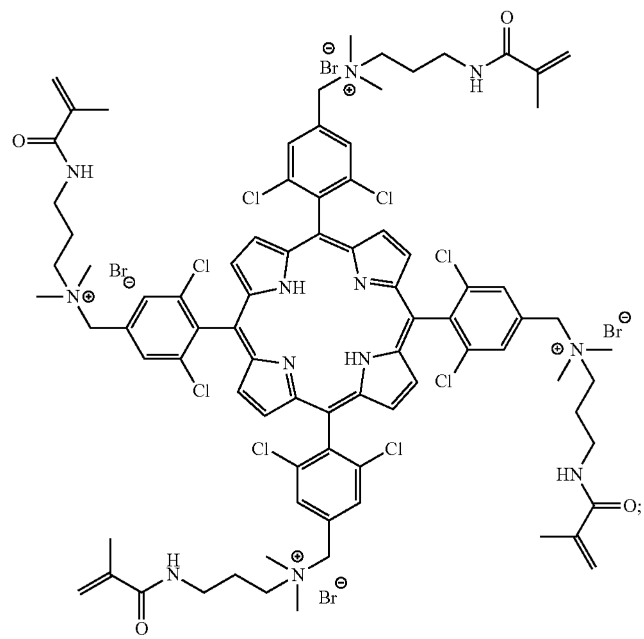

-continued
(17)
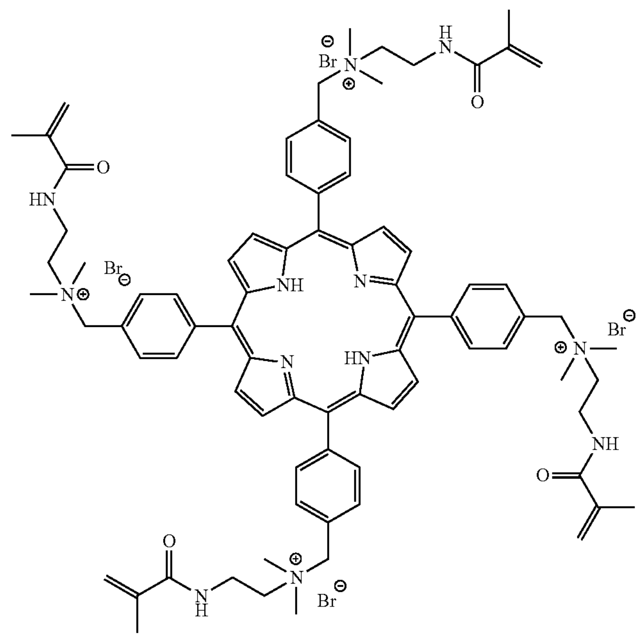
; or
(19)
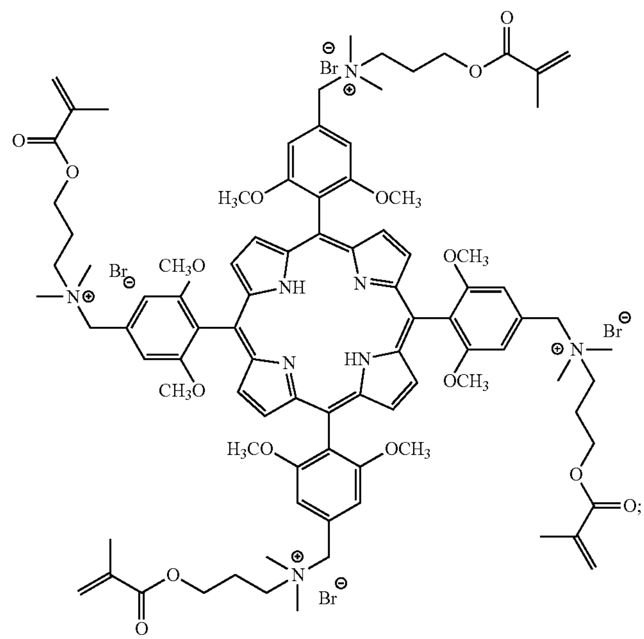
or a salt or tautomer thereof.
* * * * *